United States Patent
Al-Alusi

(10) Patent No.: US 10,206,610 B2
(45) Date of Patent: Feb. 19, 2019

(54) SYSTEMS AND METHODS FOR HIGH RESOLUTION DISTANCE SENSING AND APPLICATIONS

(71) Applicant: Transrobotics, Inc., Hayward, CA (US)

(72) Inventor: Sayf Al-Alusi, Moraga, CA (US)

(73) Assignee: TransRobotics, Inc., Hayward, CA (US)

( * ) Notice: Subject to any disclaimer, the term of this patent is extended or adjusted under 35 U.S.C. 154(b) by 219 days.

(21) Appl. No.: 14/428,075

(22) PCT Filed: Oct. 3, 2013

(86) PCT No.: PCT/US2013/063253
§ 371 (c)(1),
(2) Date: Mar. 13, 2015

(87) PCT Pub. No.: WO2015/055755
PCT Pub. Date: Apr. 10, 2014

(65) Prior Publication Data
US 2015/0223733 A1    Aug. 13, 2015

Related U.S. Application Data

(60) Provisional application No. 61/710,397, filed on Oct. 5, 2012.

(51) Int. Cl.
*A61B 6/00*     (2006.01)
*A61B 5/11*     (2006.01)
(Continued)

(52) U.S. Cl.
CPC ......... *A61B 5/1128* (2013.01); *A61B 5/0035* (2013.01); *A61B 5/0507* (2013.01);
(Continued)

(58) Field of Classification Search
CPC ... A61B 5/0035; A61B 5/1128; A61B 5/0507; A61B 5/11
See application file for complete search history.

(56) References Cited

U.S. PATENT DOCUMENTS

| | | |
|---|---|---|
| 3,796,208 A | 3/1974 | Bloice |
| 4,513,748 A | 4/1985 | Nowogrodzki et al. |

(Continued)

FOREIGN PATENT DOCUMENTS

| | | |
|---|---|---|
| GB | 2460691 A | 6/2008 |
| GB | 2489299 | 8/2012 |

(Continued)

OTHER PUBLICATIONS

Supplementary European Search Report for EP13844396—Apr. 19, 2016.

(Continued)

*Primary Examiner* — Joel F Brutus
(74) *Attorney, Agent, or Firm* — Christopher R. Carroll; The Small Patent Law Group, LLC

(57) ABSTRACT

A sensing system includes a first radar sensing assembly and an analysis system. The first radar sensing assembly measures plural distances to a first target location at different times using radar. The analysis system receives the plural distances from the first radar sensing assembly and quantifies movements of a target object at the first target location at the different times by calculating differences in the plural distances measured by the first radar sensing assembly. The analysis system generates one or more first quantified activity level values indicative of the movements of the target object at the first target location using the differences in the plural distances that are calculated.

16 Claims, 22 Drawing Sheets

(51) Int. Cl.
*A61B 5/05* (2006.01)
*G01S 7/41* (2006.01)
*G01S 13/32* (2006.01)
*G01S 13/50* (2006.01)
*G01S 13/87* (2006.01)
*G01S 13/88* (2006.01)
*A61B 5/00* (2006.01)
*G01S 7/35* (2006.01)
*A61B 5/0205* (2006.01)
*A61B 5/024* (2006.01)
*A61B 5/08* (2006.01)
*A61B 5/113* (2006.01)
*A61B 5/1455* (2006.01)

(52) U.S. Cl.
CPC ............ *A61B 5/11* (2013.01); *A61B 5/1112* (2013.01); *A61B 5/1114* (2013.01); *A61B 5/1117* (2013.01); *A61B 5/1118* (2013.01); *A61B 5/7246* (2013.01); *A61B 5/7278* (2013.01); *G01S 7/415* (2013.01); *G01S 13/325* (2013.01); *G01S 13/50* (2013.01); *G01S 13/87* (2013.01); *G01S 13/88* (2013.01); *A61B 5/024* (2013.01); *A61B 5/0205* (2013.01); *A61B 5/02416* (2013.01); *A61B 5/05* (2013.01); *A61B 5/0816* (2013.01); *A61B 5/113* (2013.01); *A61B 5/1135* (2013.01); *A61B 5/14551* (2013.01); *A61B 5/14552* (2013.01); *A61B 2562/0233* (2013.01); *A61B 2576/00* (2013.01); *G01S 2007/358* (2013.01)

(56) References Cited

U.S. PATENT DOCUMENTS

| | | | |
|---|---|---|---|
| 5,131,754 | A | 7/1992 | Hasegawa |
| 5,361,070 | A | 11/1994 | McEwan |
| 5,471,198 | A | 11/1995 | Newham |
| 6,218,982 | B1 | 4/2001 | Shirai et al. |
| 6,466,125 | B1 | 10/2002 | Richards et al. |
| 6,504,483 | B1 | 1/2003 | Richards et al. |
| 6,661,342 | B2 | 12/2003 | Hall et al. |
| 6,788,206 | B1 | 9/2004 | Edwards et al. |
| 6,900,732 | B2 | 5/2005 | Richards et al. |
| 7,567,200 | B1 * | 7/2009 | Osterweil ............ A61B 5/1117 340/573.1 |
| 2003/0117310 | A1 | 6/2003 | Kikuchi et al. |
| 2003/0151542 | A1 | 8/2003 | Steinlechner et al. |
| 2003/0320570 | | 11/2003 | Ragnarsdottir |
| 2004/0249258 | A1 | 12/2004 | Tupin et al. |
| 2005/0013465 | A1 | 1/2005 | Southall et al. |
| 2005/0078029 | A1 | 4/2005 | Okamura et al. |
| 2006/0058683 | A1 * | 3/2006 | Chance ............ A61B 5/0059 600/476 |
| 2009/0074031 | A1 | 3/2009 | Fukuda |
| 2010/0048313 | A1 | 2/2010 | Mooney |
| 2010/0130873 | A1 * | 5/2010 | Yuen ................... A61B 5/0205 600/484 |
| 2012/0179011 | A1 | 7/2012 | Moon et al. |

FOREIGN PATENT DOCUMENTS

| | | |
|---|---|---|
| JP | 04193158 A | 7/1992 |
| JP | 1993256936 A | 10/1993 |
| JP | 0627229 A | 2/1994 |
| JP | 2000121726 A | 4/2000 |
| JP | 2009528859 A | 8/2009 |
| WO | 02097468 A2 | 12/2002 |
| WO | 2004047630 A1 | 6/2004 |
| WO | 2007101343 A1 | 9/2007 |
| WO | 2008057883 A2 | 5/2008 |
| WO | 2008057883 A3 | 5/2008 |
| WO | 2011143631 A2 | 11/2011 |
| WO | 2011143631 A3 | 11/2011 |
| WO | 2012054086 | 4/2012 |
| WO | 02097468 A2 | 3/2015 |

OTHER PUBLICATIONS

ISR and WO for PCT/US2013/063253 dated Jan. 20, 2014 (11 pgs.).
Search Report for corresponding European Application No. 17 19 843; dated Feb. 2, 2018; 12 pages.
Examination Report for corresponding European Application No. 12/782,290.6-1812; dated Nov. 29, 2016; 7 pages.
Search Report for corresponding European Application No. 17 19 843; dated May 16, 2018; 11 pages.

* cited by examiner

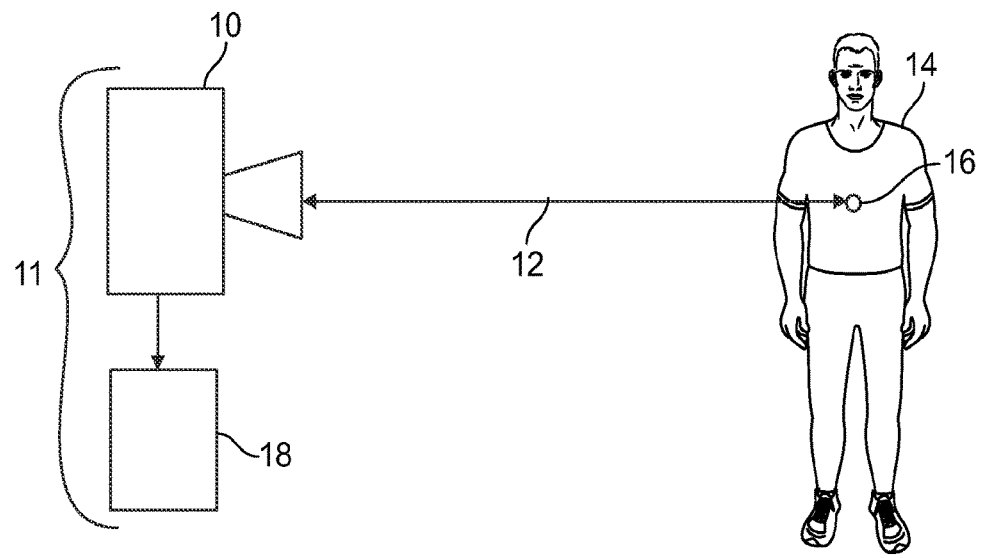
FIG. 1
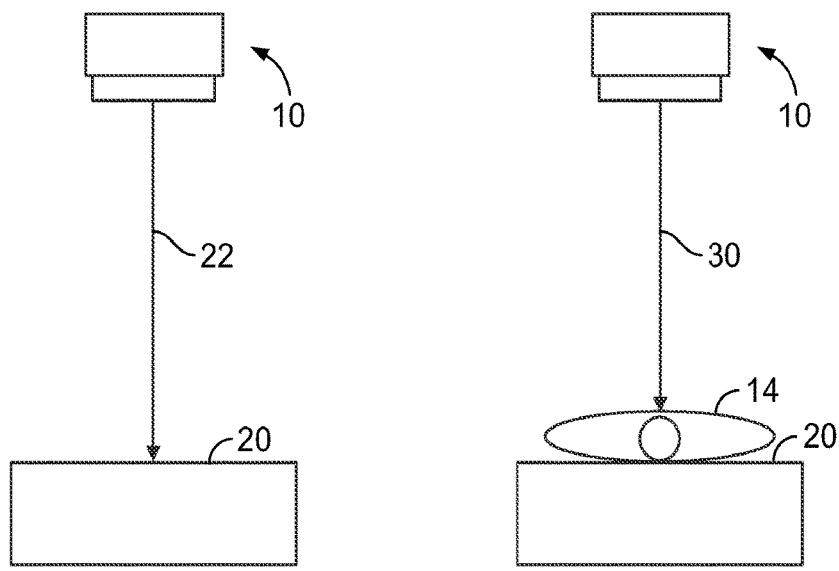
FIG. 2   FIG. 3

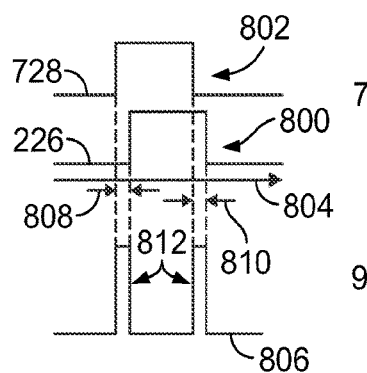
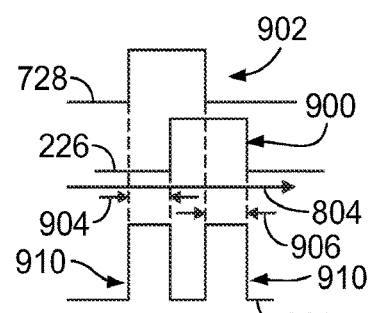
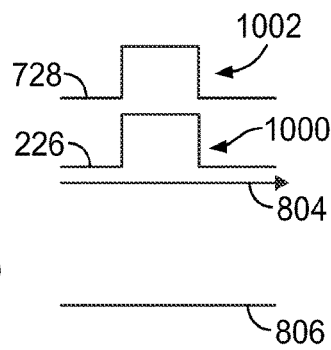
FIG. 26　　　FIG. 27　　　FIG. 28
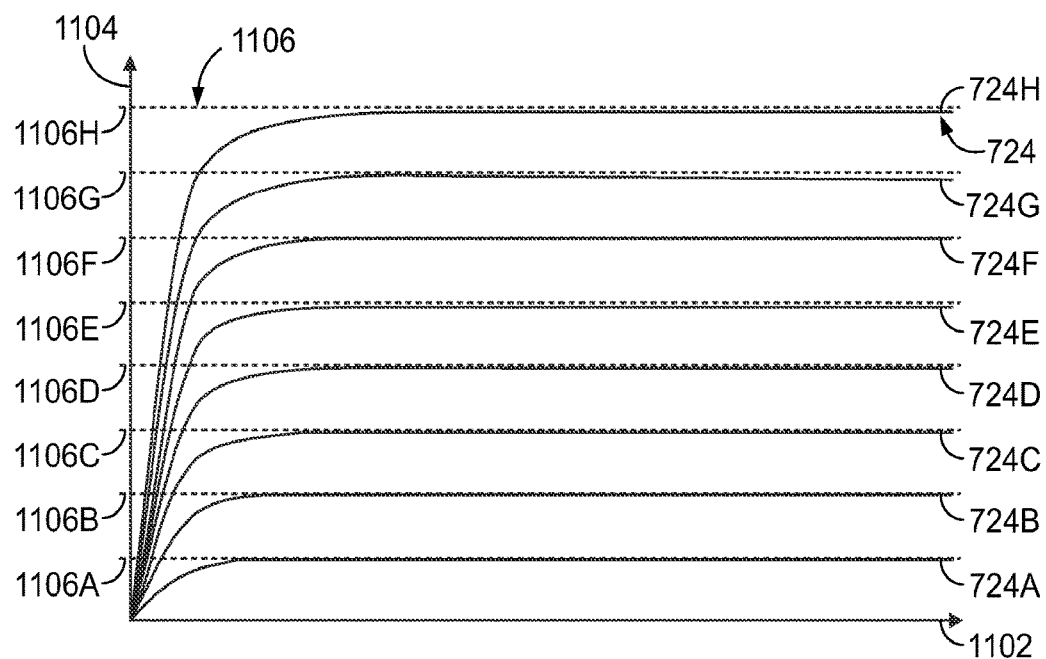
FIG. 29

SYSTEMS AND METHODS FOR HIGH RESOLUTION DISTANCE SENSING AND APPLICATIONS

CROSS-REFERENCE TO RELATED APPLICATIONS

This application is a national stage entry of, and claims priority to, International Application No. PCT/US2013/063253, having an international filing date of 3 Oct. 2013, which claims priority to U.S. Provisional Application Ser. No. 61/710,397, filed 5 Oct. 2012, and titled "High Resolution Distance Sensing And Its Applications And Systems," the entire disclosures of which are incorporated by reference.

TECHNICAL FIELD

One or more embodiments described herein relate to non-contact, non-invasive sensing of vital signs or other health signals using radar or other high-resolution distance sensing.

BACKGROUND

Known radar systems transmit analog electromagnetic waves toward targets and receive echoes of the waves that reflect off the targets. Based on the distance between antennas that transmit the analog waves and the target objects, and/or movement of the target objects, the strength and/or frequency of the received echoes may change. The strength, frequency, and/or time-of-flight of the echoes may be used to derive the distance to the targets and/or movement of the targets.

Some known radar systems are limited in the accuracy at which the systems can measure distances to the targets. For example, the resolution at which these systems may be able to calculate the distance to targets may be relatively large. Moreover, some of these systems may have circuitry, such as a transmit/receive switch, that controls when the systems transmit waves or receive echoes. The switch can require a non-zero period of time to allow the systems to switch from transmitting waves to receiving echoes. This period of time may prevent the systems from being used to measure distances to targets that are relatively close, as the transmitted waves may reflect off the targets back to the receiving antennas before the systems can switch from transmission to reception. Additionally, some known systems have energy leakage from the transmitting antenna to the receiving antenna. This energy leakage can interfere with and/or obscure the measurement of distances to the targets and/or the detection of motion.

BRIEF DESCRIPTION

In an embodiment, a sensing system includes a first radar sensing assembly and an analysis system. The first radar sensing assembly measures plural distances to a first target location at different times using radar. The analysis system receives the plural distances from the first radar sensing assembly and quantifies movements of a target object at the first target location at the different times by calculating differences in the plural distances measured by the first radar sensing assembly. The analysis system generates one or more first quantified activity level values indicative of the movements of the target object at the first target location using the differences in the plural distances that are calculated.

In an embodiment, a sensing method includes transmitting first electromagnetic waves toward a first target location from a first radar sensing assembly at different times, receiving first echoes of the electromagnetic waves that are reflected off the first target location using the first radar sensing assembly, measuring plural distances to the first target location using the first echoes of the electromagnetic waves, quantifying movements of a target object at the first target location at the different times by calculating differences in the plural distances measured by the first radar sensing assembly, and generating one or more first quantified activity level values indicative of the movements of the target object at the first target location using the differences in the plural distances that are calculated.

BRIEF DESCRIPTION OF THE DRAWINGS

The present subject matter will be better understood from reading the following description of non-limiting embodiments, with reference to the attached drawings, wherein below:

FIG. 1 is a schematic illustration of an embodiment of a sensing system;

FIG. 2 is a schematic illustration of using the sensing system to detect presence or absence of a target at a monitored location;

FIG. 3 is another schematic illustration of using the sensing system to detect presence or absence of a target at a monitored location;

FIG. 26 is a schematic diagram of one example of how a comparison device compares a bit of interest of a baseband echo signal shown in FIG. 19 with a pattern bit of a pattern signal shown in FIG. 19 in one embodiment;

FIG. 27 illustrates another example of how the comparison device shown in FIG. 25 compares a bit of interest of the baseband echo signal shown in FIG. 19 with a pattern bit of the pattern signal shown in FIG. 19;

FIG. 28 illustrates another example of how the comparison device shown in FIG. 25 compares a bit of interest of the baseband echo signal shown in FIG. 19 with a pattern bit of the pattern signal shown in FIG. 19;

FIG. 29 illustrates examples of output signals shown in FIG. 25 provided by measurement devices shown in FIG. 25 and energy thresholds used by a CPU device shown in FIG. 19 in accordance with one example;

DETAILED DESCRIPTION

Figures 4, 5, 6, 7:
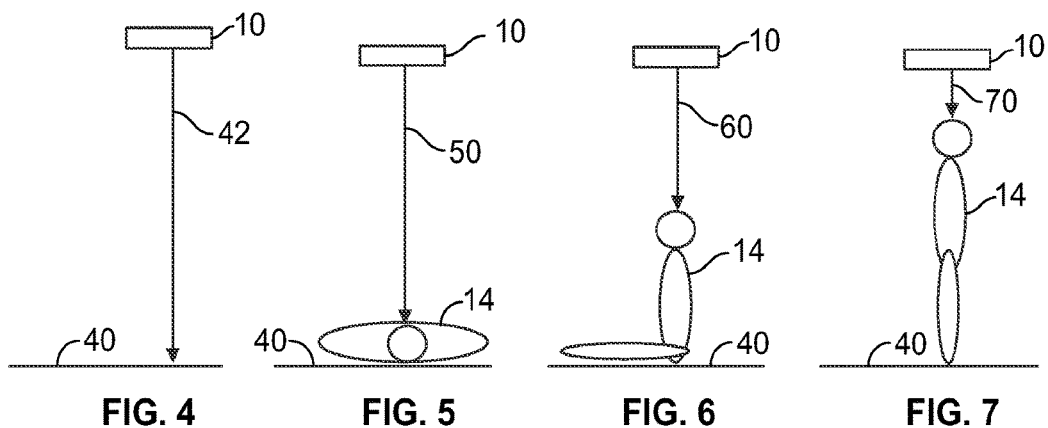
FIG. 4 is an additional schematic illustration of using the sensing system to monitor position and/or posture of a target at a monitored location.
FIG. 5 is an additional schematic illustration of using the sensing system to monitor position and/or posture of a target at a monitored location.
FIG. 6 is an additional schematic illustration of using the sensing system to monitor position and/or posture of a target at a monitored location.
FIG. 7 is an additional schematic illustration of using the sensing system to monitor position and/or posture of a target at a monitored location.

FIG. 1 is a schematic illustration of an embodiment of a sensing system 11. In one or more embodiments of the inventive subject matter described herein, the sensing system includes a high-resolution distance sensing assembly 10 (also referred to as a sensor) is used to measure a distance 12 to one or more targets 14, and/or the position of the target or targets. The target can include a living being, such as a human or other animal. A specific target location 16 may be any physical point of the body, tissue interface, or other transition in material of the target, such as the front of the chest, the hand, or any part of the body of the target, any surface of the body, an internal structure of the body of the target (such as the heart or lungs), or the like. The target location may be less than the entirety of the target, and may be a relatively small location, such as a single point, line, or the like. The target location represents the part of the target from which the distance is measured by the sensing system. One embodiment of the sensing system is described below in connection with FIGS. 18 through 38B.

The accuracy of the distance or position sensing can be any level that allows for the extraction of meaningful health signals of the target, such as vital signs of the target, as described below. The sensing system may be radar-based that uses radar techniques to measure the distance and/or position to one or more targets. In one embodiment, the position and/or distance to the targets can be measured to less than 1 millimeter accuracy (e.g., 0.2 millimeter accuracy) at a relatively fast rate, such as 1000 times or more per second. Optionally, the sensing system may measure the position and/or distance at a different accuracy and/or at a different rate.

The sensing assembly may communicate (e.g., transmit and/or broadcast) data representative of the distance and/or location of the target to an analysis system 18 of the sensing system for storage and/or further analysis of the data. The data can be communicated through, over, and/or using one or more wired and/or wireless connections to the analysis system. The analysis system can include or represent one or more computer devices, such as one or more laptops, desktops, workstations, personal digital assistants, servers, blade servers, mainframes, and other appropriate computers).

The analysis system can extract or derive various other signals or measures of significance to the health or well-being of a person or animal (e.g., the target) from the data provided by the sensing system, as described below. For example, a signal related to the breathing of a patient or user can be extracted by the analysis system, or a signal related to the cardiac activity of the patient or user or the activity of the patient or user, or any other measure of the health or well-being of the patient or user may be derived. Additionally or alternatively, these health signals may be extracted or derived by the sensing system. These extracted signals may then be transmitted to another system for storage or further processing.

The sensing system collects high-resolution estimates or measurements of the position or distance to the one or more targets, which is referred to herein as the "raw" or "raw distance" or "raw position" data. This data can be communicated to the analysis system for storage and/or further processing. The raw data can be stored before or after the data is processed. The raw data can be processed or filtered, and/or other calculations can be performed on the raw data to extract or derive other signals, such as the respiration of the patient or user. These signals can be referred to as computed signals or auxiliary signals. The computed signals can also be stored in the analysis system or elsewhere. One or more auxiliary signals can be extracted, derived, or computed from the computed signal and then stored. In another embodiment, the raw data and all computed or extracted signals can be stored. Further signals can be extracted from the stored raw data in the future, and these can be saved as well. The raw data and extracted signals can all be used in any combination to compute other measures related to health or well-being. Alternatively, or in addition, the sensing system may possess sufficient computational ability to extract the signals and perform the computations. The sensing system may then transmit these signals to another system for storage or further analysis. It may transmit the raw data as well, or switch between two or more modes depending on other signals or observations. For example, the sensing system may extract a signal related to the presence of a subject (described below) and make an initial determination of the presence of a subject. Then, when it is determined that a subject is present, the sensing system switches modes to communicate the raw data to another computer system to perform further, more complex, analysis. When the data is transmitted to another system, the data may be further analyzed and/or stored.

FIGS. 2 and 3 are schematic illustrations of using the sensing assembly 10 to detect presence or absence of a target at a monitored location. In the illustrated example, the sensing assembly is directed toward a monitored location 20 where a target subject may or may not be located. For example, the sensing assembly may be oriented toward a bed or a chair. A reference or baseline distance (or position) 22 of the monitored location relative to the sensing assembly may be established. For example, if the monitored location is a bed, the sensing assembly may be situated (e.g., mounted) above the bed and directed downward toward the bed so that the sensing system can measure the reference or baseline distance 22 between the sensing assembly and the monitored location. This reference or baseline distance (or position) can represent the distance or position to an object or location when there is no subject present (e.g., there is no person in the bed).

The sensing system can continue to monitor the distance between the sensing assembly and the monitored location. When this distance or position changes or decreases (e.g., moves closer), the sensing system may infer that there is now a person or other subject (e.g., a target) 14 present in the monitored location, since the target has a non-zero thickness and the sensing assembly senses the absolute distance between the sensing system and the monitored location rather than simply monitoring motion. For example, the sensing assembly may not monitor motion, but instead may periodically, randomly, and/or upon operator demand measure the distance 22 to identify changes in the distance. Decreases in this distance (e.g., from the baseline distance 22 to a modified distance 30) may represent the arrival of a target at the monitored location. Conversely, increases in this distance can represent the departure of the target from the monitored location. The position or distance data that is acquired by the sensing system (e.g., the raw data) can be saved and/or filtered using a low-pass filter, a finite-impulse-response (FIR) filter or an infinite-impulse-response (IIR) filter, wavelet transform, or a combination of these techniques, or others. The presence or absence of the target from the monitored location can be used to assess various aspects of the health of the target, such as by monitoring how often and/or long the target remains in the monitored location.

FIGS. 4 through 7 are additional schematic illustrations of using the sensing system to monitor position and/or posture of a target at a monitored location. In the illustrated example, the sensing assembly 10 is directed (e.g., oriented) toward a monitored location 40 where a subject may or may not be present, such as a bed, chair, or floor. A reference or baseline distance or position 42 can be measured by the sensing system, similar to as described above in connection with FIG. 2. This reference distance or position or baseline distance or position is the distance or position to an object or location when there is no subject present. Information about the arrangement, positions, relative positions, locations, pointing directions, and other physical information about the physical environment of the objects and sensing system may be recorded as well. A new position or distance or changes in distance or position of different magnitudes indicates different positions or posture of a subject that has entered the monitored area. For example, the monitored location may be a bed and the sensing system situated above the bed and directed downward toward the bed. The sensing system may monitor distances 50 to the bed to identify changes in the distance from the baseline distance 42. A smaller change in distance or position 60, for example 10 inches (e.g., 25 centimeters) can indicate that there is now a person (e.g., a target 14) lying in the bed, as shown in FIG. 5. A larger change in distance 70 (e.g., 3 feet or 91 centimeters) may indicate that there is a person sitting upward in the bed, as shown in FIG. 6. In other situations, such as when the sensing system is pointed at the floor as a monitored location, a larger change in the distance 50 from the baseline distance 42 (e.g., a change of 6 feet or 183 centimeters) could indicate that there is a person standing under the sensing system, as shown in FIG. 7.

The sensing system can measure different distances or position to a target that has entered the scene (e.g., the monitored location). Changes in the distances can be used to determine the position (e.g., within or not within the monitored location), posture (e.g., lying prone, sitting up, standing, or the like), or other relevant metric of the target. The position or distance data obtained by the sensing system (e.g., the raw data) can be saved and filtered using a low-pass filter, a finite-impulse-response (FIR) filter or an infinite impulse-response (IIR) filter, wavelet transform, or a combination of these techniques, or other filtering techniques.

While the sensing system is shown in FIGS. 4 through 7 as being disposed directly above the monitored location, optionally, the sensing system could be mounted in another location, such as in the corner of a room or other location that is not directly above the target or monitored location. In this case, the observations and measurements of distance will be at an angle, but operation of the sensing system described above may be substantially the same.

Additionally or alternatively, certain specific positions or distances of targets associated with various parts of a body of the target may indicate certain positions or postures of the target. Different measured distances between the sensing system and the target may be associated with different positions or postures of the target. For example, the sensing system can be mounted in the ceiling of a bedroom and directed toward a bed. A target measured at 5.5 feet (e.g., 168 centimeters) away from the sensing system can indicate that the target is lying in bed. A target measured at 4 feet (e.g., 122 centimeters) from the sensing system may indicate that the target is sitting in the bed. This can be used to assess various aspects of the health of the target. As another example, the sensing system can measure the distances between the sensing system and the monitored location and compare the distances and/or changes in the distances to one or more thresholds. These thresholds may be associated with different postures or positions of the target. For example, a distance between the sensing system and the monitored location that exceeds a first threshold may indicate that there is no target at the monitored location. A distance that exceeds a smaller, second threshold but not the first threshold (and/or a change in this distance that is smaller than a first differential threshold) may indicate that the target is lying down in the monitored location. A distance that exceeds a smaller, third threshold but not the second threshold (and/or a change in the distance that is smaller than a second differential threshold but larger than the first differential threshold) may indicate that the target is sitting up in the monitored location. A distance that exceeds a smaller, fourth threshold but not the third threshold (and/or a change in the distance that is smaller than a third differential threshold but larger than the second differential threshold) may indicate that the target is standing in the monitored location.

The position or posture of a person over time can be observed or measured as described above. This data can then be used to determine if the person suffered a fall during that time period. As an example, the sensing system may measure an object at 5.5 feet (e.g., 168 centimeters) above a floor, which can correspond to the head of a person and can indicate that the person has entered a field of view of the sensing system. The systems may continue to monitor the distance to the person's body and observe that the body moved closer to the floor over a relatively short period of time. If the body then remains in relatively close proximity to the floor, for example less than two feet (e.g., 61 centimeters) or another distance, for an extended period of time (such as 30 seconds or another time period), the system may then produce an alert signal that indicates the person under observation has or had suffered a fall.

As another example, the sensing system may be directed toward a target, such as a person or animal. In the case of the target being a person or animal, the target location may be any part of the body, any external surface of the body, or an internal structure of the body. A new position or distance or change in the position or distance to a target from the sensing system can be indicative of physical activity of the target or target location. Information about the arrangement, positions, relative positions, locations, pointing directions, and/or other physical information about the physical environment of the targets and sensing system may be recorded. A time series or history of activity may be recorded over some period of time, such as seconds, minutes, hours, days, or even years or more. The time record of data can be used to extract a relative or absolute activity level for the target. The position or distance data (e.g., the raw data) can be saved and filtered using filtering, such as a low-pass filter, a finite-impulse-response (FIR) filter or an infinite-impulse-response (IIR) filter, wavelet transform, or a combination of these techniques, or others. If the physical environment information is used as well (e.g., if the monitoring location and/or locations of objects other than the target or target location are known), then the activity that is detected by the changes in distance as measured by the sensing system may be associated with activity in different parts of the body of the target. The situations of FIGS. 2 through 7 are examples of this. For example, if a person is lying in bed and moves their legs, the target location associated with the legs will have a new position or change in distance, which thereby can indicate motion. This information can be saved and/or communicated to another system or part of the system. The time record of the activity can be computed to determine an activity level. This can be used to assess various aspects of the health of the target.

The activity level may be quantified by the analysis system. For example, instead of merely identifying movement as an activity level, the analysis system may generate one or more numerical values indicative of the magnitude of the activity level. Larger activity level values indicate more movement of the target (e.g., larger movements and/or faster movements) while smaller activity level values indicate less movement of the target (e.g., smaller movements and/or slower movements). The quantified activity level values may be used to identify different types of movement events, as described herein. For example, relatively large activity level values may indicate that the target has fallen down, that the target is breathing rapidly, that the target has a relatively fast heart rate, and the like. Conversely, relatively small activity level values may indicate that the target is remaining still, that the target is breathing slowly or not at all, that the target has a relatively slow heart rate or no heart rate, and the like.

Figure 8:
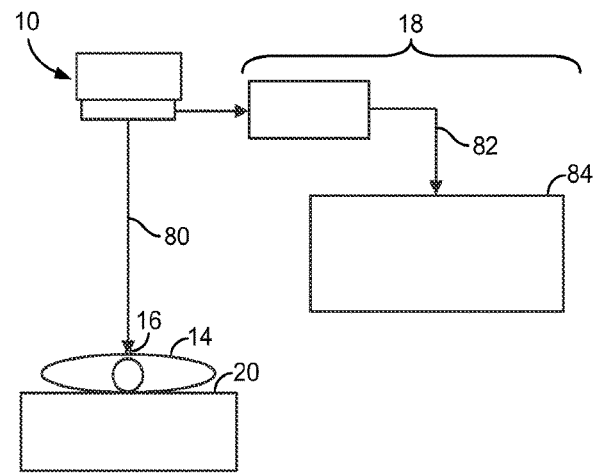
FIG. 8 is a schematic illustration of using the sensing system to monitor respiration of a target.

FIG. 8 is a schematic illustration of using the sensing assembly 10 to monitor respiration of a target. The sensing assembly 10 can be directed toward the target 14, similar to as described above, and measure distances 80 to a target location 16 of the target or the position of the target. In the case of the target being a person or animal, the target location may be any part of the body, any surface of the body, an internal structure of the body, or the like. In order to monitor respiration of the target, the target location may be the front of the chest, the rib cage, other structure around the lungs, the lungs, and/or another part of the target having movements that change due to breathing (e.g., respiration) by the target. As described below, the sensing system can include the ability to monitor very small changes in distances to the target, such as those distances to the chest or other area of the target that may change due to breathing by the target.

The position and/or distance from the sensing system to the target location is tracked or monitored over time. Changes in this distance and/or position can indicate breathing by the target. The analysis system 18 can monitor the distances and/or position, and/or changes in the distance and/or position, in order to identify and track respiration movements of the target. In order to avoid confusing respiration movements with other movements (e.g., rolling over in bed, shifting positions in bed, and the like), the analysis system may isolate the distances, positions, and/or changes in distances and/or positions representative of respiration movements from other distances, positions, and/or changes in distances and/or positions that are not representative of respiration movements. The analysis system may isolate the respiration-indicative distances, positions, and/or changes in distances and/or positions using one or more filters applied to the data acquired by the sensing system, such as by applying a low-pass filter, a finite-impulse response (FIR) filter or an infinite-impulse-response (IIR) filter, wavelet transform, a combination of filters, or one or more other filters. The analysis system or other system can monitor respiration of the target to assess various aspects of the health of the target. The analysis system can generate an output signal 82 that is communicated (e.g., transmitted and/or broadcast) to an output device 84, such as a monitor, speaker, haptic device, light, or the like. The output signal may direct the output device to generate an output, such as a visual, audible, and/or haptic alarm. For example, the analysis system can track breathing patterns during sleep for persons suffering from sleep apnea and generate the output signal to allow a physician to examine the breathing patterns of the target during sleep. As another example, the analysis system can track or monitor breathing of infants or others and generate an alarm by communicating the output signal to warn others of potential problems or cessation of breathing by the target, such as to prevent Sudden Infant Death Syndrome.

In one aspect of monitoring respiration, the analysis system may have information or collect information about the overall physical size of the chest of the target, such as via physical measurements, a camera, or other method. The analysis system can then combine this additional data with the distance or position data obtained by the sensing system. The change in distance or position of the front of the chest, combined with information about the lateral area or physical size of the chest can be used to calculate the volume of air that is taken into and then expelled from the lungs, such as the tidal volume.

The example of the sensing system and analysis system additionally or alternatively may be used to track or monitor cardiac functions of the target. The target location used by the sensing system can include the front of the chest, the rib cage, another structure around the heart, the heart, and/or another location that moves due to cardiac cycles of the target. This target location can be tracked or the distance or position between the sensing system and the target location measured, and can be indicative of cardiac functioning of the target. Similar to as described above with respect to monitoring respiration, however, some movements that are tracked by the sensing system may be from actions other than cardiac cycles. The position or distance data, e.g., the raw data, can be saved and/or filtered by the analysis system using one or more filters described herein in order to isolate the movements representative of cardiac functions from other movements. The analysis system can generate the output signal to the output device to allow the cardiac functions of the target to be analyzed.

In one aspect, the analysis system may simultaneously (or concurrently) use multiple levels or versions of the wavelet transform to examine the data generated by the sensing system. The analysis system can use a wavelet transform to extract a cardiac signal from raw position or distance information to the heart or the chest or other body structure, as measured and generated by the sensing system. Furthermore, multiple levels of the wavelet transform may be used by the analysis system to extract and/or reconstruct the cardiac signal. While a typical wavelet transform uses a single wavelet, such as the Symmlet-6 or the Daubechies-8 wavelet, the analysis system can process the raw distance, position, or motion data using more than one wavelet to extract the cardiac signal. Additionally, both of the above methods may be used together, for example, multiple levels of the Symmlet-7 and Daubechies-10 wavelets may be used in a wavelet transform to extract the cardiac signal.

Figure 9:
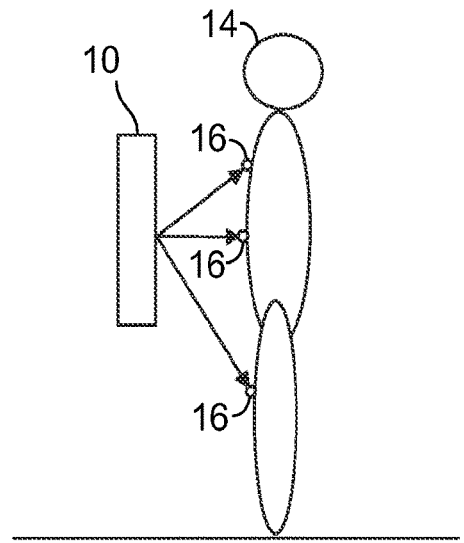
FIG. 9 is a schematic illustrating of using the sensing system to monitor gait and/or balance of a target.

FIG. 9 is a schematic illustrating of using the sensing assembly 10 to monitor gait and/or balance of a target 14. The sensing system can be directed toward the target, such as a person or animal. In one example, the target location 16 may be any part of the target, any surface of the target, an internal structure of the target, or another location.

The sensing system may have several target locations on the target and/or multiple sensing systems may be used, with two or more of the sensing systems having different target locations on the same target. For example, there may be multiple target locations in a radar beam generated by the sensing system or in a field of view of the sensing system. In an embodiment, the sensing system may be unable to distinguish between the multiple target locations. For example, the sensing system may be unable to separate the distance, position, and/or motion of the multiple target locations from each other. The sensing system can measure a superposition or summation of the positions and/or distances to the multiple target locations. The analysis system 18 may then process the data as described herein to extract or compute various observations of the position and/or distance or pattern of position and/or distance of the target locations.

The sensing system may be directed toward a target (e.g., a person or animal) that is standing or walking. The sensing system may be directed horizontally to measure the position and/or distance pattern or motion of the target as the target moves along a path. The analysis system may then extract or compute information regarding the gait or balance of the target from the distances and/or positions obtained by the sensing system. This can be used to assess various aspects of the health of the subject.

For example, the sensing system may sense the distance to one or more target locations of the target and the sensing system and/or analysis system may monitor the distances with respect to time to generate a time record of the positions and/or distances of one or more target locations. Such a record can include several different positions and/or distances, and the times at which the positions and/or distances were measured (e.g., time stamps). From this record, the motion, speed, velocity, and/or motion vector of the target and/or one or more target locations can be computed by the analysis system, such as by using the first difference method or another technique. Alternatively, a total change in position and/or distance to the target and/or one or more target locations may be computed by the analysis system, such as by a summation of the motion or another technique. If initial conditions or boundary conditions of the target are known, then the analysis system may compare the distances and/or locations sensed by the sensing system with these conditions in order to determine an actual position and/or distance of the target and/or one or more target locations. These boundary conditions may include the actual locations of surfaces around or near the target, such as locations and/or distances from the sensing system to walls, ceilings, floors, furniture, and the like. This computed motion or computed position may be used interchangeably in the various embodiments and examples of uses of the sensing system described herein.

Figure 10:
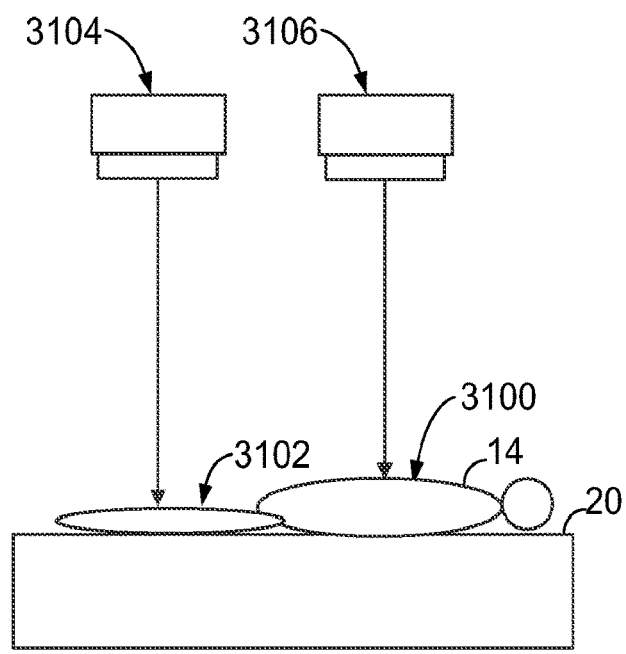
FIG. 10 is a schematic illustration of using multiple sensing systems to monitor a common target at different target locations.

FIG. 10 is a schematic illustration of using multiple sensing systems 3104, 3106 to monitor a common target 14 at different target locations. The sensing systems 3104, 3106 may each represent a separate sensing assembly 10. In the case of activity sensing described above, one sensing system 3104 may be directed at an upper part 3100 of the target 14 (e.g., the head and/or torso) and another sensing system 3106 directed at the lower part 3102 (e.g., the legs). In this way, activity in different parts of the same target may be separately monitored by the sensing systems, as shown in FIG. 10. As another example, one sensing system may be directed at a chest of a target and another sensing system directed at an abdomen (e.g., stomach) of the target. As described above, these sensing systems can be used to determine the breathing of the target as movement in the chest and movement in the abdomen that is monitored by the separate sensing systems may occur during breathing. The analysis system may examine (e.g., compare) the data provided by the sensing systems to determine abnormal breathing patterns, such as paradoxical breathing or labored breathing. For example, changes in movements detected by the sensing systems may be compared to templates or known patterns of changes in movements in the chest and/or abdomen. Different templates or known patterns may be associated with different abnormal breathing events. The analysis system can determine which of these templates or known patterns is matched by the actual data obtained by the sensing systems (or which template and/or known pattern is more closely matched by the actual data than one or more other templates or patterns) and identify the abnormal breathing event associated with this template or pattern as occurring in the target. These multiple sensing systems therefore can be used to determine a more precise location or orientation or context for the distance or position or motion measurement than could be provided by an individual sensing system.

Figure 11:
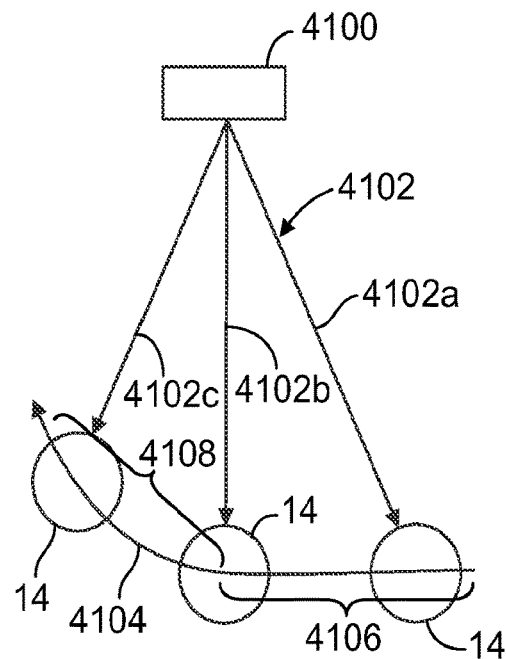
FIG. 11 illustrates an example of using a sensing system to monitor movement of a target.

FIG. 11 illustrates an example of using a sensing system 4100 to monitor movement of a target 14. The sensing system 4100 may represent the sensing assembly 10 shown in FIG. 1. In FIG. 11, the sensing system 4100 may measure distances 4102 (e.g., distances 4102A, 4102B, 4102C) to the target as the target moves relative to the sensing system 4100. Motion of the target is represented by a path 4104. As shown, the target moves along a linear or substantially linear segment 4106 of the path followed by moving along a curved or substantially curved segment 4108 of the path. The curved segment 4108 may have a constant or substantially constant radius.

The sensing system 4100 (and/or an analysis system described herein) can detect movement of the target along the linear segment 4106 and then the curved segment 4108 (or vice-versa) based on changes in the distance 4102. The distance 4102 may change when the target moves along the linear segment and then remain approximately the same when the target moves along the curved segment. For example, the sensing system 4100 may measure the distance 4102 as decreasing from the distance 4102A to the distance 4102B, and then remaining the same (or substantially the same) from the distance 4102B to the distance 4102C. The sensing system 4100 (and/or the analysis system) can then determine that the target moved along the linear segment of the path and then the curved segment of the path due to these changes in the distances 4102.

Figure 12:
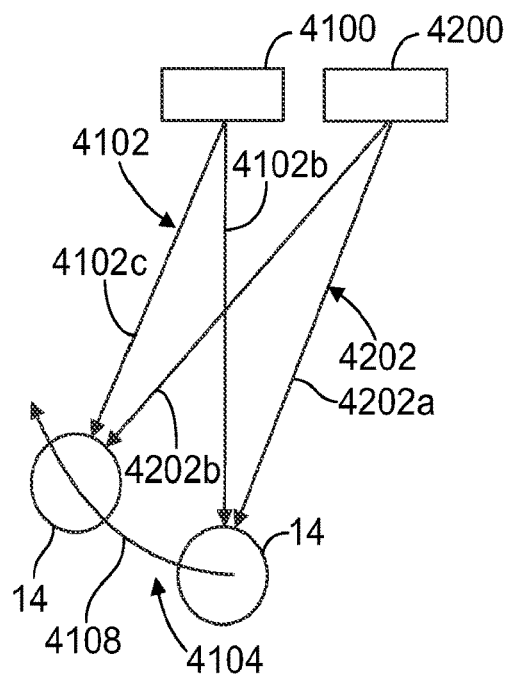
FIG. 12 illustrates an example of using plural sensing systems to monitor movement of a target.

FIG. 12 illustrates an example of using plural sensing systems 4100, 4200 to monitor movement of a target 14. The sensing system 4200 may represent another sensing assembly 10 shown in FIG. 1. In FIG. 12, the sensing system 4100 may measure distances 4102 (e.g., distances 4102B, 4102C) to the target and the sensing system 4200 may measure distances 4202 (e.g., distances 4202A, 4202B) to the target as the target moves relative to the sensing systems. Motion of the target is represented by the curved segment 4108 of the path 4104.

The sensing systems 4100, 4200 (and/or an analysis system described herein) can detect movement of the target along the curved segment 4108 based on changes in the distances 4102 and/or 4202. The distances 4102 measured by the sensing system 4100 may not change when the target moves along the curved segment of the path, as described above. But, the distances 4202 measured by the other sensing system 4200 may change during this same movement. For example, the sensing system 4200 may measure the distance 4202 as increasing from the distance 4202A to the distance 4202B. The sensing systems 4100, 4200 (and/or the analysis system) can then determine that the target moved along the curved segment of the path based on these distances 4102, 4202.

Additionally or alternatively, the analysis system may use the time record to determine acceleration and/or or an acceleration vector of the target and/or one or more target locations, such as by the second difference method or another technique. Optionally, the sensing system and/or analysis system may determine and make a time record of the motion of the target and/or one or more target locations. The analysis system can use such a time record to compute an acceleration of the target and/or one or more target locations, such as by the first difference method or another technique. Alternatively, if the sensing system and/or analysis system generates data for a time record of acceleration of the target and/or one or more target locations, then a total change in motion and/or speed of the target and/or one or more target locations may be computed, such as by a summation of the acceleration or another technique. The analysis system may then compute a total position or distance change from the computed motion. Alternatively, the total change in position or distance may be calculated directly from the acceleration, such as by the second integral method or another technique. If initial conditions or boundary conditions of the target are known to the analysis system, then the analysis system may compute the actual velocity or position of the target and/or one or more target locations.

Figure 13:
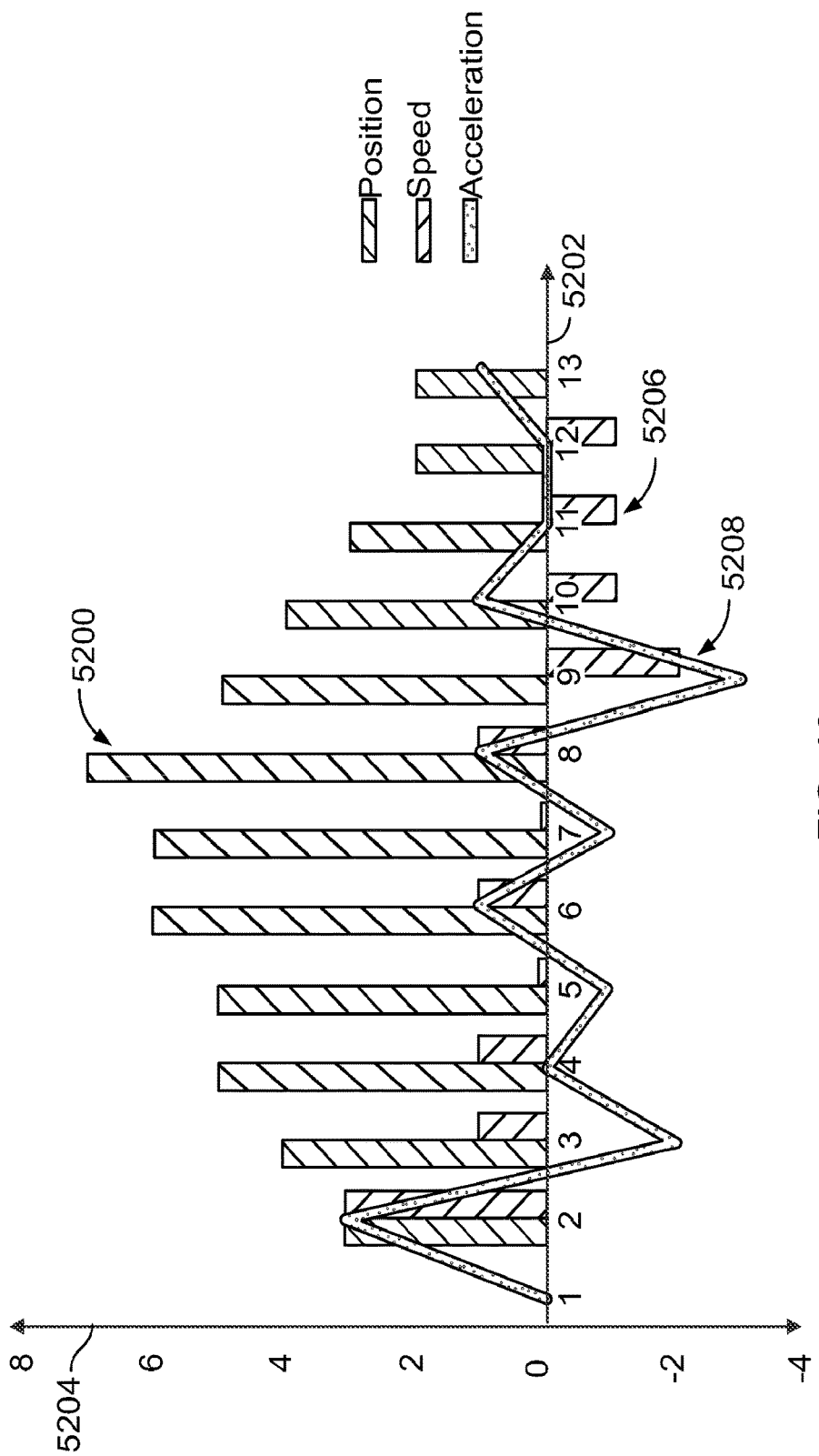
FIG. 13 illustrates data that can be obtained by the sensing system and used to compute (e.g., by the analysis system) movement parameters of the target.

FIG. 13 illustrates data that can be obtained by the sensing assembly 10 and used to compute (e.g., by the analysis system) movement parameters of the target 14. As described herein, the sensing system can measure distances to the target in order to identify position data 5200 of the target. The position data can represent the distance between the target and the sensing system or other information representative of a location of the target. The position data is shown in FIG. 13 alongside a horizontal axis 5202 representative of time and a vertical axis 5204 representative of magnitude. For example, with respect to the position data, larger values along the vertical axis can represent longer distances between the sensing system and the target, while smaller values along the vertical axis can represent shorter distances between the sensing system and the target.

The analysis system (and/or sensing system) can calculate changes in the position data with respect to time in order to determine velocity data 5206 of the target. The velocity data also is shown alongside the horizontal and vertical axes. The magnitude of the values along the vertical axis for the velocity data may represent faster or slower moving speeds of the target. The analysis system (and/or sensing system) can calculate changes in the velocity data with respect to time in order to determine acceleration data 5208 of the target. The acceleration data also is shown alongside the horizontal and vertical axes. The magnitude of the values along the vertical axis for the acceleration data may represent faster or slower changes in the moving speed of the target.

Therefore, motion or velocity and acceleration may be computed from position or distance information obtained by the sensing system. Motion or velocity and position or distance may be computed from acceleration. For example, the analysis system can integrate the acceleration data with respect to time in order to obtain the moving speed of the target, and/or can integrate the velocity data with respect to time in order to determine the position or location of the target. Position or distance can be computed from velocity or speed and acceleration may be computed from velocity or speed. There are certain limitations on these computations, as described above, but it should be understood with all the methods and devices and systems described herein that the various sources or forms of information described in this section (position/distance, motion/speed, acceleration) can be used interchangeably where appropriate.

In one aspect, the sensing system and/or analysis system may be used in place of one or more other sensors that are used to monitor vital signs (or other information) about a target, such as a human patient in a hospital or other medical facility. As described herein, data representative of movement, respiration, cardiac functions, activity, falling, and the like, may be extracted from the data obtained by the sensing system. This data may be analyzed by the analysis system to generate vital sign signals that are similar or identical to data obtained using other types of sensors. These vital sign signals from the analysis system may represent the same information and/or be indistinguishable from vital sign signals or other signals collected by other types of sensors. Consequently, the vital sign or other signals obtained and/or generated by the sensing system and/or analysis system may then be used to replace other sensors used to monitor similar information or vital signs. In this way, the sensing system and/or analysis system may be used as one or more "virtual sensors" or "virtual sensor signals" that can be used in existing systems that had previously collected the information using other means. For example, in a hospital, a patient may need to wear multiple sensors to collect various vital sign or other signals, such as signals representative of cardiac cycles, respiration, and levels of activity. As described above, the sensing system and/or analysis system can be used in lieu of or in addition to the sensors worn by the patient. The sensing system and/or analysis system can produce virtual sensor signals that can be used by a hospital's information management system, with no further change to the system, to monitor the health of many patients.

Additional information (e.g., meta data) can be captured that relates to the physical environment and orientation of the sensing system. This information can include information about the arrangement, positions, relative positions, locations, pointing directions, orientation and other physical information about the physical environment of the targets and/or other objects in the vicinity of the target, and the sensing system may be recorded as well. This can include information about the sensing system itself as well as other objects in the physical vicinity, and boundaries of the environment, such as the walls. The information can also include information about the objects, such as materials and sizes. For example, the meta data could take a written form, such as "A sensing system is mounted on the ceiling, pointed straight down at the bed, where the person's torso would normally be. There is a table near the head of the bed." The information can also be in a form usable by a computer or other logic or computation or information system. The information can also be recorded automatically, such as via one or more photographs of the environment around the sensing system. This information can be used to determine the association between a target location and another part of the target, or another object under observation. The analysis system may receive the data obtained by these other sensors and combine the data and/or compare the data with the data provided by the sensing system to determine such an association.

For example, multiple sensors (including the sensing system as a sensor) may be used in parallel to monitor and/or examine the same target. One or more of these sensors may have a limited field of view, such as in the case of a radar sensor of the sensing system, where a radar beam may only have a spread of seven degrees, or some other limited extent. Different sensors may be directed to different parts of the same target, such as by orienting multiple sensing systems toward different regions of the same target.

Instead of, or in addition to, sensing target locations that are part of the target, the sensing assembly 10 may measure distances to and/or positions of target locations of objects associated with, but not part of, a target. A target may be associated with various structures or parts, internal or external to the target, that make up the entire target. Additionally, there may be other indirect targets that have a distance or position that is related to the target, but are not part of the target. The sensing system can determine the distance, position, and/or motion of these indirect targets to extract information related to the target. For example, if a person sits in a chair and only the back of the chair is within the sensing range of the sensing system, then the sensing system and/or analysis system may sense the flex or other movement of the chair without actually sensing the person in order to determine the presence of the person in the chair. As another example, the sensing system may also sense the distance or position of blankets or clothing that is associated with a target.

Additionally or alternatively, the sensing system and/or analysis system may be used to identify individual persons and/or distinguish among persons. The analysis system can use wavelets or other signal processing techniques, pattern matching, artificial intelligence, or other methods to extract patterns of distance, position, and/or motion that are measured by the sensing system and associated with one or more target locations on of a person or animal. The parameters used to extract the vital signs for an individual person can also be used to identify the individual. For example, the analysis system can record one or more patterns of positions and/or distances or motion for a known individual person as obtained from one or more sensing systems. The one or more patterns may be unique to that individual person, or the probability of two or more individuals having matching or similar patterns may be so relatively small that the individuals can be identified using the patterns associated with the different individuals. Additionally or alternatively, the identification may be useful within a known population of individuals. The analysis system may include or have access to a set of patterns of distance and/or movement data associated with a set of individuals known to be at a given location (e.g., a nursing home). The analysis system may be unable to identify individuals outside of this set from distances and/or movement data obtained by the sensing system, but may be able to identify those individuals within the set. For example, while the identification may not be as unique as a fingerprint, but the identification may be good enough that the subject under observation is a certain person from the set of known possible subjects, for example a certain patient in a nursing home.

In one aspect, the sensing system can be hidden from view inside or behind another object. The sensing system (and associated antennas) can be designed to be tolerant of materials placed very close to the sensing system. Radio waves emitted by the sensing system (as described below) may be able to penetrate the material and allow the sensing system to operate properly, while remaining hidden from view for security, aesthetic, or other purposes. For example, a sensing system may be mounted behind a painting or other artwork hanging on a wall, with the sensing system mounted in a cavity behind the painting. As another example, the sensing system can be mounted in the ceiling of a home, with a front face of the sensing system flush with the surface of the ceiling. The sensing system could then be painted over to match the ceiling, thereby concealing the sensing system.

Figure 16:
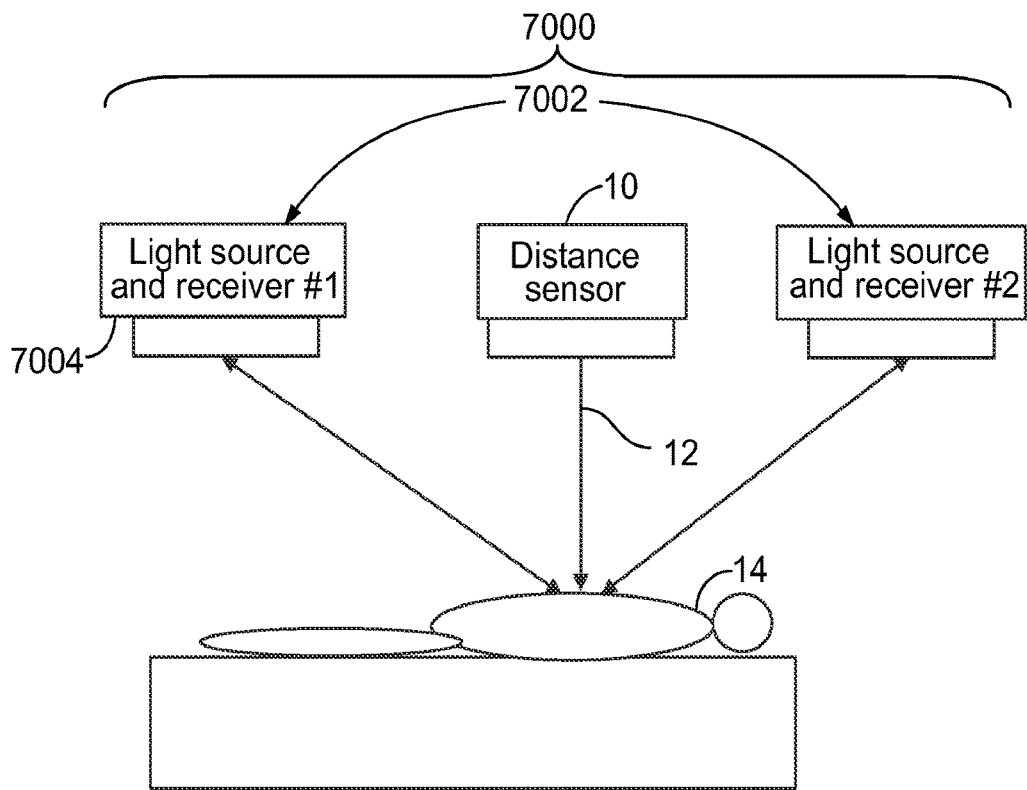
FIG. 16 illustrates an embodiment of a combination sensing system that includes the sensing system and at least one additional sensing system.

FIG. 16 illustrates an embodiment of a combination sensing system 7000 that includes the sensing assembly 10 and at least one additional sensing system 7002. The sensing system 7002 may differ from the sensing assembly 10 ("Distance sensor" in FIG. 16) in that the sensing system 7002 uses a different technique and/or medium to examine the same target 14 as the sensing assembly 10.

In the illustrated example, the sensing assembly 10 measures distance to the target or the position of a target. The target location may be the outer surface of the skin nearest to the sensing assembly 10, or somewhere else on the target, or another exposed part of the body, such as during surgery. The additional sensing system 7002 includes one or more light sources and/or optical sensors 7004, 7006. These sources and/or sensors can include light generating devices, such as lasers, that are directed toward the target to illuminate the target, such as the skin, at or near the same target location that the sensing assembly 10 is monitoring. The sources and/or sensors also can include one or more optical receivers that are sensitive to the same wavelengths of light as used in the light sources. The varying absorption and reflection of the light is measured by the optical receivers. The different magnitudes of absorption and reflection of the different wavelengths of light are affected by the amount of oxygen dissolved in the blood of the target, which may be used in a manner similar to reflective pulse oximetry.

The combination system described herein captures distance or position data at the same time as the light reflection and absorption data and can compute the amount of oxygen in the blood from a larger distance that is typically used for computing oxygen levels in blood, such as six feet (e.g., 1.8 meters) away or farther. The distance or position data obtained by the sensing assembly 10 can be used to correct or compensate for lower received optical power of the reflected light at the optical receivers due to the distance from the optical receivers to the patient or the body structure of the patient. For example, as the distance between the sensing system assembly 10 and a patient increases, a quantified amount of laser light that is reflected off the patient (e.g., a measured quantity representative of how much or how little of the laser light is received by a light sensor or meter after being reflected off the patient) may decrease due to the increased distance. Conversely, as this distance decreases, the amount of reflected light may increase. The analysis system can apply a correction factor to the measured amount of reflected light to correct for the impact of distance between the patient and the sensing system on this amount. For example, for larger distances, the analysis system can increase the amount of reflected light by an amount that is proportional to the distance. Additionally or alternatively, the analysis system can decrease the amount of reflected light by an amount that is proportional to the distance. Optionally, another technique may be used to correct the measured amount of reflected light. As a result, the corrected amount of reflected light may more accurately represent the amount of oxygen in the blood of the target object (e.g., patient).

Figure 14:
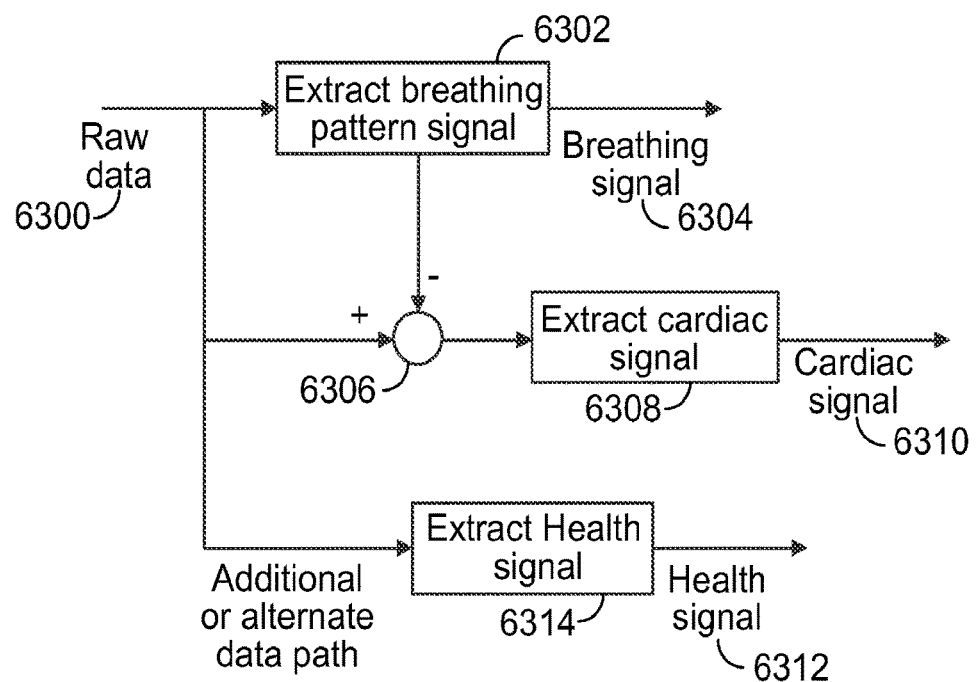
FIG. 14 illustrates an information process flow diagram that can represent the processing of data by the analysis system.

FIG. 14 illustrates an information process flow diagram that can represent the processing of data by the analysis system. The analysis system can extract or compute various signals (e.g., information) from the distance or position data obtained by the sensing system, such as vital signs or other signals of the target. Once a certain signal is isolated from data obtained by the sensing system, the isolated signal may be used to identify other signals and/or be removed from the original data stream from the sensing system so that the remaining data in the data stream can be re-processed to extract other signals that were obscured.

For example, a raw data signal 6300 may be provided to the analysis system from the sensing system. The raw data signal can include data representative of positions of a target, such as distances between the sensing system and the chest of the target. The analysis system can calculate at 6302 (e.g., extract) the motion of the chest from this data, similar to as described above in connection with FIG. 13. For example, the analysis system can calculate changes in the distance between the sensing system and the chest with respect to time, and these changes may represent a breathing pattern signal 6304 that is extracted from the raw data signal 6300. The breathing pattern signal 6304 can represent motion of the front of the chest and/or be used to reconstruct the motion of the front of the chest.

The analysis system can remove (e.g., subtract) the breathing pattern signal 6304 from the raw data signal 6300 at 6306 in FIG. 13. The removal of the breathing pattern signal 6304 from the raw data signal 6300 (and/or a subset of the raw data signal) can result in extraction (e.g., at 6308) of a cardiac signal 6310. The cardiac signal can represent motion of the heart of the patient that is not associated with or represented by the breathing of the target (e.g., the breathing pattern signal). Alternatively or additionally, the cardiac signal may be extracted directly from the raw data signal, without first computing the breathing pattern signal. For example, the raw data signal may be processed in parallel, or copies of the raw data signal may be processed in parallel by the analysis system to extract the breathing pattern signal and/or the cardiac signal in parallel, at or during the same time period, from the same raw data signal. For example, the raw data signal may be processed by the analysis system using a low-pass filter to extract the breathing pattern signal and a copy of the raw data signal may be processed by the analysis system at the same time using a wavelet transform to extract the cardiac signal. As a result, multiple signals may be extracted at the same time or in succession from one stream of raw position or distance data. Furthermore, the same signal may be extracted in multiple ways, such as directly and from processed data to gain a better estimate or measure of the signal.

Additionally or alternatively, one or more other signals of the target may be obtained from the raw data signal 6300. For example, after removing (e.g., filtering) the breathing pattern signal 6304, the cardiac signal 6310, and/or one or more other signals or portions of the raw data signal, an additional health signal 6312 may remain or be separately extracted at 6314 from the remainder of the raw data signal. This additional health data signal can represent one or more other vital signs of the target. One or more of the breathing pattern signal, the cardiac signal, and/or the additional health data signal may be output by the analysis system to one or more other systems that monitor the health or status of the target using the signal(s).

The techniques described herein can be used individually or together in any combination to enhance information collection, or gain a more comprehensive understanding of the subject, for example a person or animal. Alternatively, a subset of the techniques described herein may be used to collect or extract or compute a subset of the various signals described herein, as needed.

The techniques described herein can be used individually or in one or more combinations to extract the various signals described above, or others, including, but not limited to the presence, position or posture, activity, respiration and cardiac signals of a target, such as a person or animal. These extracted or computed signals can be used individually or in one or more combinations to assess the health of the target. The signals can be recorded over a period of time, including but not limited to, days, weeks, months, or years. These time records of the signals can then be used to extract more complex health measures or patterns. For example, a time record of data of one night while a target is sleeping can be used by the analysis system to compute the sleep health or other metrics related to the sleep of the target. If the sensing system continues to collect this nightly recording for a month (or other time period), then the analysis system can compute an overall assessment of the sleep patterns of the target. As another example, multiple sensing systems can be placed around the home of elderly or other at-risk person. The various signals from the sensing systems can be recorded over time. An initial time period can be used to establish a baseline or reference activity and vital sign pattern for the target. The sensing system and/or analysis system can then proceed with monitoring these signals for extended periods of time and look for deviations from the baseline patterns, which may indicate a change or decline in the health of the target. For example, the system can monitor these patterns over extended periods of time. If the patterns shift or decline over time then the health of the target is determined to be declining. The analysis system can notify a caregiver or other health care provider, such as a nurse, doctor, loved-one, or another system that steps should be taken to care for the subject.

The analysis system can automatically generate reports on the health or status of the target by examining the extracted or computed signals provided by the sensing system. Various algorithms may be applied to collected signals to make observations about the sleep, activities of daily living, or other health or wellness measures. The reports are then delivered to interested parties. The receiving parties may be the subject themselves to track their own health. The report recipient may also be a caregiver or doctor to track the health of the target.

The systems described herein may collect and transmit the raw distance, position, motion, and/or acceleration data of one or more target locations associated with a target, such as a person or animal. The sensing system and/or analysis system may communicate this data to another computational or electronic system for further processing, storage, and/or other purposes. The raw data may be saved for extended periods of time, or even indefinitely. At a later time, analysis that was not initially performed on the raw data may be performed. The reason that the analysis was not performed initially may be due to many factors, such as the user not paying for the analysis or the analysis simply not being necessary. Alternatively, new techniques may be developed that can use the same raw data, or new research or algorithms may emerge that can use the data. Then at any point in the future, a user or caregiver can request and/or pay for a retro-active analysis or screening of the data. Additionally another entity may request a new analysis of the data.

Alternatively or additionally, the outcomes and medical records of the subjects may be tracked or recorded. This health or medical information from one or more users can be compared to the raw data or the extracted or computed signals or vital signs or the extracted or computed health measures, such as sleep or activities of daily living. The long-term trends and patterns of all this data, across one or more users may be used to determine indications of emerging conditions in the users. For example, by comparing the data of subjects who were monitored and then had heart attacks it may come to pass that a certain breathing pattern is identified that indicates that the heart attack is imminent, such as in the next few days or weeks.

Figure 15:
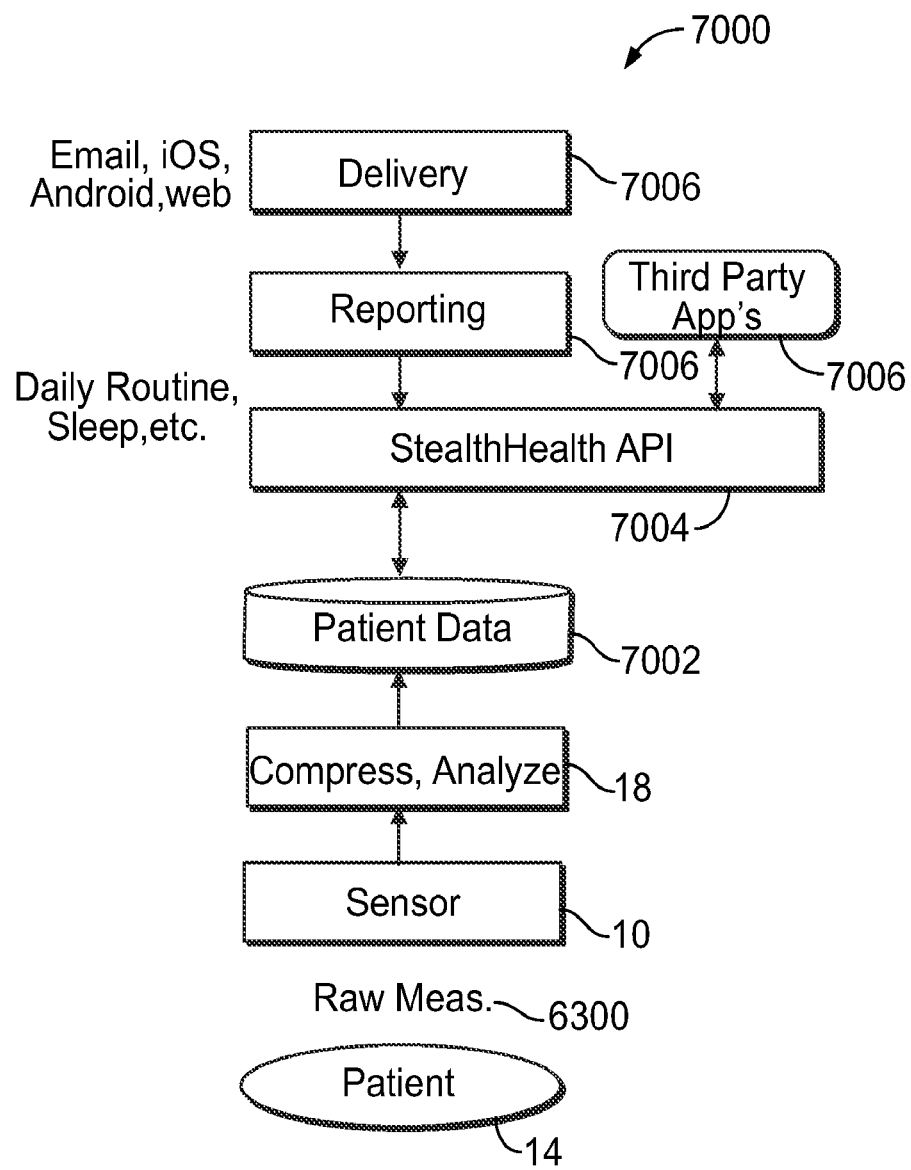
FIG. 15 illustrates a schematic diagram of an access system configured to provide third party access to data obtained by the sensing system and/or signals generated by the analysis system based on this data.

FIG. 15 illustrates a schematic diagram of an access system 7000 configured to provide third party access to data obtained by the sensing assembly 10 and/or signals generated by the analysis system 18 based on this data. The sensing system ("Sensor" in FIG. 15) may collect and transmit the raw distance, position, motion, and/or acceleration data 6300 of one or more target locations associated with a target 14, such as a person or animal. The sensing system may communicate this raw data to another computational or electronic system (e.g., the analysis system 18, shown as "Compress, Analyze" in FIG. 15) for further processing, storage, or other purposes, such as by storing the data in a tangible and non-transitory memory device 7002. Examples of such a memory device include, but are not limited to, magnetic and/or optical disks.

The raw distance or position data may be saved in the memory device for extended periods of time, or even indefinitely. One or more third-party systems or users 7006 may access the stored data, such as by using an application program interface (API) 7004. The services provided by the sensing and/or analysis system therefore can be expanded by a third-party. These third parties may access the data, signals, and/or measures described herein through the API and combine the data with other external information or know-how or methods or algorithms to perform other services for the user, subject or caregiver.

Figure 17:
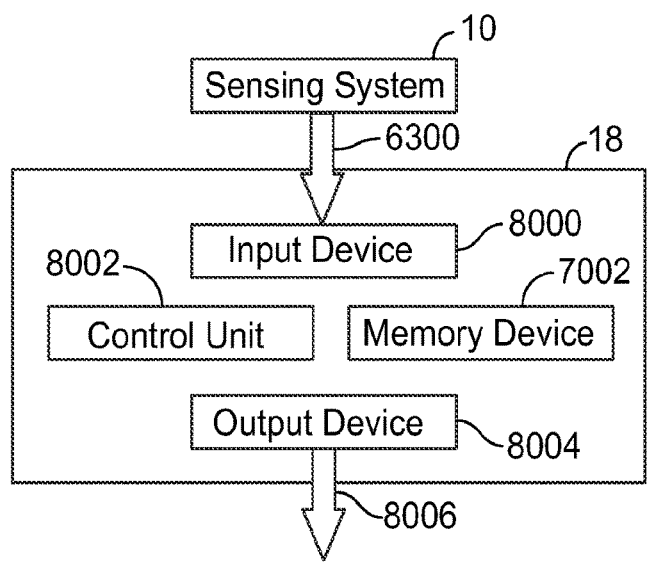
FIG. 17 is a schematic diagram of an embodiment of the analysis system.

FIG. 17 is a schematic diagram of an embodiment of the analysis system 18. The analysis system 18 includes several devices and a unit that may be embodied in one or more computer hardware assemblies, such as one or more processors, electronic circuits, memories, antennas, transceivers and associated hardware circuitry, receivers and associated hardware circuitry, and the like. An input device 8000 receives input from one or more external sources, such as the raw data signal 6300 from the sensing assembly 10, input from an operator of the input device 8000, data from one or more systems or sensors other than the sensing assembly 10, or the like. A control unit 8002 receives the input and may process and/or store the received input. For example, the control unit 8002 may store the raw data in the memory device 7002 for later examination and/or may examine the raw data as the raw data is received from the sensing system (which may include typical time delays associated with communication of the data and routing of the data to the control unit 8002. The control unit 8002 may examine the input as described herein, such as to detect presence of a target at a location (e.g., a person in a bed or chair), to monitor the posture of the target, to detect the target falling down, to monitor activity levels of the target, to track different locations of the target (e.g., a person moving around a room), to identify actual locations of the target in a location (e.g., within a room or other area having defined boundaries), to calculate the velocity and/or acceleration of movement of the target, to compare the data obtained from the sensing system with data provided by another system in order to monitor the target (e.g., for pulse oximetry or another use), to identify a target from among several potential different targets (e.g., to identify persons from different movement patterns associated with the different persons), and the like.

An output device 8004 generates one or more output signals to be communicated to other systems, persons, or the like, outside of the analysis system. For example, the control unit may generate cardiac signals, breathing pattern signals, and the like, and the output device may communicate these signals to systems outside of the analysis system. As another example, the output device may communicate data signals, an alert, or other information, to a display device in order to visually present the information obtained by the sensing system and/or examined by the analysis system.

In one aspect, the output device includes a display that visually presents any of this information or the extracted or computed signals or other health measures or vital signs to a user, or communicate the signals to another system for use elsewhere at approximately the same time. For example, the data and signals from multiple subjects in a hospital ward may all be sent to a display at a nurse's station so that they may continuously monitor the subjects or patients from a central location. The data and signals may also be saved for future use, as described above.

The sensing and/or analysis system may be used for additional applications as well. For example, the raw distance, position, motion, and/or acceleration data of one or more target locations associated with a target may be used to extract or compute signals or measures related to the health or medical condition of a subject, such as a person or animal. This data and/or the signals may be used to assess the sleep health or condition of a subject. It may be used to quantify the sleep stage of the subject, or their sleep/wake cycles, circadian rhythms, hypnogram, activity graph, or other measures of sleep. Additionally or alternatively, the data and/or the signals may be used to diagnose or screen for various sleep conditions or abnormalities such as sleep apnea, insomnia, or others.

When used to collect information about a person either with their knowledge or consent or not, the vital sign data or other data or signals can be used to determine if the person is lying or being untruthful. For example, certain breathing patterns, cardiac cycles, or other movements may be associated in the memory device with a person that is lying. The analysis system can compare the actual breathing patterns, cardiac cycles, or other movements to the known breathing patterns, cardiac cycles, or other movements that are associated with a lying person to determine if the person being monitored is lying.

As another example, the respiration of a patient or subject over time may be compared to pollen count data in their vicinity to determine if the person is allergic to various pollens, and which ones. As another example, the sleep health measure may be compared to a person's electronic calendar data to determine times or events that cause poor sleep.

As described herein, in an embodiment, a sensing system includes a first radar sensing assembly and an analysis system. The first radar sensing assembly measures plural distances to a first target location at different times using radar. The analysis system receives the plural distances from the first radar sensing assembly and quantifies movements of a target object at the first target location at the different times by calculating differences in the plural distances measured by the first radar sensing assembly. The analysis system generates one or more first quantified activity level values indicative of the movements of the target object at the first target location using the differences in the plural distances that are calculated. Optionally, the analysis system may use the distances instead of or in addition to using the differences in the distances. For example, instead of calculating changes in the distances that are measured to identify a posture, activity, fall, or other movement-related event of a person, the sensing system may measure an absolute distance to the person (e.g., the actual distance, such as 0.5 meters, 2 millimeters, 32.4562 centimeters, or other distance) and the analysis system can use this absolute distance to identify the movement or event of the person. The differences in distances may be referred to as relative distances, as the differences represent relative changes in the distances, but may not represent the absolute distances themselves.

In one aspect, the analysis system determines a posture of a human being using at least one of the plural distances or the differences in the plural distances that are measured by the radar sensing assembly. The posture includes the human at least one of standing, sitting, or lying on a surface.

In one aspect, the analysis system determines a presence of the target object at the common target location using at least one of the plural distances or the differences in the plural distances that are calculated.

In one aspect, the sensing system also includes a second radar sensing assembly measuring plural distances to a second target location at different times using radar. The second target location can be different than the first target location. The analysis system also quantifies movements of the target object at the second target location by calculating the differences in the plural distances measured by the second radar sensing assembly and generates one or more quantified second activity level values indicative of the movements of the target object at the second target location.

In one aspect, the first quantified activity level values represent the movements of a first body part of a human being and the second quantified activity level values represent the movements of a different, second body part of the same human being.

In one aspect, the analysis system detects a human being falling using the first quantified activity levels.

In one aspect, the first radar sensing assembly measures the plural distances to the first target location located on at least one of a front, side, or back of a chest of a human being and the analysis system determines a breathing pattern signal from the differences in the plural distances as the first quantified activity level values. The analysis system also may monitor respiration of the human being using the breathing pattern signal.

In one aspect, the analysis system extracts a cardiac signal from the breathing pattern signal as second quantified activity level values. The cardiac signal may represent cardiac cycles of the human being.

In one aspect, the analysis system extracts the cardiac signal as the health signal directly from the raw data signal without extracting the cardiac signal from another signal that is previously extracted from the raw data signal.

In one aspect, the target object is moving relative to the first radar sensing assembly, and the sensing system also includes a second radar sensing assembly measuring plural distances to the same first target location using radar. The analysis system tracks a movement path of the target object using the distances measured by the first radar sensing assembly and the second radar sensing assembly.

In one aspect, the analysis system at least one of stores or has access to a set of predetermined movement patterns associated with movements of plural different human beings and identifies a first human being as the target object based on the first quantified activity level values more closely matching a first predetermined movement pattern associated with the first human being than one or more other predetermined movement patterns in the set of the predetermined movement patterns.

In one aspect, the sensing system also includes one or more laser light sources generating laser light toward the first target location and one or more optical receivers detecting reflection of the laser light off the first target location. The analysis system correlates the first quantified activity level values with the reflection of the laser light in order to determine an oxygenation level of blood of the target object.

In an embodiment, a sensing method includes transmitting first electromagnetic waves toward a first target location from a first radar sensing assembly at different times, receiving first echoes of the electromagnetic waves that are reflected off the first target location using the first radar sensing assembly, measuring plural distances to the first target location using the first echoes of the electromagnetic waves, quantifying movements of a target object at the first target location at the different times by calculating differences in the plural distances measured by the first radar sensing assembly, and generating one or more first quantified activity level values indicative of the movements of the target object at the first target location using the differences in the plural distances that are calculated.

In one aspect, the sensing method also includes determining a posture of a human being using at least one of the plural distances or the differences in the plural distances that are measured by the radar sensing assembly. The posture includes the human at least one of standing, sitting, or lying on a surface.

In one aspect, the sensing method includes determining a presence of the target object at the common target location using at least one of the plural distances or the differences in the plural distances that are calculated.

In one aspect, the sensing method also includes transmitting second electromagnetic waves toward a second target location from a second radar sensing assembly. The second target location can be different than the first target location. The sensing method may further include receiving second echoes of the second electromagnetic waves that are reflected off the second target location using the second radar sensing assembly, measuring plural distances to the second target location using the second echoes of the electromagnetic waves, quantifying movements of the target object at the second target location at the different times by calculating differences in the plural distances measured by the second radar sensing assembly, quantifying movements of the target object at the second target location by calculating the differences in the plural distances measured by the second radar sensing assembly, and generating one or more quantified second activity level values indicative of the movements of the target object at the second target location.

In one aspect, the first quantified activity level values represent the movements of a first body part of a human being and the second quantified activity level values represent the movements of a different, second body part of the same human being.

In one aspect, the sensing method also includes detecting a human being falling using at least one of the first quantified activity levels or by tracking positions of one or more target locations on the target object over time.

In one aspect, the first radar sensing assembly measures the plural distances to the first target location located on a chest of a human being. The sensing method may also include determining a breathing pattern signal from the differences in the plural distances as the first quantified activity level values and monitoring respiration of the human being using the breathing pattern signal.

In one aspect, the sensing method also includes extracting a cardiac signal from the breathing pattern signal as second quantified activity level values. The cardiac signal represents cardiac cycles of the human being.

In one aspect, the method also includes extracting a health signal from the raw data signal, where the health signal includes at least one of a cardiac signal representative of cardiac cycles of the human being or another health signal.

In one aspect, the target object is moving relative to the first radar sensing assembly and the sensing method also includes transmitting second electromagnetic waves toward the same first target location from a second radar sensing assembly, receiving second echoes of the second electromagnetic waves that are reflected off the first target location using the second radar sensing assembly, measuring plural distances to the first target location using the second echoes of the electromagnetic waves, and tracking a movement path of the target object using the distances measured by the first radar sensing assembly and the second radar sensing assembly.

In one aspect, the sensing method also includes accessing a memory device that stores a set of predetermined movement patterns associated with movements of plural different human beings and identifying a first human being as the target object based on the first quantified activity level values more closely matching a first predetermined movement pattern associated with the first human being than one or more other predetermined movement patterns in the set of the predetermined movement patterns.

In one aspect, the sensing method also includes generating laser light toward the first target location from one or more laser light sources, detecting reflection of the laser light off the first target location, and correlating the first quantified activity level values with the reflection of the laser light in order to determine an oxygenation level of blood of the target object.

In one aspect, the sensing method also includes generating laser light toward the first target location from one or more laser light sources, detecting a quantified amount of reflection of the laser light off the first target location, and correcting the quantified amount of the reflection of the laser light using one or more of the plural distances that are measured in order to calculate an oxygenation level of blood in the target object.

Figure 18:
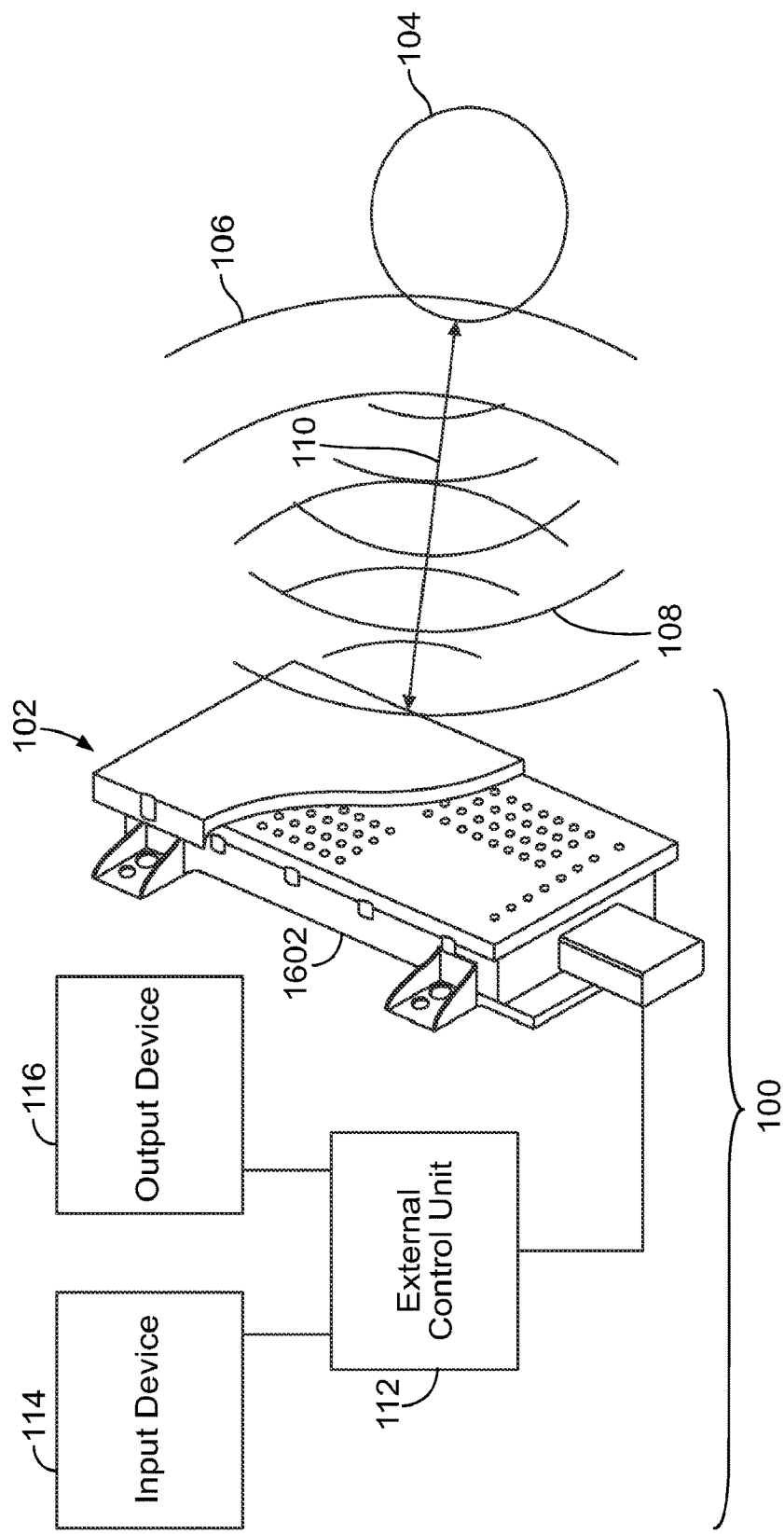
FIG. 18 is a schematic diagram of an embodiment of a sensing system.

FIG. 18 is a schematic diagram of an embodiment of a sensing system 100. The sensing system 100 can represent one or more embodiments of the sensing assembly 10 described above. The system 100 can be used in connection with one or more inventive aspects described above to determine distances between a sensing assembly 102 and one or more target objects 104 and/or to identify movement of the one or more target objects 104, where the target objects 104 may have positions that may change or that are not known. Optionally, another, different sensing system may instead be used. Additionally or alternatively, the sensing assembly 102 can represent one or more embodiments of the sensing assembly 10 described above. One or more of the target objects 104 can represent the target object 14 in one or more embodiments described above.

The sensing assembly 102 can include a radar system that transmits electromagnetic pulse sequences as transmitted signals 106 toward the target object 104 that are at least partially reflected as echoes 108. Alternatively, the sensing assembly 102 can include an optical sensing system, such as a LIght Detection And Ranging (LIDAR) system, that transmits light toward the target object 104 as the transmitted signals 106 and receives reflections of the light off the target object 104 as the echoes 108. In another embodiment, another method of transmission may be used, such as sonar, in order to transmit the transmitted signals 106 and receive the echoes 108.

A time of flight of the transmitted signals 106 and echoes 108 represents the time delay between transmission of the transmitted signals 106 and receipt of the echoes 108 off of the target object 104. The time of flight can be proportional to a distance between the sensing assembly 102 and the target object 104. The sensing assembly 102 can measure the time of flight of the transmitted signals 106 and echoes 108 and calculate a separation distance 110 between the sensing assembly 102 and the target object 104 based on the time of flight. The separation distance 110 that is measured or calculated can represent the distances between the target 14 and the sensing assembly 10 described above in one or more embodiments.

The sensing system 100 may include a control unit 112 ("External Control Unit" in FIG. 18) that directs operations of the sensing assembly 102. The control unit 112 can include one or more logic-based hardware devices, such as one or more processors, controllers, and the like. The control unit 112 shown in FIG. 18 may represent the hardware (e.g., processors, hardware circuitry, or the like) and/or logic of the hardware (e.g., one or more sets of instructions for directing operations of the hardware that is stored on a tangible and non-transitory computer readable storage medium, such as computer software stored on a computer memory). The control unit 112 can be communicatively coupled (e.g., connected so as to communicate data signals) with the sensing assembly 102 by one or more wired and/or wireless connections. The control unit 112 may be remotely located from the sensing assembly 102, such as by being disposed several meters away, in another room of a building, in another building, in another city block, in another city, in another county, state, or country (or other geographic boundary), and the like.

In one embodiment, the control unit 112 can be communicatively coupled with several sensing assemblies 102 located in the same or different places. For example, several sensing assemblies 102 that are remotely located from each other may be communicatively coupled with a common control unit 112. The control unit 112 can separately send control messages to each of the sensing assemblies 102 to individually activate (e.g., turn ON) or deactivate (e.g., turn OFF) the sensing assemblies 102. In one embodiment, the control unit 112 may direct the sensing assembly 102 to take periodic measurements of the separation distance 110 and then deactivate for an idle time to conserve power.

In one embodiment, the control unit 112 can direct the sensing assembly 102 to activate (e.g., turn ON) and/or deactivate (e.g., turn OFF) to transmit transmitted signals 106 and receive echoes 108 and/or to measure the separation distances 110. Alternatively, the control unit 112 may calculate the separation distance 110 based on the times of flight of the transmitted signals 106 and echoes 108 as measured by the sensing assembly 102 and communicated to the control unit 112. The control unit 112 can be communicatively coupled with an input device 114, such as a keyboard, electronic mouse, touchscreen, microphone, stylus, and the like, and/or an output device 116, such as a computer monitor, touchscreen (e.g., the same touchscreen as the input device 114), speaker, light, and the like. The input device 114 may receive input data from an operator, such as commands to activate or deactivate the sensing assembly 102. The output device 116 may present information to the operator, such as the separation distances 110 and/or times of flight of the transmitted signals 106 and echoes 108. The output device 116 may also connect to a communications network, such the internet.

The form factor of the sensing assembly 102 may have a wide variety of different shapes, depending on the application or use of the system 100. The sensing assembly 102 may be enclosed in a single enclosure 1602, such as an outer housing. The shape of the enclosure 1602 may depend on factors including, but not limited to, needs for power supply (e.g., batteries and/or other power connections), environmental protection, and/or other communications devices (e.g., network devices to transmit measurements or transmit/receive other communications). In the illustrated embodiment, the basic shape of the sensing assembly 102 is a rectangular box. The size of the sensing assembly 102 can be relatively small, such as three inches by six inches by two inches (7.6 centimeters by 15.2 centimeters by 5.1 centimeters), 70 mm by 140 mm by 10 mm, or another size. Alternatively, the sensing assembly 102 may have one or more other dimensions.

Figure 19:
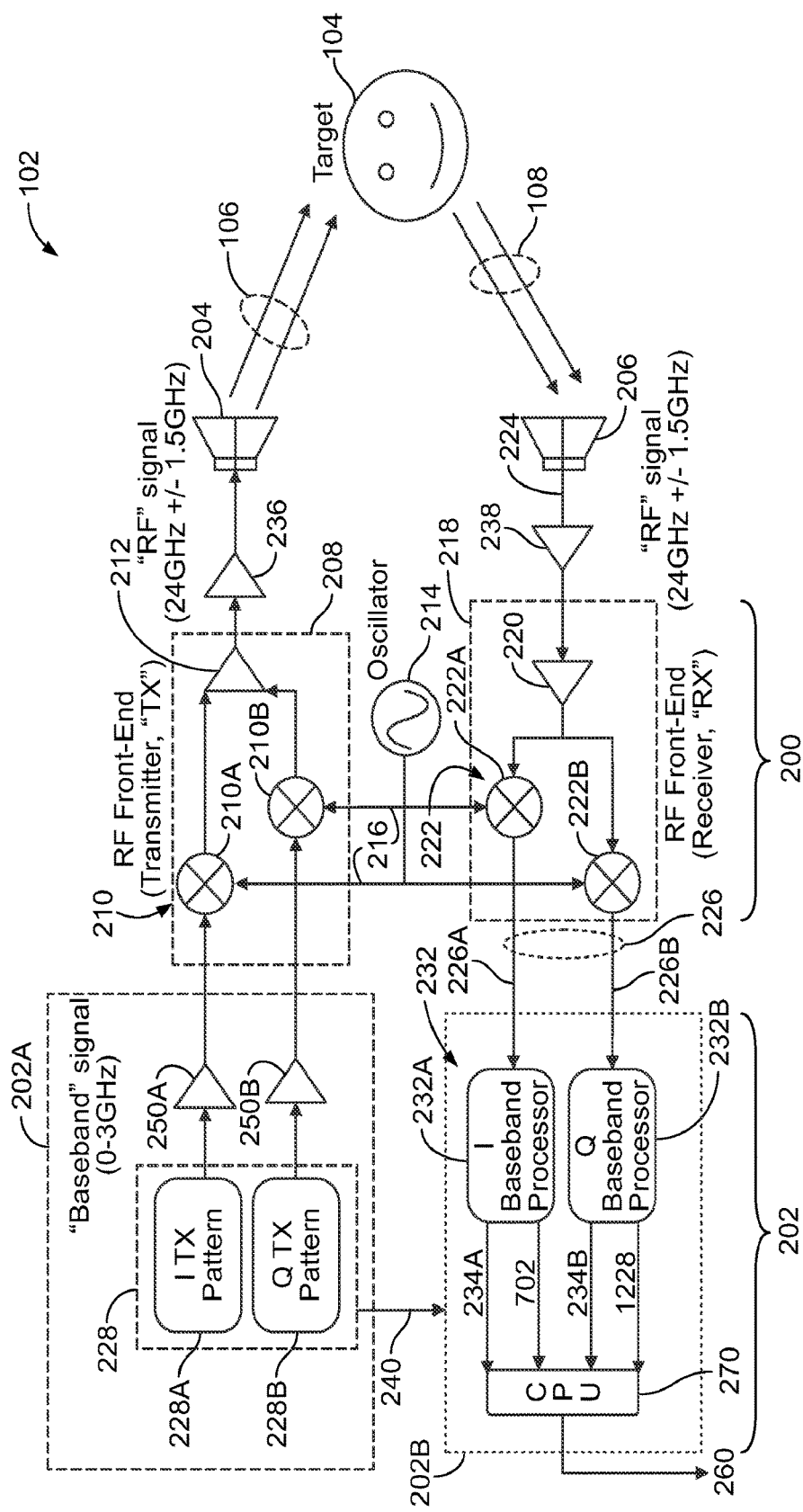
FIG. 19 is a schematic diagram of one embodiment of a sensing assembly shown in FIGS. 1 and 18.

FIG. 19 is a schematic diagram of one embodiment of the sensing assembly 102. The sensing assembly 102 may be a direct-sequence spread-spectrum radar device that uses a relatively high speed digital pulse sequence that directly modulates a carrier signal, which is then transmitted as the transmitted signals 106 toward a target object 104. The echoes 108 may be correlated to the same pulse sequence in the transmitted signals 106 in order to determine the time of flight of the transmitted signals 106 and echoes 108. This time of flight can then be used to calculate the separation distance 110 (shown in FIG. 18).

The sensing assembly 102 includes a front end 200 and a back end 202. The front end 200 may include the circuitry and/or other hardware that transmits the transmitted signals 106 and receives the reflected echoes 108. The back end 202 may include the circuitry and/or other hardware that forms the pulse sequences for the transmitted signals 106 or generates control signals that direct the front end 200 to form the pulse sequences for inclusion in the transmitted signals 106, and/or that processes (e.g., analyzes) the echoes 108 received by the front end 200. Both the front end 200 and the back end 202 may be included in a common housing. For example (and as described below), the front end 200 and the back end 202 may be relatively close to each other (e.g., within a few centimeters or meters) and/or contained in the same housing. Alternatively, the front end 200 may be remotely located from the back end 202. The components of the front end 200 and/or back end 202 are schematically shown as being connected by lines and/or arrows in FIG. 19, which may be representative of conductive connections (e.g., wires, busses, and the like) and/or wireless connections (e.g., wireless networks).

The front end 200 includes a transmitting antenna 204 and a receiving antenna 206. The transmitting antenna 204 transmits the transmitted signals 106 toward the target object 104 and the receiving antenna 206 receives the echoes 108 that are at least partially reflected by the target object 104. As one example, the transmitting antenna 204 may transmit radio frequency (RF) electromagnetic signals as the transmitted signals 106, such as RF signals having a frequency of 24 gigahertz ("GHz")±1.5 GHz. Alternatively, the transmitting antenna 204 may transmit other types of signals, such as light, and/or at another frequency. In the case of light transmission, the antenna may be replaced by a laser or LED or other device. The receiver may be replaced by a photo detector or photodiode.

A front end transmitter 208 ("RF Front-End," "Transmitter, and/or "TX" in FIG. 2) of the front end 200 is communicatively coupled with the transmitting antenna 204. The front end transmitter 208 forms and provides the transmitted signal 106 to the transmitting antenna 204 so that the transmitting antenna 204 can communicate (e.g., transmit) the transmitted signal 106. In the illustrated embodiment, the front end transmitter 208 includes mixers 210A, 210B and an amplifier 212. Alternatively, the front end transmitter 208 may not include the amplifier 212. The mixers 210A, 210B combine (e.g., modulate) a pulse sequence or pattern provided by the back end 202 with an oscillating signal 216 (e.g., a carrier signal) to form the transmitted signal 106 that is communicated by the transmitting antenna 204. In one embodiment, the mixers 210A, 210B multiply pattern signals 230A, 230B ("Baseband signal" in FIG. 19) received from one or more transmit (TX) pattern generators 228A, 228B by the oscillating signal 216. The pattern signal 230 includes the pattern formed by the pattern code generator 228. As described below, the pattern signal 230 can include several bits arranged in a known or designated sequence.

An oscillating device 214 ("Oscillator" in FIG. 19) of the front end 200 generates the oscillating signal 216 that is communicated to the mixers 210A, 210B. As one example, the oscillating device 214 may include or represent a voltage controlled oscillator (VCO) that generates the oscillating signal 216 based on a voltage signal that is input into the oscillating device 214, such as by a power source (e.g., battery) disposed in the sensing assembly 102 and/or as provided by the control unit 112 (shown in FIG. 18). The amplifier 212 may increase the strength (e.g., gain) of the transmitted signal 106.

In the illustrated embodiment, the mixer 210A receives an in-phase (I) component or channel of a pattern signal 230A and mixes the I component or channel of the pattern signal 230A with the oscillating signal 216 to form an I component or channel of the transmitted signal 106. The mixer 210B receives a quadrature (Q) component or channel of a pattern signal 230B and mixes the I component or channel of the pattern signal 230B with the oscillating signal 216 to form a Q component or channel of the transmitted signal 106.

The transmitted signal 106 (e.g., one or both of the I and Q channels) is generated when the TX baseband signal 230 flows to the mixers 210. The digital output gate 250 may be disposed between the TX pattern generator and the mixers 210 for added control of the TX baseband signal 230. After a burst of one or more transmitted signals 106 is transmitted by the transmitting antenna 204, the sensing assembly 102 may switch from a transmit mode (e.g., that involves transmission of the transmitted signals 106) to a receive mode to receive the echoes 108 off the target object 104. In one embodiment, the sensing assembly 102 may not receive or sense the echoes 108 when in the transmit mode and/or may not transmit the transmitted signals 106 when in the receive mode. When the sensing assembly 102 switches from the transmit mode to the receive mode, the digital output gate 250 can reduce the amount of time that the transmit signal 106 generated by the transmitter 208 to the point that it is eliminated (e.g., reduced to zero strength). For example, the gate 250 can include tri-state functionality and a differential highpass filter (which is represented by the gate 250). The baseband signal 230 passes through the filter before the baseband signal 230 reaches the upconversion mixer 210. The gate 250 can be communicatively coupled with, and controlled by, the control unit 112 (shown in FIG. 18) so that the control unit 112 can direct the filter of the gate 250 to enter into a tri-state (e.g., high-impedance) mode when the transmitted signal 106 (or burst of several transmitted signals 106) is transmitted and the sensing assembly 102 is to switch over to receive the echoes 108. The highpass filter across differential outputs of the gate 250 can reduce the input transmit signal 106 relatively quickly after the tri-state mode is initiated. As a result, the transmitted signal 106 is prevented from flowing to the transmitting antenna 204 and/or from leaking to the receiving antenna 206 when the sensing assembly 102 receives the echoes 108.

A front end receiver 218 ("RF Front-End," "Receiver," and/or "RX") of the front end 200 is communicatively coupled with the receiving antenna 206. The front end receiver 218 receives an echo signal 224 representative of the echoes 108 (or data representative of the echoes 108) from the receiving antenna 206. The echo signal 224 may be an analog signal in one embodiment. The receiving antenna 206 may generate the echo signal 224 based on the received echoes 108. In the illustrated embodiment, an amplifier 238 may be disposed between the receive antenna 206 and the front end receiver 218. The front end receiver 218 can include an amplifier 220 and mixers 222A, 222B. Alternatively, one or more of the amplifiers 220, 238 may not be provided. The amplifiers 220, 238 can increase the strength (e.g., gain) of the echo signal 224. The mixers 222A, 222B may include or represent one or more mixing devices that receive different components or channels of the echo signal 224 to mix with the oscillating signal 216 (or a copy of the oscillating signal 216) from the oscillating device 214. For example, the mixer 222A can combine the analog echo signal 224 and the I component of the oscillating signal 216 to extract the I component of the echo signal 224 into a first baseband echo signal 226A that is communicated to the back end 202 of the sensing assembly 102. The first baseband echo signal 226A may include the I component or channel of the baseband echo signal. The mixer 222B can combine the analog echo signal 224 and the Q component of the oscillating signal 216 to extract the Q component of the analog echo signal 224 into a second baseband echo signal 226B that is communicated to the back end 202 of the sensing assembly 102. The second baseband echo signal 226B can include the Q component or channel of the baseband echo signal. In one embodiment, the echo signals 226A, 226B can be collectively referred to as a baseband echo signal 226. In one embodiment, the mixers 222A, 222B can multiply the echo signal 224 by the I and Q components of the oscillating signal 216 to form the baseband echo signals 226A, 226B.

The back end 202 of the sensing assembly 102 includes a transmit (TX) pattern code generator 228 that generates the pattern signal 230 for inclusion in the transmitted signal 106. The transmit pattern code generator 228 includes the transmit code generators 228A, 228B. In the illustrated embodiment, the transmit code generator 228A generates the I component or channel pattern signal 230A ("I TX Pattern" in FIG. 19) while the transmit code generator 228B generates the Q component or channel pattern signal 230B ("Q TX Pattern" in FIG. 19). The transmit patterns generated by the transmit pattern code generator 228 can include a digital pulse sequence having a known or designated sequence of binary digits, or bits. A bit includes a unit of information that may have one of two values, such as a value of one or zero, high or low, ON or OFF, +1 or −1, and the like. Alternatively, a bit may be replaced by a digit, a unit of information that may have one of three or more values, and the like. The pulse sequence may be selected by an operator of the system 100 shown in FIG. 18 (such as by using the input device 114 shown in FIG. 18), may be hard-wired or programmed into the logic of the pattern code generator 228, or may otherwise be established.

The transmit pattern code generator 228 creates the pattern of bits and communicates the pattern in the pattern signals 230A, 230B to the front end transmitter 208. The pattern signals 230A, 230B may be individually or collectively referred to as a pattern signal 230. In one embodiment, the pattern signal 230 may be communicated to the front end transmitter 208 at a frequency that is no greater than 3 GHz. Alternatively, the pattern signal 230 may be communicated to the front end transmitter 208 at a greater frequency. The transmit pattern code generator 228 also communicates the pattern signal 230 to a correlator device 232 ("Correlator" in FIG. 19). For example, the pattern code generator 228 may generate a copy of the pattern signal that is sent to the correlator device 232.

The backend section 202 includes or represents hardware (e.g., one or more processors, controllers, and the like) and/or logic of the hardware (e.g., one or more sets of instructions for directing operations of the hardware that is stored on a tangible and non-transitory computer readable storage medium, such as computer software stored on a computer memory). The RX backend section 202B receives the pattern signal 230 from the pattern code generator 228 and the baseband echo signal 226 (e.g., one or more of the signals 226A, 226B) from the front end receiver 200. The RX backend section 202B may perform one or more stages of analysis of the baseband echo signal 226 in order to determine the separation distance 110 and/or to track and/or detect movement of the target object 104.

The stages of analysis can include a coarse stage, a fine stage, and/or an ultrafine stage, as described above. In the coarse stage, the baseband processor 232 compares the pattern signal 230 with the baseband echo signal 226 to determine a coarse or estimated time of flight of the transmitted signals 106 and the echoes 108. For example, the baseband processor 232 can measure a time delay of interest between the time when a transmitted signal 106 is transmitted and a subsequent time when the pattern in the pattern signal 230 (or a portion thereof) and the baseband echo signal 226 match or substantially match each other, as described below. The time delay of interest may be used as an estimate of the time of flight of the transmitted signal 106 and corresponding echo 108.

In the fine stage, the sensing assembly 102 can compare a replicated copy of the pattern signal 230 with the baseband echo signal 226. The replicated copy of the pattern signal 230 may be a signal that includes the pattern signal 230 delayed by the time delay of interest measured during the coarse stage. The sensing assembly 102 compares the replicated copy of the pattern signal 230 with the baseband echo signal 226 to determine a temporal amount or degree of overlap or mismatch between the replicated pattern signal and the baseband echo signal 226. This temporal overlap or mismatch can represent an additional portion of the time of flight that can be added to the time of flight calculated from the coarse stage. In one embodiment, the fine stage examines I and/or Q components of the baseband echo signal 226 and the replicated pattern signal.

In the ultrafine stage, the sensing assembly 102 also can examine the I and/or Q component of the baseband echo signal 226 and the replicated pattern signal to determine a temporal overlap or mismatch between the I and/or Q components of the baseband echo signal 226 and the replicated pattern signal. The temporal overlap or mismatch of the Q components of the baseband echo signal 226 and the replicated pattern signal may represent an additional time delay that can be added to the time of flight calculated from the coarse stage and the fine stage (e.g., by examining the I and/or Q components) to determine a relatively accurate estimation of the time of flight. Alternatively or additionally, the ultrafine stage may be used to precisely track and/or detect movement of the target object 104 within the bit of interest. The terms "fine" and "ultrafine" are used to mean that the fine stage may provide a more accurate and/or precise (e.g., greater resolution) calculation of the time of flight ($t_F$) and/or the separation distance 110 relative to the coarse stage and that the ultrafine stage may provide a more accurate and/or precise (e.g., greater resolution) calculation of the time of flight ($t_F$) and/or the separation distance 110 relative to the fine stage and the coarse stage. Alternatively or additionally, the time lag of the waveforms in the I channel and Q channel can be examined to resolve phases of the echoes in order to calculate separation distance or motion of the target.

As described above, the ultrafine stage determination may involve a similar process as the coarse stage determination. For example, the coarse stage determination may examine the I channel of the receive pattern and the data stream to determine correlation values of different subsets of the data stream and, from those correlation values, determine a subset of interest and a corresponding time-of-flight, as described herein. The ultrafine stage determination can use the I and/or Q channel of the receive pattern and the data stream to determine correlation values of different subsets of the data stream and, from those correlation values, determine a subset of interest and a time-of-flight. The times-of-flight from the I channel and Q channel can be combined (e.g., averaged) to calculate a time of flight and/or separation distance to the target. The correlation values calculated by the ultrafine stage determination can be used to calculate an additional time delay that can be added to the time delays from the coarse stage and/or the fine stage to determine a time of flight and/or separation distance to the target. Alternatively or additionally, the correlation values of the waveforms in the I channel and Q channel can be examined to resolve phases of the echoes in order to calculate separation distance or motion of the target.

The backend 202 can include a first baseband processor 232A ("I Baseband Processor" in FIG. 2) and a second baseband processor 232B ("Q Baseband Processor" in FIG. 2). The first baseband processor 232A may examine the I component or channel of the echo signal 226A and the second baseband processor 232B may examine the Q component or channel of the echo signal 226B. The backend 202 can provide a measurement signal 234 as an output from the analysis of the baseband echo signal 226. In one embodiment, the measurement signal 234 includes an I component or channel measurement signal 234A from the first baseband processor 232A and a Q component or channel measurement signal 234B from the second baseband processor 232B. The measurement signal 234 may include the separation distance 110 and/or the time of flight. The total position estimate 260 can be communicated to the control unit 112 (shown in FIG. 1) so that the control unit 112 can use data or information representative of the separation distance 110 and/or the time of flight for one or more other uses, calculations, and the like, and/or for presentation to an operator on the output device 116 (shown in FIG. 18).

As described below, a correlation window that also includes the pattern (e.g., the pulse sequence of bits) or a portion thereof that was transmitted in the transmitted signal 106 may be compared to the baseband echo signal 226. The correlation window may be progressively shifted or delayed from a location in the baseband echo signal 226 representative of a start of the echo signal 226 (e.g., a time that corresponds to the time at which the transmitted signal 106 is transmitted, but which may or may not be the exact beginning of the baseband echo signal) and successively, or in any other order, compared to different subsets or portions of the baseband echo signal 226. Correlation values representative of degrees of match between the pulse sequence in the correlation window and the subsets or portions of the baseband echo signal 226 can be calculated and a time delay of interest (e.g., approximately the time of flight) can be determined based on the time difference between the start of the baseband echo signal 226 and one or more maximum or relatively large correlation values. The maximum or relatively large correlation value may represent at least partial reflection of the transmitted signals 106 off the target object 104, and may be referred to as a correlation value of interest.

As used herein, the terms "maximum," "minimum," and forms thereof, are not limited to absolute largest and smallest values, respectively. For example, while a "maximum" correlation value can include the largest possible correlation value, the "maximum" correlation value also can include a correlation value that is larger than one or more other correlation values, but is not necessarily the largest possible correlation value that can be obtained. Similarly, while a "minimum" correlation value can include the smallest possible correlation value, the "minimum" correlation value also can include a correlation value that is smaller than one or more other correlation values, but is not necessarily the smallest possible correlation value that can be obtained.

The time delay of interest can then be used to calculate the separation distance 110 from the coarse stage. For example, in one embodiment, the separation distance 110 may be estimated or calculated as:

$$d = \frac{t_F \times c}{2} \quad \text{(Equation \#1)}$$

where d represents the separation distance 110, $t_F$ represents the time delay of interest (calculated from the start of the baseband echo signal 226 to the identification of the correlation value of interest), and c represents the speed of light. Alternatively, c may represent the speed at which the transmitted signals 106 and/or echoes 108 move through the medium or media between the sensing assembly 102 and the target object 104. In another embodiment, the value of $t_F$ and/or c may be modified by a calibration factor or other factor in order to account for portions of the delay between transmission of the transmitted signals 106 and receipt of the echoes 108 that are not due to the time of flight of the transmitted signals 106 and/or echoes 108.

Figure 20:
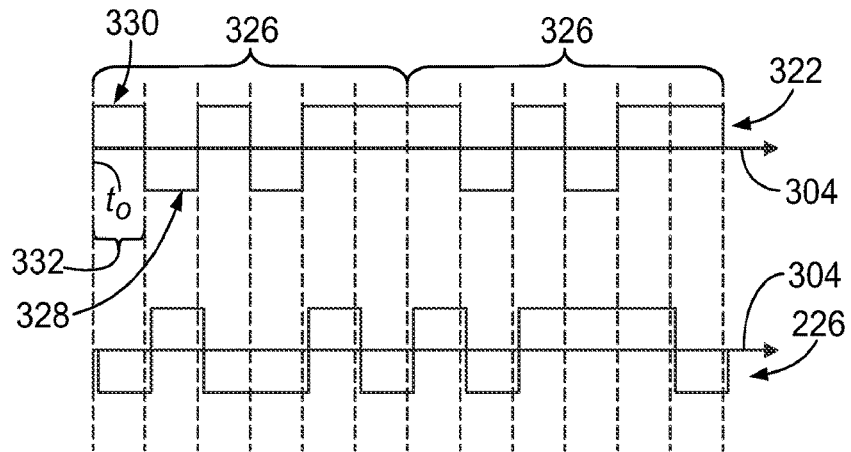
FIG. 20 is a schematic diagram of a coarse stage determination of a time of flight for a transmitted signal and corresponding echo in accordance with one embodiment.
Figure 21:
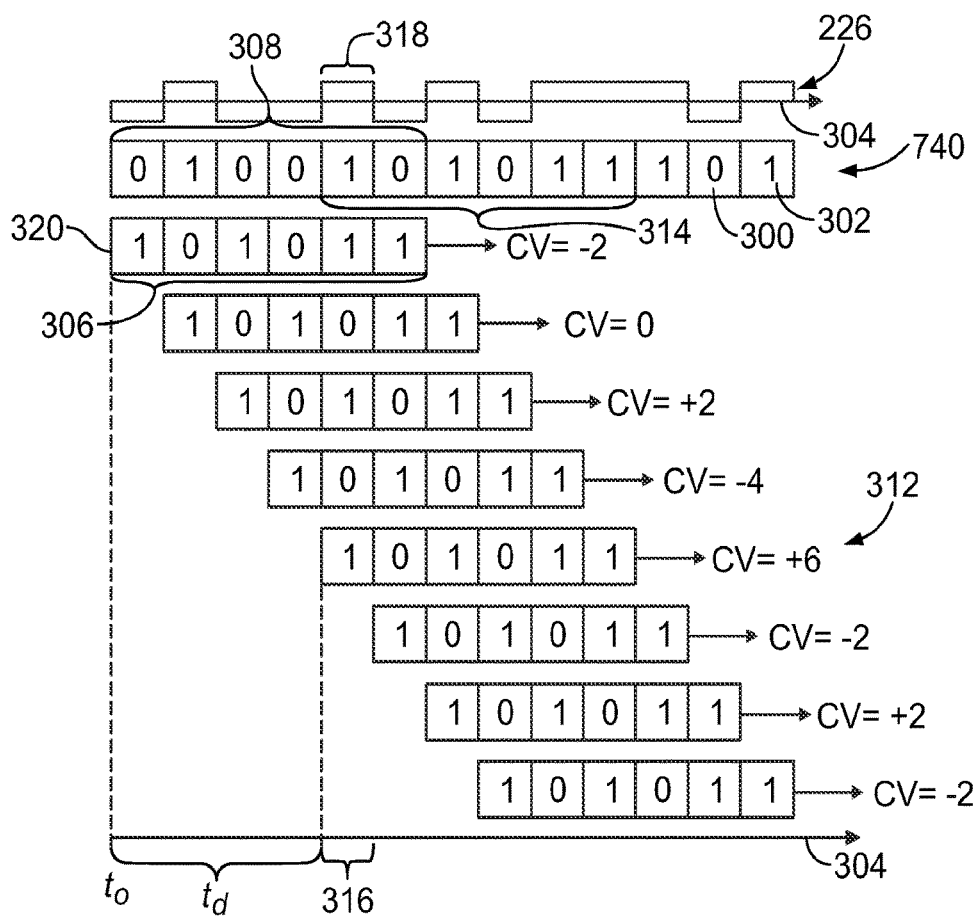
FIG. 21 is another schematic diagram of the coarse stage determination of a time of flight for a transmitted signal and corresponding echo in accordance with one embodiment.

With continued reference to the sensing assembly 102 shown in FIG. 19, FIGS. 20 and 21 are schematic diagrams of a coarse stage determination of a time of flight for a transmitted signal 106 and corresponding echo 108 in accordance with one embodiment. By "coarse," it is meant that one or more additional measurements or analyses of the same or different echo signal 224 (shown in FIG. 19) that is generated from the reflected echoes 108 may be performed to provide a more accurate and/or precise measurement of the time of flight ($t_F$) and/or separation distance 110. The use of the term "coarse" is not intended to mean that the measurement technique described above is inaccurate or imprecise. As described above, the pattern generated by the pattern code generator 228 and the baseband echo signal 226 are received by the RX backend 202B. The baseband echo signal 226 can be formed by mixing (e.g., multiplying) the echo signal 224 by the oscillating signal 216 in order to translate the echo signal 224 into a baseband signal.

FIG. 20 illustrates a square waveform transmitted signal 322 representative of the transmitted signal 106 (shown in FIG. 18) and the digitized echo signal 226. The echo signal 226 shown in FIG. 20 may represent the I component or channel of the echo signal 226 (e.g., the signal 226A). The signals 322, 226 are shown alongside horizontal axes 304 representative of time. The transmitted signal 322 includes pattern waveform segments 326 that represent the pattern that is included in the transmitted signal 106. In the illustrated embodiment, the pattern waveform segments 326 correspond to a bit pattern of 101011, where 0 represents a low value 328 of the transmitted signal 322 and 1 represents a high value 330 of the transmitted signal 322. Each of the low or high values 328, 330 occurs over a bit time 332. In the illustrated embodiment, each pattern waveform segment 326 includes six bits (e.g., six 0s and 1s), such that each pattern waveform segment 326 extends over six bit times 332. Alternatively, one or more of the pattern waveform segments 326 may include a different sequence of low or high values 328, 330 and/or occur over a different number of bit times 332.

The baseband echo signal 226 includes in one embodiment a sequence of square waves (e.g., low and high values 328, 330), but the waves may have other shapes. The echo signal 226 may be represented as a digital echo signal 740 (shown and described below in connection with FIG. 21). As described below, different portions or subsets of the digital echo signal 740 can be compared to the pattern sequence of the transmitted signal 106 (e.g., the pattern waveform segments 326) to determine a time delay of interest, or estimated time of flight. As shown in FIG. 20, the square waves (e.g., low and high values 328, 330) of the baseband echo signal 226 may not exactly line up with the bit times 332 of the transmitted signal 322.

FIG. 21 illustrates the digitized echo signal 740 of FIG. 20 along the axis 304 that is representative of time. As shown in FIG. 21, the digitized echo signal 740 may be schematically shown as a sequence of bits 300, 302. Each bit 300, 302 in the digitized echo signal 740 can represent a different low or high value 328, 330 (shown in FIG. 20) of the digitized echo signal 740. For example, the bit 300 (e.g., "0") can represent low values 328 of the digitized echo signal 740 and the bit 302 (e.g., "1") can represent high values 330 of the digitized echo signal 740.

The baseband echo signal 226 begins at a transmission time ($t_0$) of the axis 304. The transmission time ($t_0$) may correspond to the time at which the transmitted signal 106 is transmitted by the sensing assembly 102. Alternatively, the transmission time ($t_0$) may be another time that occurs prior to or after the time at which the transmitted signal 106 is transmitted.

The baseband processor 232 obtains a receive pattern signal 240 from the pattern generator 228, similar to the transmit pattern (e.g., in the signal 230) that is included in the transmitted signal 106, the receive pattern signal 240 may include a waveform signal representing a sequence of bits, such as a digital pulse sequence receive pattern 306 shown in FIGS. 20 and 21. The baseband processor 232 compares the receive pattern 306 to the echo signal 226. In one embodiment, the receive pattern 306 is a copy of the transmit pattern of bits that is included in the transmitted signal 106 from the pattern code generator 228, as described above. Alternatively, the receive pattern 306 may be different from the transmit pattern that is included in the transmitted signal 106. For example, the receive pattern 306 may have a different sequence of bits (e.g., have one or more different waveforms that represent a different sequence of bits) and/or have a longer or shorter sequence of bits than the transmit pattern. The receive pattern 306 may be represented by one or more of the pattern waveform segments 326, or a portion thereof, shown in FIG. 20.

The baseband processor 232 uses all or a portion of the receive pattern 306 as a correlation window 320 that is compared to different portions of the digitized echo signal 740 in order to calculate correlation values ("CV") at the different positions. The correlation values represent different degrees of match between the receive pattern 306 and the digitized echo signal 740 across different subsets of the bits in the digitized echo signal 740. In the example illustrated in FIGS. 20 and 21, the correlation window 320 includes six bits 300, 302. Alternatively, the correlation window 320 may include a different number of bits 300, 302. The correlator device 731 can temporally shift the correlation window 320 along the echo signal 740 in order to identify where (e.g., which subset of the echo signal 226) more closely matches the pattern in the correlation window 320 more than one or more (or all) of the other portions of the echo signal 740. In one embodiment, when operating in the coarse stage determination, the first baseband processor 232A compares the correlation window 320 to the I component or channel of the echo signal 226.

For example, the correlator device 731 may compare the bits in the correlation window 320 to a first subset 308 of the bits 300, 302 in the digitized echo signal 740. For example, the correlator device 731 can compare the receive pattern 306 with the first six bits 300, 302 of the digitized echo signal 740. Alternatively, the correlator device 731 can begin by comparing the receive pattern 306 with a different subset of the digitized echo signal 740. The correlator device 731 calculates a first correlation value for the first subset 308 of bits in the digitized echo signal 740 by determining how closely the sequence of bits 300, 302 in the first subset 308 match the sequence of bits 300, 302 in the receive pattern 306.

In one embodiment, the correlator device 731 assigns a first value (e.g., +1) to those bits 300, 302 in the subset of the digitized echo signal 740 being compared to the correlation window 320 that match the sequence of bits 300, 302 in the correlation window 320 and a different, second value (e.g., −1) to those bits 300, 302 in the subset of the digitized echo signal 740 being examined that do not match the sequence of bits 300, 302 in the correlation window 320. Alternatively, other values may be used. The correlator device 731 may then sum these assigned values for the subset of the digitized echo signal 740 to derive a correlation value for the subset.

With respect to the first subset 308 of bits in the digitized echo signal, only the fourth bit (e.g., zero) and the fifth bit (e.g., one) match the fourth bit and the fifth bit in the correlation window 320. The remaining four bits in the first subset 308 do not match the corresponding bits in the correlation window 320. As a result, if +1 is assigned to the matching bits and −1 is assigned to the mismatching bits, then the correlation value for the first subset 308 of the digitized echo signal 740 is calculated to be −2. On the other hand, if +1 is assigned to the bits and 0 is assigned to the mismatching bits, then the correlation value for the first subset 308 of the digitized echo signal 740 is calculated to be +2. As described above, other values may be used instead of +1 and/or −1.

The correlator device 731 then shifts the correlation window 320 by comparing the sequence of bits 300, 302 in the correlation window 320 to another (e.g., later or subsequent) subset of the digitized echo signal 740. In the illustrated embodiment, the correlator device 731 compares the correlation window 320 to the sixth through seventh bits 300, 302 in the digitized echo signal 740 to calculate another correlation value. As shown in FIGS. 20 and 21, the subsets to which the correlation window 320 is compared may at least partially overlap with each other. For example, each of the subsets to which the correlation window 320 is compared may overlap with each other by all but one of the bits in each subset. In another example, each of the subsets may overlap with each other by a fewer number of the bits in each subset, or even not at all.

The correlator device 731 may continue to compare the correlation window 320 to different subsets of the digitized echo signal 740 to calculate correlation values for the subsets. In continuing with the above example, the correlator device 731 calculates the correlation values shown in FIGS. 20 and 21 for the different subsets of the digitized echo signal 740. In FIGS. 20 and 21, the correlation window 320 is shown shifted below the subset to which the correlation window 320 is compared, with the correlation value of the subset to which the correlation window 320 is compared shown to the right of the correlation window 320 (using values of +1 for matches and −1 for mismatches). As shown in the illustrated example, the correlation value associated with the fifth through tenth bits 300, 302 in the digitized echo signal 226 has a correlation value (e.g., +6) that is larger than one or more other correlation values of the other subsets, or that is the largest of the correlation values.

In another embodiment, the receive pattern 306 that is included in the correlation window 320 and that is compared to the subsets of the digitized echo signal 740 may include a portion, and less than the entirety, of the transmit pattern that is included in the transmitted signal 106 (shown in FIG. 18). For example, if the transmit pattern in the transmitted signal 106 includes a waveform representative of a digital pulse sequence of thirteen (or a different number) of bits 300, 302, the correlator device 731 may use a receive pattern 306 that includes less than thirteen (or a different number) of the bits 300, 302 included in the transmit pattern.

In one embodiment, the correlator device 731 can compare less than the entire receive pattern 306 to the subsets by applying a mask to the receive pattern 306 to form the correlation window 320 (also referred to as a masked receive pattern). With respect to the receive pattern 306 shown in FIGS. 20 and 21, the correlator device 731 may apply a mask comprising the sequence "000111" (or another mask) to the receive pattern 306 to eliminate the first three bits 300, 302 from the receive pattern 306 such that only the last three bits 300, 302 are compared to the various subsets of the digitized echo signal 740. The mask may be applied by multiplying each bit in the mask by the corresponding bit in the receive pattern 306. In one embodiment, the same mask also is applied to each of the subsets in the digitized echo signal 740 when the correlation window 320 is compared to the subsets.

The correlator 731 may identify a correlation value that is largest, that is larger than one or more correlation values, and/or that is larger than a designated threshold as a correlation value of interest 312. In the illustrated example, the fifth correlation value (e.g., +6) may be the correlation value of interest 312. The subset or subsets of bits in the digitized echo signal 740 that correspond to the correlation value of interest 312 may be identified as the subset or subsets of interest 314. In the illustrated example, the subset of interest 314 includes the fifth through tenth bits 300, 302 in the digitized echo signal 740. In this example, if the start of the subset of interest is used to identify the subset of interest then the delay of interest would be five. Multiple subsets of interest may be identified where the transmitted signals 106 (shown in FIG. 18) are reflected off of multiple target objects 104 (shown in FIG. 18), such as different target objects 104 located different separation distances 110 from the sensing assembly 102.

Each of the subsets of the digitized echo signal 740 may be associated with a time delay ($t_d$) between the start of the digitized echo signal 740 (e.g., $t_0$) and the beginning of the first bit in each subset of the digitized echo signal 740. Alternatively, the beginning of the time delay ($t_d$) for the subset can be measured from another starting time (e.g., a time before or after the start of the digitized echo signal 740 ($t_0$) and/or the end of the time delay ($t_d$) may be at another location in the subset, such as the middle or at another bit of the subset.

The time delay ($t_d$) associated with the subset of interest may represent the time of flight ($t_F$) of the transmitted signal 106 that is reflected off a target object 104. Using Equation #1 above, the time of flight can be used to calculate the separation distance 110 between the sensing assembly 102 and the target object 104. In one embodiment, the time of flight ($t_F$) may be based on a modified time delay ($t_d$), such as a time delay that is modified by a calibration factor to obtain the time of flight ($t_F$). As one example, the time of flight ($t_F$) can be corrected to account for propagation of signals and/or other processing or analysis. Propagation of the echo signal 224, formation of the baseband echo signal 226, propagation of the baseband echo signal 226, and the like, through the components of the sensing assembly 102 can impact the calculation of the time of flight ($t_F$). The time delay associated with a subset of interest in the baseband echo signal 226 may include the time of flight of the transmitted signals 106 and echoes 108, and also may include the time of propagation of various signals in the analog and digital blocks (e.g., the correlator device 731 and/or the pattern code generator 228 and/or the mixers 210 and/or the amplifier 238) of the system 100.

In order to determine the propagation time of data and signals through these components, a calibration routine can be employed. A measurement can be made to a target of known distance. For example, one or more transmitted signals 106 can be sent to the target object 104 that is at a known separation distance 110 from the transmit and/or receiving antennas 204, 206. The calculation of the time of flight for the transmitted signals 106 can be made as described above, and the time of flight can be used to determine a calculated separation distance 110. Based on the difference between the actual, known separation distance 110 and the calculated separation distance 110, a measurement error that is based on the propagation time through the components of the sensing assembly 102 may be calculated. This propagation time may then be used to correct (e.g., shorten) further times of flight that are calculated using the sensing assembly 102.

In one embodiment, the sensing assembly 102 may transmit several bursts of the transmitted signal 106 and the correlator device 731 may calculate several correlation values for the digitized echo signals 740 that are based on the reflected echoes 108 of the transmitted signals 106. The correlation values for the several transmitted signals 106 may be grouped by common time delays ($t_d$), such as by calculating the average, median, or other statistical measure of the correlation values calculated for the same or approximately the same time delays ($t_d$). The grouped correlation values that are larger than other correlation values or that are the largest may be used to more accurately calculate the time of flight ($t_F$) and separation distance 110 relative to using only a single correlation value and/or burst.

Figure 22:
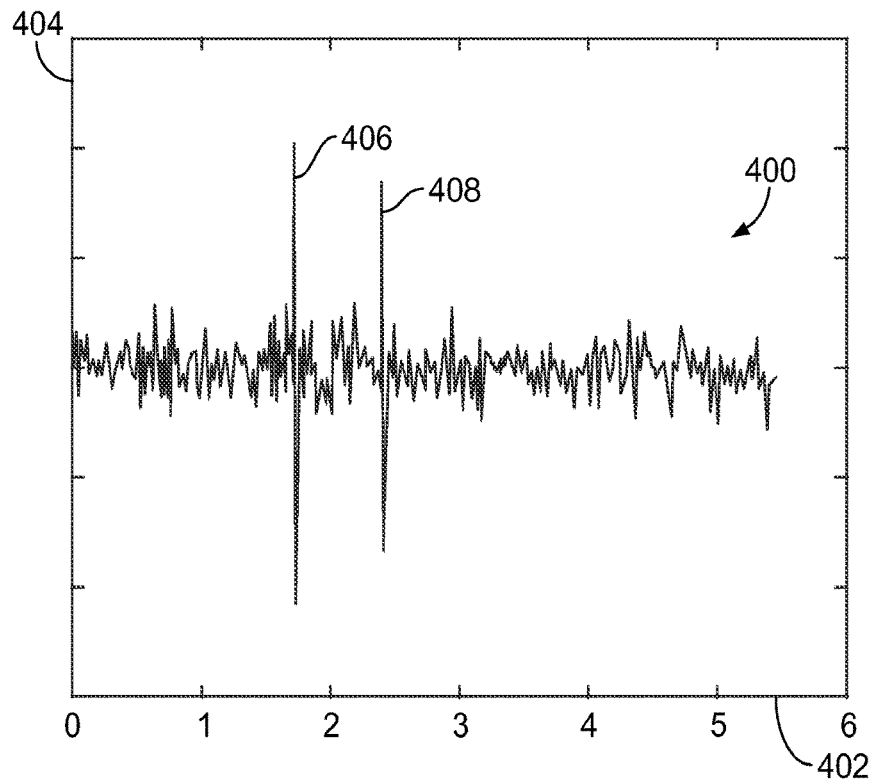
FIG. 22 illustrates one example of correlation values that are calculated and averaged over several transmitted signals shown in FIG. 18.

FIG. 22 illustrates one example of correlation values that are calculated and averaged over several transmitted signals 106 shown in FIG. 18. The correlation values 400 are shown alongside a horizontal axis 402 representative of time (e.g., time delays or times of flight) and a vertical axis 404 representative of the magnitude of the correlation values 400. As shown in FIG. 22, several peaks 406, 408 may be identified based on the multiple correlation values 400 that are grouped over several transmitted signals 106. The peaks 406, 408 may be associated with one or more target objects 104 (shown in FIG. 18) off which the transmitted signals 106 reflected. The time delays associated with one or more of the peaks 406, 408 (e.g., the time along the horizontal axis 402) can be used to calculate the separation distance(s) 110 of one or more of the target objects 104 associated with the peaks 406, 408, as described above.

Figure 23:
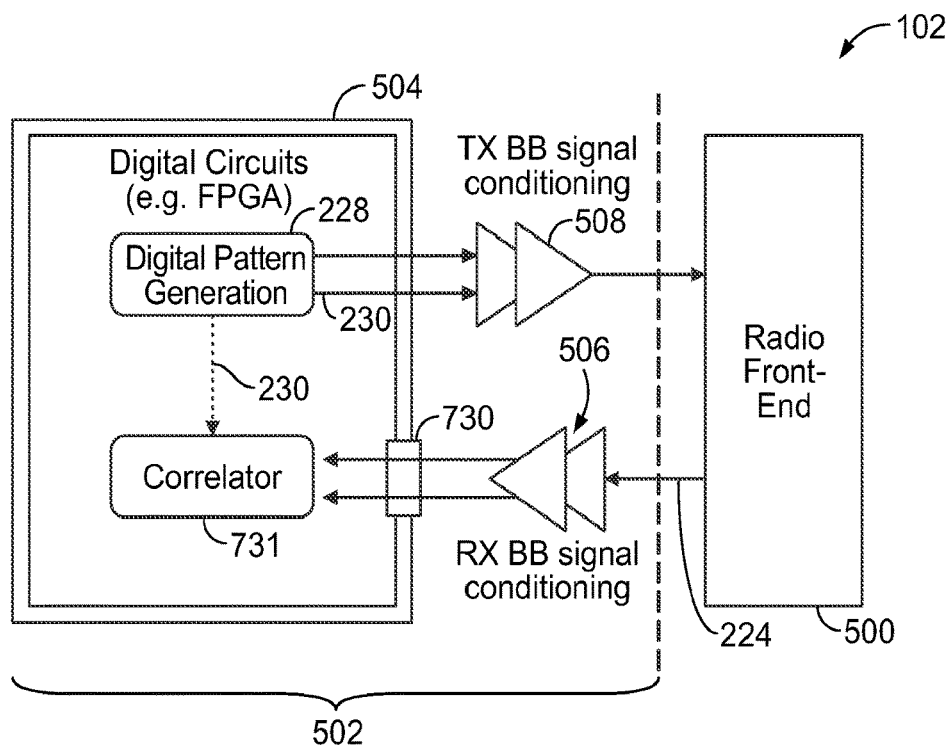
FIG. 23 is another schematic diagram of part or one implementation of the sensing assembly shown in FIG. 19.

FIG. 23 is another schematic diagram of the sensing assembly 102 shown in FIG. 19. The sensing assembly 102 is illustrated in FIG. 23 as including a radio front end 500 and a processing back end 502. The radio front end 500 may include at least some of the components included in the front end 200 (shown in FIG. 19) of the sensing assembly 102 and the processing back end 502 may include at least some of the components of the back end 202 (shown in FIG. 19) of the sensing assembly 102, and/or one or more components (e.g., the front end transmitter 208 and/or receiver 218 shown in FIG. 19) of the front end 200.

As described above, the received echo signal 224 may be conditioned by circuits 506 (e.g., by the front end receiver 218 shown in FIG. 19) that are used for high-speed optical communications systems in one embodiment. This conditioning may include amplification and/or quantization only. The signal 224 may then pass to a digitizer 730 that creates a digital signal based on the signal 224, which is then passed to the correlator 731 (described below) for comparison to the original transmit sequence to extract time-of-flight information. The correlator device 731 and the conditioning circuits may be collectively referred to as the baseband processing section of the sensing assembly 102.

Also as described above, the pattern code generator 228 generates the pattern (e.g., a digital pulse sequence) that is communicated in the pattern signal 230. The digital pulse sequence may be relatively high speed in order to make the pulses shorter and increase accuracy and/or precision of the system 100 (shown in FIG. 18) and/or to spread the transmitted radio energy over a very wide band. If the pulses are sufficiently short enough, the bandwidth may be wide enough to be classified as Ultra-wideband (UWB). As a result, the system 100 can be operated in the 22-27 GHz UWB band and/or the 3-10 GHz UWB band that are available worldwide (with regional variations) for unlicensed operation.

In one embodiment, the digital pulse sequence is generated by one or more digital circuits, such as a relatively low-power Field-Programmable Gate Array (FPGA) 504. The FPGA 504 may be an integrated circuit designed to be configured by the customer or designer after manufacturing to implement a digital or logical system. As shown in FIG. 23, the FPGA 504 can be configured to perform the functions of the pulse code generator 228 and the correlator device 731. The pulse sequence can be buffered and/or conditioned by one or more circuits 508 and then passed directly to the transmit radio of the front end 500 (e.g., the front end transmitter 208).

Figures 24, 25:
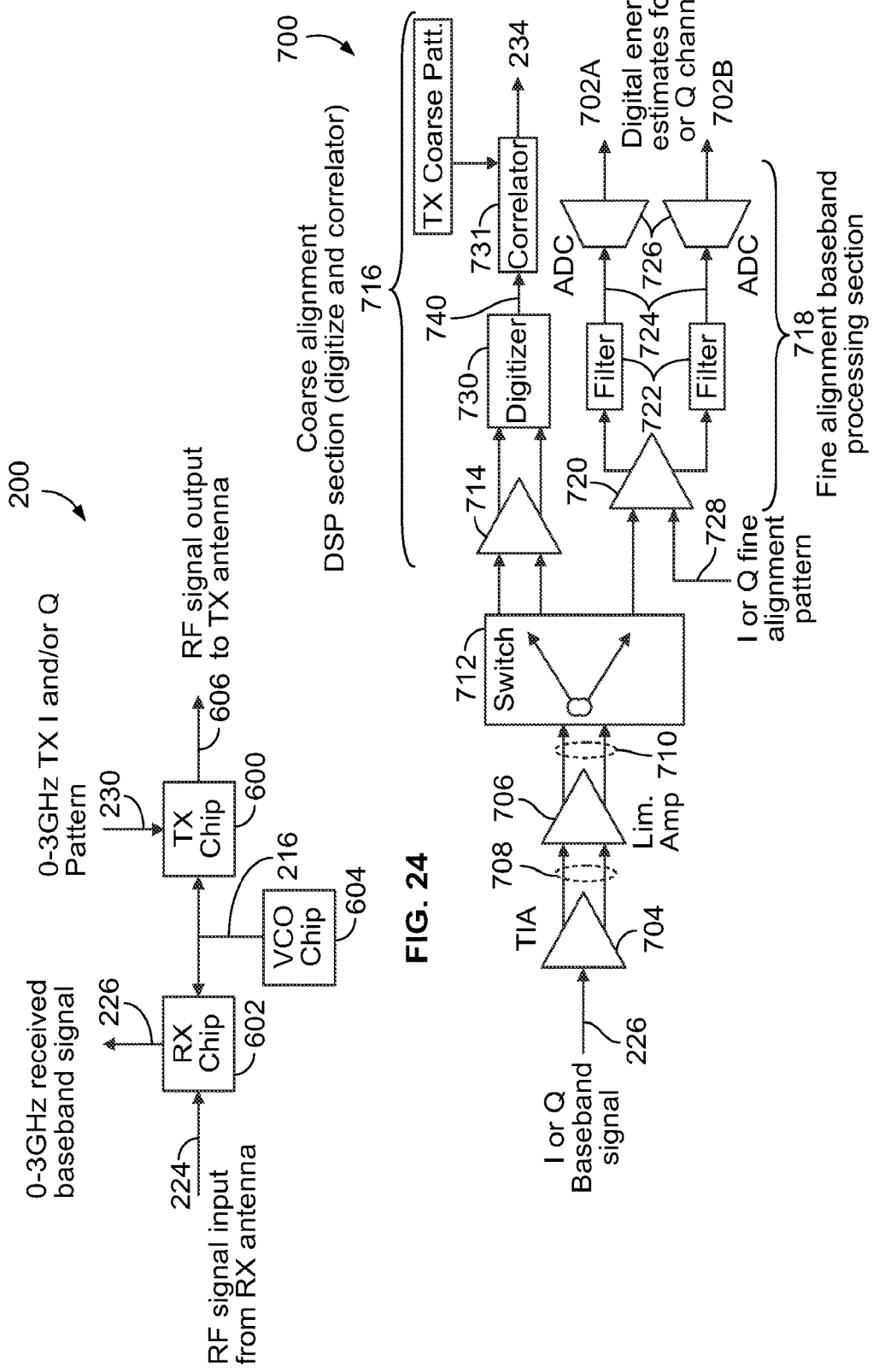
FIG. 24 is a schematic diagram of one embodiment of a front end of the sensing assembly shown in FIG. 19.
FIG. 25 is a circuit diagram of one embodiment of a baseband processing system of the system shown in FIG. 18.

FIG. 24 is a schematic diagram of one embodiment of the front end 200 of the sensing assembly 102 shown in FIG. 19. The front end 200 of the sensing assembly 102 may alternatively be referred to as the radio front end 500 (shown in FIG. 23) or the "radio" of the sensing assembly 102. In one embodiment, the front end 200 includes a direct-conversion transmitter 600 ("TX Chip" in FIG. 24) and receiver 602 ("RX Chip" in FIG. 24), with a common frequency reference generator 604 ("VCO Chip" in FIG. 24). The transmitter 600 may include or represent the front end transmitter 208 (shown in FIG. 19) and the receiver 602 may include or represent the front end receiver 218 (shown in FIG. 19).

The common frequency reference generator 604 may be or include the oscillator device 214 shown in FIG. 19. The common frequency reference generator 604 may be a voltage-controlled oscillator (VCO) that produces a frequency reference signal as the oscillating signal 216. In one embodiment, the frequency of the reference signal 216 is one half of a designated or desired carrier frequency of the transmitted signal 106 (shown in FIG. 18). Alternatively, the reference signal 216 may be another frequency, such as the same frequency as the carrier frequency, an integer multiple or divisor of the carrier frequency, and the like.

In one embodiment, the reference generator 604 emits a frequency reference signal 216 that is a sinusoidal wave at one half the frequency of the carrier frequency. The reference signal is split equally and delivered to the transmitter 600 and the receiver 602. Although the reference generator 604 may be able to vary the frequency of the reference signal 216 according to an input control voltage, the reference generator 604 can be operated at a fixed control voltage in order to cause the reference generator 604 to output a fixed frequency reference signal 216. This is acceptable since frequency coherence between the transmitter 600 and the receiver 602 may be automatically maintained. Furthermore, this arrangement can allow for coherence between the transmitter 600 and the receiver 602 without the need for a phase locked loop (PLL) or other control structure that may limit the accuracy and/or speed at which the sensing assembly 102 operates. In another embodiment, a PLL may be added to for other purposes, such as stabilizing the carrier frequency or otherwise controlling the carrier frequency.

The reference signal 216 can be split and sent to the transmitter 600 and receiver 602. The reference signal 216 drives the transmitter 600 and receiver 602, as described above. The transmitter 600 may drive (e.g., activate to transmit the transmitted signal 106 shown in FIG. 18) the transmitting antenna 204 (shown in FIG. 19). The receiver 602 may receive the return echo signal through the receiving antenna 206 (shown in FIG. 19) that is separate from the transmitting antenna 204. This can reduce the need for a T/R (transmit/receive) switch disposed between the transmitter 600 and the receiver 602. The transmitter 600 can up-convert the timing reference signal 216 and transmit an RF transmit signal 606 through the transmitting antenna 204 in order to drive the transmitting antenna 204 to transmit the transmitted signal 106 (shown in FIG. 18). In one embodiment, the output of the transmitter 600 can be at a maximum frequency or a frequency that is greater than one or more other frequencies in the sensing assembly 102 (shown in FIG. 18). For example, the transmit signal 606 from the transmitter 600 can be at the carrier frequency. This transmit signal 606 can be fed directly to the transmitting antenna 204 to minimize or reduce the losses incurred by the transmit signal 606.

In one embodiment, the transmitter 600 can take separate in-phase (I) and quadrature (Q) digital patterns or signals from the pattern generator 604 and/or the pattern code generator 228 (shown in FIG. 19). This can allow for increased flexibility in the transmit signal 606 and/or can allow for the transmit signal 606 to be changed "on the fly," or during transmission of the transmitted signals 106.

As described above, the receiver 602 may also receive a copy of the frequency reference signal 216 from the reference generator 604. The returning echoes 108 (shown in FIG. 18) are received by the receiving antenna 206 (shown in FIG. 19) and may be fed directly to the receiver 602 as the echo signal 224. This arrangement can give the system maximum or increased possible input signal-to-noise ratio (SNR), since the echo signal 224 propagates a minimal or relatively small distance before the echo signal 224 enters the receiver 602. For example, the echo signal 224 may not propagate or otherwise go through a switch, such as a transmit/receive (TX/RX) switch.

The receiver 602 can down-convert a relatively wide block of frequency spectrum centered on the carrier frequency to produce the baseband signal (e.g., the baseband echo signal 226 shown in FIG. 19). The baseband signal may then be processed by a baseband analog section of the sensing assembly 102 (shown in FIG. 18), such as the correlator device 731 (shown in FIG. 19) and/or one or more other components, to extract the time of flight ($t_F$). As described above, this received echo signal 224 includes a delayed copy of the TX pattern signal. The delay may be representative of and/or is a measurement of the round-trip, time-of-flight of the transmitted signal 106 and the corresponding echo 108.

The frequency reference signal 216 may contain or comprise two or more individual signals such as the I and Q components that are phase shifted relative to each other. The phase shifted signals can also be generated internally by the transmitter 600 and the receiver 602. For example, the signal 216 may be generated to include two or more phase shifted components (e.g., I and Q components or channels), or may be generated and later modified to include the two or more phase shifted components.

In one embodiment, the front end 200 provides relatively high isolation between the transmit signal 606 and the echo signal 224. This isolation can be achieved in one or more ways. First, the transmit and receive components (e.g., the transmitter 600 and receiver 602) can be disposed in physically separate chips, circuitry, or other hardware. Second, the reference generator 604 can operate at one half the carrier frequency so that feed-through can be reduced. Third, the transmitter 600 and the receiver 602 can have dedicated (e.g., separate) antennas 204, 206 that are also physically isolated from each other. This isolation can allow for the elimination of a TX/RX switch that may otherwise be included in the system 100. Avoiding the use of the TX/RX switch also can remove the switch-over time between the transmitting of the transmitted signals 106 and the receipt of the echoes 108 shown in FIG. 18. Reducing the switch-over time can enable the system 100 to more accurately and/or precisely measure distances to relatively close target objects 104. For example, reducing this switch-over time can reduce the threshold distance that may be needed between the sensing assembly 102 and the target object 104 in order for the sensing assembly 102 to measure the separation distance 110 shown in FIG. 18 before transmitted signals 106 are received as echoes 108.

FIG. 25 is a circuit diagram of one embodiment of a baseband processing system 232 of the system 100 shown in FIG. 18. In one embodiment, the baseband processing system 232 is included in the sensing assembly 102 (shown in FIG. 18) or is separate from the system 100 but operatively coupled with the system 100 to communicate one or more signals between the systems 100, 232. For example, the baseband processing system 232 can be coupled with the front end receiver 218 (shown in FIG. 19) to receive the echo signal 226 (e.g., the echo signal 226A and/or 226B). For example, at least part of the system 232 may be disposed between the front end receiver 218 and the Control and Processing Unit (CPU) 270 shown in FIG. 25. The baseband processing system 232 may provide for the coarse and/or fine and/or ultrafine stage determinations described above.

In one embodiment, the system 100 (shown in FIG. 18) includes a fine transmit pattern (e.g., a transmit pattern for fine stage determination) in the transmitted signal 106 following the coarse stage determination. For example, after transmitting a first transmit pattern in a first transmitted signal 106 (or one or more bursts of several transmitted signals 106) to use the coarse stage and calculate a time delay in the echo signal 226 (and/or the time of flight), a second transmit pattern can be included in a subsequent, second transmitted signal 106 for the fine stage determination of the time of flight (or a portion thereof). The transmit pattern in the coarse stage may be the same as the transmit pattern in the fine stage. Alternatively, the transmit pattern of the fine stage may differ from the transmit pattern of the coarse stage, such as by including one or more different waveforms or bits in a pulse sequence pattern of the transmitted signal 106.

The baseband processing system 232 receives the echo signal 226 (e.g., the I component or channel of the echo signal 226A and/or the Q component or channel of the echo signal 226B from the front end receiver 218 (shown in FIG. 18). The echo signal 226 that is received from the front end receiver 218 is referred to as "I or Q Baseband signal" in FIG. 25. As described below, the system 232 also may receive a receive pattern signal 728 ("I or Q fine alignment pattern" in FIG. 25) from the pattern code generator 228 (shown in FIG. 19). Although not shown in FIG. 19 or 25, the pattern code generator 228 and the system 232 may be coupled by one or more conductive pathways (e.g., busses, wires, cables, and the like) to communicate with each other. The system 232 can provide output signals 702A, 702B (collectively or individually referred to as an output signal 702 and shown as "Digital energy estimates for I or Q channel" in FIG. 25). In one embodiment, the baseband processing system 232 is an analog processing system. In another embodiment, the baseband processing system 232 is a hybrid analog and digital system comprised of components and signals that are analog and/or digital in nature.

The digitized echo signal 226 that is received by the system 232 may be conditioned by signal conditioning components of the baseband processing system 232, such as by modifying the signals using a conversion amplifier 704 (e.g., an amplifier that converts the baseband echo signal 226, such as by converting current into a voltage signal). In one embodiment, the conversion amplifier 704 includes or represents a trans-impedance amplifier, or "TIA" in FIG. 25). The signal conditioning components can include a second amplifier 706 (e.g., a limiting amplifier or "Lim. Amp" in FIG. 25). The conversion amplifier 704 can operate on a relatively small input signal that may be a single-ended (e.g., non-differential) signal to produce a differential signal 708 (that also may be amplified and/or buffered by the conversion amplifier 704 and/or one or more other components). This differential signal 708 may still be relatively small in amplitude. In one embodiment, the differential signal 708 is then passed to the second amplifier 706 that increases the gain of the differential signal 708. Alternatively, the second amplifier 706 may not be included in the system 232 if the conversion amplifier 704 produces a sufficiently large (e.g., in terms of amplitude and/or energy) output differential signal 710. The second amplifier 706 can provide relatively large gain and can tolerate saturated outputs 710. There may be internal positive feedback in the second amplifier 706 so that even relatively small input differences in the differential signal 708 can produce a larger output signal 710. In one embodiment, the second amplifier 706 quantizes the amplitude of the received differential signal 708 to produce an output signal 710.

The second amplifier 706 may be used to determine the sign of the input differential signal 708 and the times at which the sign changes from one value to another. For example, the second amplifier 706 may act as an analog-to-digital converter with only one bit precision in one embodiment. Alternatively, the second amplifier 706 may be a high-speed analog-to-digital converter that periodically samples the differential signal 708 at a relatively fast rate. Alternatively, the second amplifier may act as an amplitude quantizer while preserving timing information of the baseband signal 226. The use of a limiting amplifier as the second amplifier 706 can provide relatively high gain and relatively large input dynamic range. As a result, relatively small differential signals 708 that are supplied to the limiting amplifier can result in a healthy (e.g., relatively high amplitude and/or signal-to-noise ratio) output signal 710. Additionally, larger differential signals 708 (e.g., having relatively high amplitudes and/or energies) that may otherwise result in another amplifier being overdriven instead result in a controlled output condition (e.g., the limiting operation of the limiting amplifier). The second amplifier 706 may have a relatively fast or no recovery time, such that the second amplifier 706 may not go into an error or saturated state and may continue to respond to the differential signals 708 that are input into the second amplifier 706. When the input differential signal 708 returns to an acceptable level (e.g., lower amplitude and/or energy), the second amplifier 706 may avoid the time required by other amplifiers for recovery from an overdrive state (that is caused by the input differential signal 708). The second amplifier 706 may avoid losing incoming input signals during such a recovery time.

A switch device 712 ("Switch" in FIG. 25) that receives the output differential signal 710 (e.g., from the second amplifier 706) can control where the output differential signal 710 is sent. For example, the switch device 712 may alternate between states where, in one state (e.g., a coarse acquisition or determination state), the switch device 712 directs the output differential signal 710 along a first path 716 to the digitizer 730 and then to the correlator device 731. The digitizer 730 includes one or more analog or digital components, such as a processor, controller, buffers, digital gates, delay lines, samplers and the like, that digitize received signals into a digital signal, such as the digital echo signal 740 described above in connection with FIG. 21. The first path 716 is used to provide for the coarse stage determination of the time of flight, as described above. In one embodiment, the signals 710 may pass through another amplifier 714 and/or one or more other components before reaching the correlator device 731 for the coarse stage determination. In another state, the switch device 712 directs the output differential signal 710 along a different, second path 718 to one or more other components (described below). The second path 718 is used for the fine stage determination of the time of flight in the illustrated embodiment.

The switch device 712 may alternate the direction of flow of the signals (e.g., the output differential signal 710) from the first path 716 to the second path 718. Control of the switch device 712 may be provided by the control unit 112 (shown in FIG. 18). For example, the control unit 112 may communicate control signals to the switch device 712 to control where the signals flow after passing through the switch device 712.

The output differential signals 710 received by the switch device 712 may be communicated to a comparison device 720 in the second path 718. Alternatively, the switch device 712 (or another component) may convert the differential signals 710 into a single-ended signal that is input into the comparison device 720. The comparison device 720 also receives the receive pattern signal 728 from the pattern generator 228 (shown in FIG. 19). The receive pattern signal 728 is referred to as "I or Q fine alignment pattern" in FIG. 25). The receive pattern signal 728 may include a copy of the same transmit pattern that is transmitted in the transmitted signal 106 used to generate the echo signal 226 being analyzed by the system 232. Alternatively, the receive pattern signal 728 may differ from the transmit signal that is transmitted in the transmitted signal 106 used to generate the echo signal 226 being analyzed by the system 232.

The comparison device 720 compares the signals received from the switch device 712 with the receive pattern signal 728 to identify differences between the echo signal 226 and the receive pattern signal 728.

In one embodiment, the receive pattern signal 728 includes a pattern that is delayed by the time delay (e.g., the time of flight) identified by the coarse stage determination. The comparison device 720 may then compare this time-delayed pattern in the pattern signal 728 to the echo signal 226 (e.g., as modified by the amplifiers 704, 710) to identify overlaps or mismatches between the time-delayed pattern signal 728 and the echo signal 226.

In one embodiment, the comparison device 720 may include or represent a limiting amplifier that acts as a relatively high-speed XOR gate. An "XOR gate" includes a device that receives two signals and produces a first output signal (e.g., a "high" signal) when the two signals are different and a second output signal (e.g., a "low" signal) or no signal when the two signals are not different.

In another embodiment, the system may only include the coarse baseband processing circuits 716 or the fine baseband processing circuits 718. In this case, the switch 712 may also be eliminated. For example, this may be to reduce the cost or complexity of the overall system. As another example, the system may not need the fine accuracy and the rapid response of the coarse section 716 is desired. The coarse, fine and ultrafine stages may be used in any combination at different times in order to balance various performance metrics. Intelligent control can be manually provided by an operator or automatically generated by a processor or controller (such as the control unit 112) autonomously controlling the assembly 102 based on one or more sets of instructions (such as software modules or programs) stored on a tangible computer readable storage medium (such as a computer memory). The intelligent control can manually or automatically switch between which stages are used and/or when based on feedback from one or more other stages. For example, based on the determination from the coarse stage (e.g., an estimated time of flight or separation distance), the sensing assembly 102 may manually or automatically switch to the fine and/or ultrafine stage to further refine the time of flight or separation distance and/or to monitor movement of the target object 104.

With continued reference to FIG. 25, FIG. 26 is a schematic diagram of one example of how the comparison device 720 compares a portion 800 of the baseband echo signal 226 with a portion 802 of the time-delayed pattern signal 728 in one embodiment. Although only portions 800, 802 of the pattern signal 728 and the echo signal 226 are shown, the comparison device 720 may compare more, or all, of the echo signal 226 with the pattern signal 728. The portion 800 of the echo signal 226 and the portion 802 of the pattern signal 728 are shown disposed above each other and above a horizontal axis 804 that is representative of time. An output signal 806 represents the signal that is output from the comparison device 720. The output signal 806 represents differences (e.g., a time lag, amount of overlap, or other measure) between the portion 800 of the echo signal 226 and the portion 802 of the pattern signal 728. The comparison device 720 may output a single ended output signal 806 or a differential signal as the output signal 806 (having components 806A and 806B, as shown in FIG. 26).

In one embodiment, the comparison device 720 generates the output signal 806 based on differences between the portion 800 of the echo signal 226 and the portion 802 of the time-delayed pattern signal 728. For example, when a magnitude or amplitude of both portions 800, 802 is "high" (e.g., has a positive value) or when the magnitude or amplitude of both portions 800, 802 is "low" (e.g., has a zero or negative value), the comparison device 720 may generate the output signal 806 to have a first value. In the illustrated example, this first value is zero. When a magnitude or amplitude of both portions 800, 802 differ (e.g., one has a high value and the other has a zero or low value), the comparison device 720 may generate the output signal 806 with a second value, such as a high value.

In the example of FIG. 26, the portion 800 of the echo signal 226 and the portion 802 of the pattern signal 728 have the same or similar value except for time periods 808, 810. During these time periods 808, 810, the comparison device 720 generates the output signal 806 to have a "high" value. Each of these time periods 808, 810 can represent the time lag, or delay, between the portions 800, 802. During other time periods, the comparison device 720 generates the output signal 806 to have a different value, such as a "low" or zero value, as shown in FIG. 26. Similar output signals 806 may be generated for other portions of the echo signal 226 and pattern signal 728.

FIG. 27 illustrates another example of how the comparison device 720 compares a portion 900 of the baseband echo signal 226 with a portion 902 of the pattern signal 728. The portions 900, 902 have the same or similar values except for time periods 904, 906. During these time periods 904, 906, the comparison device 720 generates the output signal 806 to have a "high" value. During other time periods, the comparison device 720 generates the output signal 806 to have a different value, such as a "low" or zero value. As described above, the comparison device 720 may compare additional portions of the baseband signal 226 with the pattern signal 728 to generate additional portions or waveforms in the output signal 806.

FIG. 28 illustrates another example of how the comparison device 720 compares a portion 1000 of the baseband echo signal 226 with a portion 1002 of the pattern signal 230. The portions 1000, 1002 have the same or similar values over the time shown in FIG. 28. As a result, the output signal 806 that is generated by the comparison device 720 does not include any "high" values that represent differences in the portions 1000, 1002. As described above, the comparison device 720 may compare additional portions of the baseband signal 226 with the pattern signal 728 to generate additional portions or waveforms in the output signal 806. The output signals 806 shown in FIGS. 26, 27, and 28 are provided merely as examples and are not intended to be limitations on all embodiments disclosed herein.

The output signals 806 generated by the comparison device 720 represent temporal misalignment between the baseband echo signal 226 and the pattern signal 728 that is delayed by the time of flight or time delay measured by the coarse stage determination. The temporal misalignment may be an additional portion (e.g., to be added to) the time of flight of the transmitted signals 106 (shown in FIG. 18) and the echoes 108 (shown in FIG. 18) to determine the separation distance 110 (shown in FIG. 18).

The temporal misalignment between the baseband signal 226 and the pattern signal 728 may be referred to as a time lag. The time lag can be represented by the time periods 808, 810, 904, 906. For example, the time lag of the data stream 226 in FIG. 26 may be the time encompassed by the time period 808 or 810, or the time by which the portion 802 of the baseband signal 226 follows behind (e.g., lags) the portion 800 of the pattern signal 728. Similarly, the time lag of the portion 902 of the baseband signal 226 may be the time period 904 or 906. With respect to the example shown in FIG. 28, the portion 1000 of the baseband signal does not lag behind the portion 1002 of the pattern signal 728. As described above, several time lags may be measured by comparing more of the baseband signal 226 with the time-delayed pattern signal 728.

In order to measure the temporal misalignment between the baseband signal 226 and the time-delayed pattern signal, the output signals 806 may be communicated from the conversion device 720 to one or more filters 722. In one embodiment, the filters 722 are low-pass filters. The filters 722 generate energy signals 724 that are proportional to the energy of the output signals 806. The energy of the output signals 806 is represented by the size (e.g., width) of waveforms 812, 910 in the output signals 806. As the temporal misalignment between the baseband signal 226 and the pattern signal 728 increases, the size (and energy) of the waveforms 812, 910 increases. As a result, the amplitude and/or energy conveyed or communicated by the energy signals 724 increases. Conversely, as the temporal misalignment between the baseband signal 226 and the time-delayed pattern signal 728 decreases, the size and/or amplitude and/or energy of the waveforms 812, 910 also decreases. As a result, the energy conveyed or communicated by the energy signals 724 decreases.

As another example, the above system could be implemented using the opposite polarity, such as with an XNOR comparison device that produces "high" signals when the baseband signal 226 and the time-delayed pattern signal 728 are the same and "low" when they are different. In this example, as the temporal misalignment between the baseband signal 226 and the pattern signal 728 increases, the size (and energy) of the waveforms 812, 910 decreases. As a result, the amplitude and/or energy conveyed or communicated by the energy signals 724 decreases. Conversely, as the temporal misalignment between the baseband signal 226 and the time-delayed pattern signal 728 decreases, the size, amplitude, and/or energy of the waveforms 812, 910 also increases. As a result, the energy conveyed or communicated by the energy signals 724 increases.

The energy signals 724 may be communicated to measurement devices 726 ("ADC" in FIG. 25). The measurement devices 726 can measure the energies of the energy signals 724. The measured energies can then be used to determine the additional portion of the time of flight that is represented by the temporal misalignment between the baseband signal 226 and the time-delayed pattern signal 728. In one embodiment, the measurement device 726 periodically samples the energy and/or amplitude of energy signals 724 in order to measure the energies of the energy signals 724. For example, the measurement devices 726 may include or represent analog-to-digital converters (ADC) that sample the amplitude and/or energy of the energy signals 724 in order to measure or estimate the alignment (or misalignment) between the echo signal 226 and the pattern signal 728. The sampled energies can be communicated by the measurement devices 726 as the output signal 702 to the control unit 112 or other output device or component (shown as "Digital energy estimates for I or Q channel" in FIG. 25).

The control unit 112 (or other component that receives the output signal 710) may examine the measured energy of the energy signals 724 and calculate the additional portion of the time of flight represented by the temporal misalignment between the baseband signal 226 and the time-delayed pattern signal 728. The control unit 112 also may calculate the additional portion of the separation distance 110 that is associated with the temporal misalignment. In one embodiment, the control unit 112 compares the measured energy to one or more energy thresholds. The different energy thresholds may be associated with different amounts of temporal misalignment. Based on the comparison, a temporal misalignment can be identified and added to the time of flight calculated using the coarse stage determination described above. The separation distance 110 may then be calculated based on the combination of the coarse stage determination of the time of flight and the additional portion of the time of flight from the fine stage determination.

FIG. 29 illustrates examples of output signals 724 provided to the measurement devices 726 and energy thresholds used by the control unit 112 or other component or device (shown in FIG. 19) in accordance with one example. The output signals 702 are shown alongside a horizontal axis 1102 representative of time and a vertical axis 1104 representative of energy. Several energy thresholds 1106 are shown above the horizontal axis 1102. Although eight output signals 724A-H and eight energy thresholds 1106A-H are shown, alternatively, a different number of output signals 724 and/or energy thresholds 1106 may be used.

The measurement devices 726 may digitize the energy signals 724 to produce the energy data output signals 702. When the output signals 702 are received from the measurement devices 726 (shown in FIG. 25) by the CPU 270, the output signals 706 can be compared to the energy thresholds 1106 to determine which, if any, of the energy thresholds 1106 are exceeded by the output signals 702. For example, the output signals 702 having less energy (e.g., a lower magnitude) than the energies associated with the output signal 702A may not exceed any of the thresholds 1106, while the output signal 702A approaches or reaches the threshold 1106A. The output signal 702B is determined to exceed the threshold 1106A, but not exceed the threshold 1106B. As shown in FIG. 29, other output signals 702 may exceed some thresholds 1106 while not exceeding other thresholds 1106.

The different energy thresholds 1106 are associated with different temporal misalignments between the echo signal 226 and the time-delayed pattern signal 728 in one embodiment. For example, the energy threshold 1106A may represent a temporal misalignment of 100 picoseconds, the energy threshold 1106B may represent a temporal misalignment of 150 picoseconds, the energy threshold 1106C may represent a temporal misalignment of 200 picoseconds, the energy threshold 1106D may represent a temporal misalignment of 250 picoseconds, and so on. For example, 724B may be the result of the situation shown in FIGS. 26 and 724E may be the result of the situation in FIG. 27.

The measured energy of the output signal 702 can be compared to the thresholds 1106 to determine if the measured energy exceeds one or more of the thresholds 1106.

The temporal misalignment associated with the largest threshold 1106 that is approached or reached or represented by the energy of the output signal 702 may be identified as the temporal misalignment between the echo signal 226 and the time-delayed pattern signal 728. In one embodiment, no temporal alignment may be identified for output signals 702 having or representing energies that are less than the threshold 1106A.

The energy thresholds 1106 may be established by positioning target objects 104 (shown in FIG. 18) a known separation distance 110 (shown in FIG. 18) from the sensing assembly 102 (shown in FIG. 18) and observing the levels of energy that are represented or reached or approached by the output signals 702.

In addition or as an alternate to performing the fine stage determination of the time of flight, the ultrafine stage may be used to refine (e.g., increase the resolution of) the time of flight measurement, track movement, and/or detect movement of the target object 104 (shown in FIG. 18). In one embodiment, the ultrafine stage includes comparing different components or channels of the same or different echo signals 226 as the fine stage determination. For example, in one embodiment, the coarse stage determination may measure a time of flight from echo signals 226 that are based on echoes 108 received from transmission of a first set or burst of one or more transmitted signals 106, as described above. The fine stage determination may measure an amount of temporal misalignment or overlap between echo signals 226 that are based on echoes 108 received from transmission of a subsequent, second set or burst of one or more transmitted signals 106 (that may use the same or different transmit pattern as the first set or burst of transmitted signals 106). The fine stage determination may measure the temporal misalignment between the echo signals 226 from the second set or burst of transmitted signals 106 and a receive pattern signal (which may be the same or different receive pattern as used by the coarse stage determination) as that is time delayed by the time of flight measured by the coarse stage, as described above. In one embodiment, the fine stage determination examines the I and/or Q component or channel of the echo signals 226. The ultrafine stage determination may measure the temporal misalignment of the echo signals 226 from the same second set or burst of transmitted signals 106 as the fine stage determination, or from a subsequent third set or burst of transmitted signals 106. The ultrafine stage determination may measure the temporal misalignment between the echo signals 226 and a receive pattern signal (that is the same or different as the receive pattern signal used by the fine stage determination) that is time-delayed by the time of flight measured by the coarse stage. In one embodiment, the ultrafine stage measures the temporal misalignment of the I and/or Q component or channel of the echo signals 226 while the fine stage measures the temporal misalignment of the Q and/or I component or channel of the same or different echo signals 226. The temporal misalignment of the I component may be communicated to the control unit 112 (or other component or device) as the output signals 702 (as described above) while the temporal misalignment of the Q component may be communicated to the control unit 112 (or other component or device) as output signals 1228. Alternatively or additionally, the time lag of the waveforms in the I channel and Q channel can be examined to resolve phases of the echoes in order to calculate separation distance or motion of the target.

As described above, the ultrafine stage determination may alternatively or additionally involve a similar process as the coarse stage determination. For example, the coarse stage determination may examine the I channel of the receive pattern and the data stream to determine correlation values of different subsets of the data stream and, from those correlation values, determine a subset of interest and a corresponding time-of-flight, as described herein. The ultrafine stage determination can use the Q channel of the receive pattern and the data stream to determine correlation values of different subsets of the data stream and, from those correlation values, determine a subset of interest and a time-of-flight. The times-of-flight from the I channel and Q channel can be combined (e.g., averaged) to calculate a time of flight and/or separation distance to the target. The correlation values calculated by the ultrafine stage determination can be used to calculate an additional time delay that can be added to the time delays from the coarse stage and/or the fine stage to determine a time of flight and/or separation distance to the target. Alternatively or additionally, the correlation values of the waveforms in the I channel and Q channel can be examined to resolve phases of the echoes in order to calculate separation distance or motion of the target.

Figure 30:
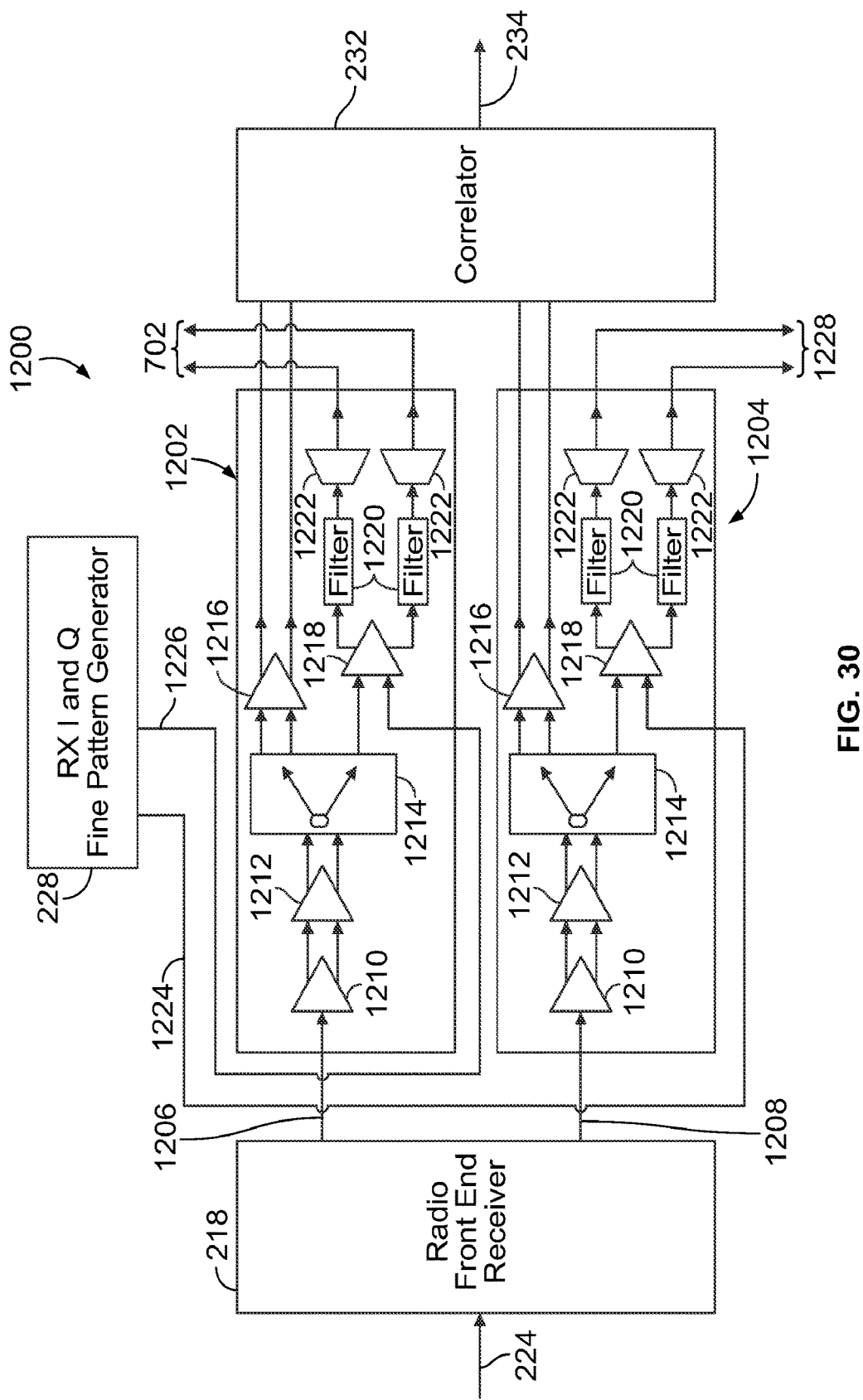
FIG. 30 is a circuit diagram of another embodiment of a baseband processing system of the system shown in FIG. 18.

FIG. 30 is a circuit diagram of another embodiment of a baseband processing system 1200 of the system 100 shown in FIG. 18. In one embodiment, the baseband processing system 1200 is similar to the baseband processing system 232 (shown in FIG. 25). For example, the baseband processing system 1200 may be included in the sensing assembly 102 (shown in FIG. 18) by being coupled with the front end receiver 218, the pattern code generator 228, and/or the baseband processor 232 of the sensing assembly 102. The baseband processing system 1200 includes two or more parallel paths 1202, 1204 that the I and Q components of the baseband echo signal 226 and the pattern signal can flow through for processing and analysis. For example, a first path 1202 can process and analyze the I components of the echo signal 224 and baseband echo signal 226 and the second path 1204 can process and analyze the Q components of the echo signal 224 and the baseband echo signal 226. In the illustrated embodiment, each of the paths 1202, 1204 includes the baseband processing system 232 described above. Alternatively, one or more of the paths 1202, 1204 may include one or more other components for processing and/or analyzing the signals. In another embodiment, only a single path 1202 or 1204 may process and/or analyze multiple, different components of the baseband echo signal 224 and/or baseband echo signal 226. For example, the path 1202 may examine the I component of the signal 224 and/or 226 during a first time period and then examine the Q component of the signal 224 and/or 226 during a different (e.g., subsequent or preceding) second time period.

In operation, the echo signal 224 is received by the front end receiver 218 and is separated into separate I and Q signals 1206, 1208 (also referred to herein as I and Q channels). Each separate I and Q signal 1206, 1208 includes the corresponding I or Q component of the echo signal 224 and can be processed and analyzed similar to the signals described above in connection with the baseband processing system 232 shown in FIG. 25. For example, each of the I signal 1206 and the Q signal 1208 can be received and/or amplified by a conversion amplifier 1210 (that is similar to the conversion amplifier 704) in each path 1202, 1204 to output a differential signal (e.g., similar to the signal 708 shown in FIG. 25) to another amplifier 1212 (e.g., similar to the amplifier 706 shown in FIG. 25). The amplifiers 1212 can produce signals having increased gain (e.g., similar to the signals 710 shown in FIG. 25) that are provided to switch devices 1214. The switch devices 1214 can be similar to the switch device 712 (shown in FIG. 25) and can communicate the signals from the amplifiers 1212 to amplifiers 1216 (which may be similar to the amplifier 714 shown in FIG. 25) and/or the correlator device 232 for the coarse stage identification of a time of flight, as described above.

Similar to as described above in connection with the switch device 712 (shown in FIG. 25), the switch devices 1214 can direct the signals from the amplifiers 1212 to comparison devices 1218 (that may be similar to the comparison device 720 shown in FIG. 25), filters 1220 (that may be similar to the filters 722 shown in FIG. 25), and measurement devices 1222 (that may be similar to the measurement devices 726 shown in FIG. 25). The comparison devices 1218 may each receive different components of a receive pattern signal from the pattern code generator 228. For example, the comparison device 1218 in the first path 1202 may receive an I component 1224 of a receive pattern signal for the fine stage and the comparison device 1218 in the second path 1202 may receive the Q component 1226 of the receive pattern signal for the ultrafine stage. The comparison devices 1218 generate output signals that represent temporal misalignments between the I or Q components 1224, 1226 of the receive pattern signal and the I or Q components of the echo signal 226, similar to as described above. For example, the comparison device 1218 in the first path 1202 may output a signal having an energy that represents (e.g., is proportional to) the temporal misalignment between the I component of the baseband echo signal 226 and the I component of the time-delayed receive pattern signal 728. The comparison device 1218 in the second path 1204 may output another signal having an energy that represents the temporal misalignment between the Q component of the baseband echo signal 226 and the Q component of the time-delayed pattern signal 728. Alternatively, there may be a single path 700, as shown in FIG. 25, that may be shared between I and Q operation. This could be accomplished by alternately providing or switching between the I and Q components of the baseband echo signal 226A and 226B.

As described above, the energies of the signals output from the comparison devices 1218 can pass through the filters 1220 and be measured by the measurement devices 1222 to determine each of the temporal misalignments associated with the I and Q components of the echo signal 226 and the receive pattern signal. These temporal misalignments can be added together and added to the time of flight determined by the coarse stage determination. The sum of the temporal misalignments and the time of flight from the coarse stage determination can be used by the baseband processor 232 to calculate the separation distance 110 (shown in FIG. 18), as described above. Because the I and Q components of the echo signal and the time-delayed receive pattern signal are phase shifted by approximately 90 degrees from each other, separately examining the I and Q components allows calculation of the carrier phase of the returning signal 108 according to Equation 2 below and can provide resolution on the order of one eighth or better (smaller) of the wavelength of the carrier signal of the transmitted signals 106 and echoes 108. Alternatively, there may be 3 or more components separated by an amount other than 90 degrees.

In one embodiment, the ultrafine stage determination described above can be used to determine relatively small movements that change the separation distance 110 (shown in FIG. 18). For example, the ultrafine stage may be used to identify relatively small movements within a portion of the separation distance 110 that is associated with the subset of interest in the baseband echo signal 226.

Figure 31:
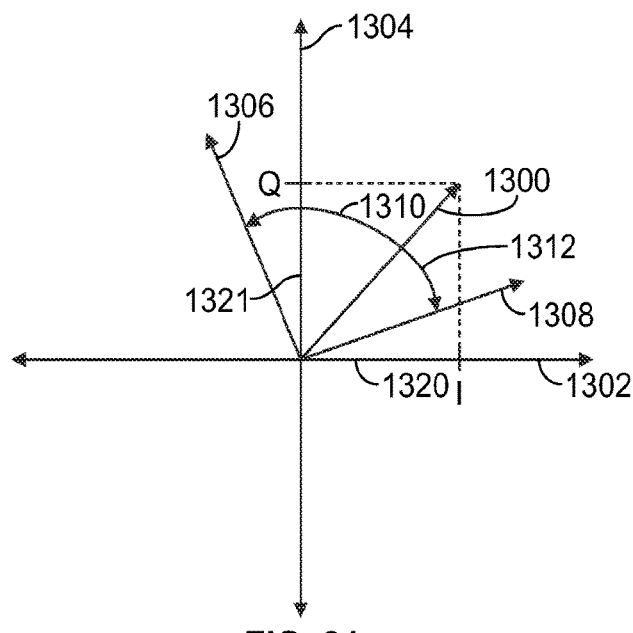
FIG. 31 illustrates projections of in-phase (I) and quadrature (Q) components of a digitized echo signal shown in FIG. 19 in accordance with one embodiment.

FIG. 31 illustrates projections of I and Q components of the baseband echo signal 226 in accordance with one embodiment. The ultrafine stage determination can include the baseband processor 232 (shown in FIG. 19) projecting a characteristic of the I and Q components of the baseband echo signal 226 onto a vector. As shown in FIG. 31, a vector 1300 is shown alongside a horizontal axis 1302 and a vertical axis 1304. The backend 202 or control unit 112 or other processing or computation devices by examination of the data signals 234, 702, 1228, 260, or others or a combination of some or all of the signals may determine the vector 1300 as a projection of the characteristic (e.g., amplitude) of the I component 1320 of the echo signal along the horizontal axis 1302 and a projection of the characteristic (e.g., amplitude) of the Q component 1321 of the echo signal along the vertical axis 1304. For example, the vector 1300 may extend to a location along the horizontal axis 1302 by an amount that is representative of an amplitude of the I component of the echo signal and to a location along the vertical axis 1304 by an amount that is representative of an amplitude of the Q component of the echo signal. The phase of the carrier can then calculated as:

$$\varphi = \arctan\left(\frac{I}{Q}\right) \quad \text{(Equation \#2)}$$

where φ denotes the phase and I is the I projection 1320 and Q is the Q projection 1321. The carrier phase or the change in carrier phase can be used to calculate the distance or change in distance through the equation:

$$\text{distance} = \frac{\varphi \times \lambda}{360} \quad \text{(Equation \#3)}$$

where λ is the wavelength of the carrier frequency and φ is the phase expressed in degrees as calculated from Equation 2 above.

The baseband processor 232 (shown in FIG. 19) may then determine additional vectors 1306, 1308 based on the echoes 108 (shown in FIG. 18) received from additional transmitted signals 106 (shown in FIG. 18). Based on changes in the vector 1300 to the vector 1306 or the vector 1308, the baseband processor 232 may identify movement of the target object 104 (shown in FIG. 18) within the portion of the separation distance 110 (shown in FIG. 18) that is associated with the subset of interest. For example, rotation of the vector 1300 in a counter-clockwise direction 1310 toward the location of the vector 1306 may represent movement of the target object 104 toward the sensing assembly 102 shown in FIG. 18 (or movement of the sensing assembly 102 toward the target object 104). Rotation of the vector 1300 in a clockwise direction 1312 toward the location of the vector 1308 may represent movement of the target object 104 away from the sensing assembly 102 (or movement of the sensing assembly 102 toward the target object 104). Alternatively, movement of the vector 1300 in the counter-clockwise direction 1310 may represent movement of the target object 104 away from the sensing assembly 102 (or movement of the sensing assembly 102 toward the target object 104) while movement of the vector 1300 in the clockwise direction 1312 may represent movement of the target object 104 toward the sensing assembly 102 shown in FIG. 18 (or movement of the sensing assembly 102 toward the target object 104). The correlator device 232 may be calibrated by moving the target object 104 toward and away from the sensing assembly 102 to determine which direction of movement results in rotation of the vector 1300 in the clockwise direction 1312 or counter-clockwise direction 1310.

The coarse, fine, and/or ultrafine stage determinations described above may be used in a variety of combinations. For example, the coarse stage determination may be used to calculate the separation distance 110 (shown in FIG. 18), even if the approximate distance from the sensing device 102 (shown in FIG. 18) to the target object 104 (shown in FIG. 18) is not known. Alternatively, the coarse stage may be used with the fine and/or ultrafine stage determinations to obtain a more precise calculation of the separation distance 110. The coarse, fine and ultrafine stages may be used in any combination at different times in order to balance various performance metrics.

As another example, if the separation distance 110 (shown in FIG. 18) is known, the fine or ultrafine stage determinations can be activated without the need for first identifying the bit of interest using the coarse stage determination. For example, the system 100 (shown in FIG. 18) may be in a "tracking" mode where updates from the initial known separation distance 110 are identified and/or recorded using the fine and/or ultrafine state determinations.

Returning to the discussion of the system 100 shown in FIG. 18, in another embodiment, the system 100 discern between echoes 108 that are reflected off of different target objects 104. For example, in some uses of the system 100, the transmitted signals 106 may reflect off of multiple target objects 104. If the target objects 104 are located different separation distances 110 from the sensing assembly 102, a single baseband echo signal 226 (shown in FIG. 19) may represent several sequences of bits that represent echoes off the different target objects 104. As described below, a mask may be applied to the baseband echo signal 226 and the pattern in the correlation window that is compared to the baseband echo signal 226 in order to distinguish between the different target objects 104.

Figure 32:
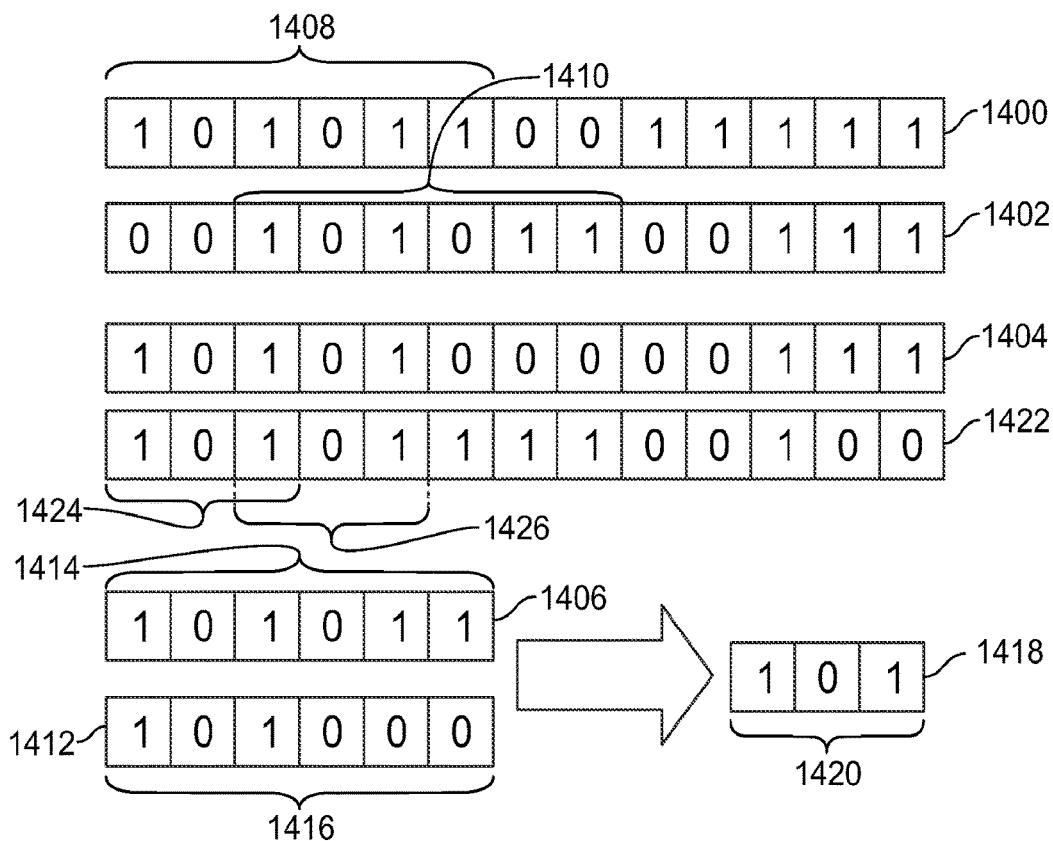
FIG. 32 illustrates a technique for distinguishing between echoes shown in FIG. 18 that are reflected off different target objects shown in FIG. 18 in accordance with one embodiment.

FIG. 32 illustrates a technique for distinguishing between echoes 108 (shown in FIG. 18) that are reflected off different target objects 104 (shown in FIG. 18) in accordance with one embodiment. When a first transmitted signal 106 shown in FIG. 18 (or a series of first transmitted signals 106) reflect off of multiple target objects 104, the digital pulse sequence (e.g., the pattern of bits) in the pattern signal 230 (shown in FIG. 19) may be modified relative to the digital pulse sequence in the first transmitted signal 106 for transmission of a second transmitted signal 106 (or series of second transmitted signals 106). The echoes 108 and corresponding baseband echo signal 226 (shown in FIG. 19) of the second transmitted signal 106 may be compared to the modified digital pulse sequence to distinguish between the multiple target objects 104 (e.g., to calculate different times of flight and/or separation distances 110 associated with the different target objects 104).

A first digitized echo signal 1400 in FIG. 32 represents the sequence of bits that may be generated when a transmitted signal 106 (shown in FIG. 18) reflects off a first target object 104 at a first separation distance 110 (shown in FIG. 18) from the sensing assembly 102 (shown in FIG. 18). A second digitized echo signal 1402 represents the sequence of bits that may be generated when the transmitted signal 106 reflects off a different, second target object 104 that is a different, second separation distance 110 from the sensing assembly 102. Instead of separately generating the digitized echo signals 1400, 1402, the sensing assembly 102 may generate a combined digitized echo signal 1404 that represents the combination of echoes 108 off the different target objects 104. The combined digitized echo signal 1404 may represent a combination of the digitized echo signals 1400, 1402.

A correlation window 1406 includes a sequence 1414 of bits that can be compared to either digitized echo signal 1400, 1402 to determine a subset of interest, such as the subsets of interest 1408, 1410, in order to determine times of flight to the respective target objects 104 (shown in FIG. 18), as described above. However, when the echoes 108 (shown in FIG. 18) off the target objects 104 are combined and the combined digitized echo signal 1404 is generated, the correlation window 1406 may be less accurate or unable to determine the time of flight to one or more of the several target objects 104. For example, while separate comparison of the correlation window 1406 to each of the digitized echo signals 1400, 1402 may result in correlation values of +6 being calculated for the subsets of interest 1408, 1410, comparison of the correlation window 1406 to the combined digitized echo signal 1404 may result in correlation values of +5, +4, and +4 for the subsets that include the first through sixth bits, the third through eighth bits, and the seventh through twelfth bits in the combined digitized echo signal 1404. As a result, the baseband processor 232 (shown in FIG. 19) may be unable to distinguish between the different target objects 104 (shown in FIG. 18).

In one embodiment, a mask 1412 can be applied to the sequence 1414 of bits in the correlation window 1406 to modify the sequence 1414 of bits in the correlation window 1406. The mask 1412 can eliminate or otherwise change the value of one or more of the bits in the correlation window 1406. The mask 1412 can include a sequence 1416 of bits that are applied to the correlation window 1406 (e.g., by multiplying the values of the bits) to create a modified correlation window 1418 having a sequence 1420 of bits that differs from the sequence 1414 of bits in the correlation window 1406. In the illustrated example, the mask 1412 includes a first portion of the first three bits ("101") and a second portion of the last three bits ("000"). Alternatively, another mask 1412 may be used that has a different sequence of bits and/or a different length of the sequence of bits. Applying the mask 1412 to the correlation window 1406 eliminates the last three bits ("011") in the sequence 1414 of bits in the correlation window 1406. As a result, the sequence 1420 of bits in the modified correlation window 1418 includes only the first three bits ("101") of the correlation window 1418. In another embodiment, the mask 1412 adds additional bits to the correlation window 1406 and/or changes values of the bits in the correlation window 1406.

The sequence 1420 of bits in the modified correlation window 1418 can be used to change the sequence of bits in the pattern signal 230 (shown in FIG. 19) that is communicated to the transmitter for inclusion in the transmitted signals 106 (shown in FIG. 18). For example, after receiving the combined digitized echo signal 1404 and being unable to discern between the different target objects 104 (shown in FIG. 18), the sequence of bits in the pattern that is transmitted toward the target objects 104 can be changed to include the sequence 1420 of bits in the modified correlation window 1412 or some other sequence of bits to aid in the discernment of the different target objects 104. An additional combined digitized echo signal 1422 may be received based on the echoes 108 of the transmitted signals 106 that include the sequence 1420 of bits.

The modified correlation window 1418 can then be compared with the additional digitized echo signal 1422 to identify subsets of interest associated with the different target objects 104 (shown in FIG. 18). In the illustrated embodiment, the modified correlation window 1418 can be compared to different subsets of the digitized echo signal 1422 to identify first and second subsets of interest 1424, 1426, as described above. For example, the first and second subsets of interest 1424, 1426 may be identified as having higher or the highest correlation values relative to other subsets of the digitized echo signal 1422.

In operation, when transmitted signals 106 reflect off multiple target objects 104, the pattern transmitted in the signals 106 can be modified relatively quickly between successive bursts of the transmitted signals 106 when one or more of the target objects 104 cannot be identified from examination of the digitized echo signal 226. The modified pattern can then be used to distinguish between the target objects 104 in the digitized echo signal 740 using the correlation window that includes the modified pattern.

In another embodiment, the digital pulse sequence of bits included in a transmitted signal 106 (shown in FIG. 18) may be different from the digital pulse sequence of bits included in the correlation window and compared to the baseband echo signal 226 (shown in FIG. 19). For example, the pattern code generator 228 (shown in FIG. 19) may create heterogeneous patterns and communicate the heterogeneous patterns in the pattern signals 230 (shown in FIG. 19) to the transmitter 208 and the baseband processor 232. The transmitter 208 can mix a first pattern of bits in the transmitted signal 106 and the baseband processor 232 can compare a different, second pattern of bits to the baseband echo signal 226 that is generated based on echoes 108 (shown in FIG. 18) of the transmitted signals 106. With respect to the example described above in connection with FIG. 32, the sequence 1414 of bits in the correlation window 1406 can be included in the transmitted signals 106 while the sequence 1416 of bits in the mask 1412 or the sequence 1420 of bits in the modified correlation window 1418 can be compared to the digitized echo signal 1422. Using different patterns in this manner can allow for the sensing assembly 102 (shown in FIG. 18) to distinguish between multiple target objects 104, as described above. Using different patterns in this manner can additionally allow for the sensing assembly 102 (shown in FIG. 18) to perform other functions including, but not limited to clutter mitigation, signal-to-noise improvement, anti-jamming, anti-spoofing, anti-eavesdropping, and others.

Figure 33:
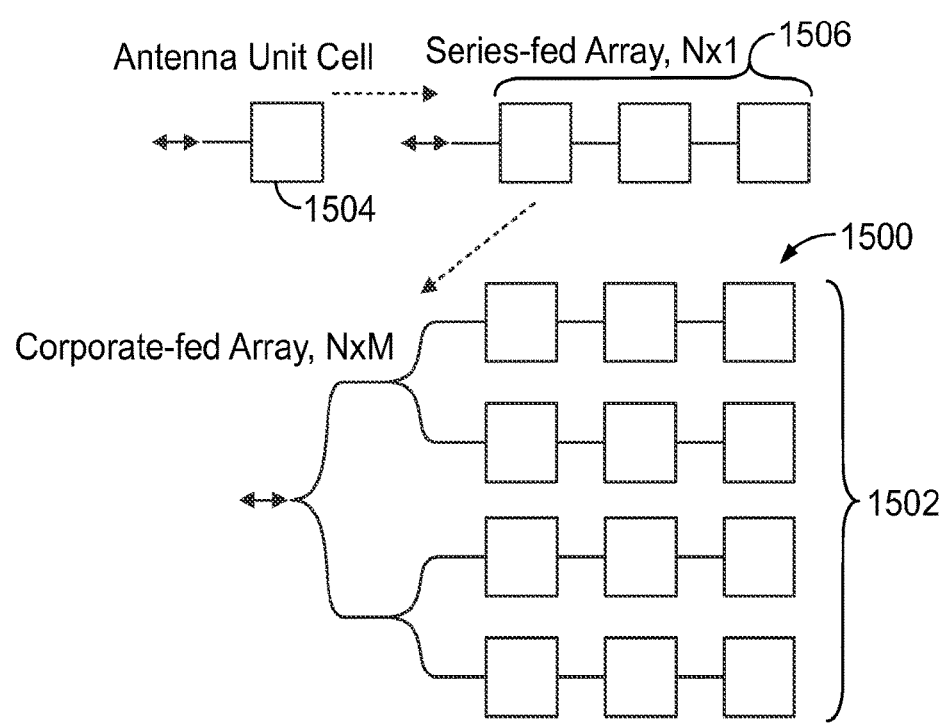
FIG. 33 is a schematic view of an antenna in accordance with one embodiment.

FIG. 33 is a schematic view of an antenna 1500 in accordance with one embodiment. The antenna 1500 may be used as the transmitting antenna 204 and/or the receiving antenna 206, both of which are shown in FIG. 19. Alternatively, another antenna may be used for the transmitting antenna 204 and/or the receiving antenna 206. The antenna 1500 includes a multi-dimensional (e.g., two dimensional) array 1502 of antenna unit cells 1504. The unit cells 1504 may represent or include microstrip patch antennas. Alternatively, the unit cells 1504 may represent another type of antenna. Several unit cells 1504 can be conductively coupled in series with each other to form a series-fed array 1506. In the illustrated embodiment, the unit cells 1504 are connected in a linear series. Alternatively, the unit cells 1504 can be connected in another shape.

Several series-fed arrays 1506 are conductively coupled in parallel to form the array 1502 in the illustrated embodiment. The numbers of unit cells 1504 and series-fed arrays 1506 shown in FIG. 33 are provided as examples. A different number of unit cells 1504 and/or arrays 1506 may be included in the antenna 1500. The antenna 1500 may use the several unit cells 1504 to focus the energy of the transmitted signals 106 (shown in FIG. 18) through constructive and/or destructive interference.

Figure 34:
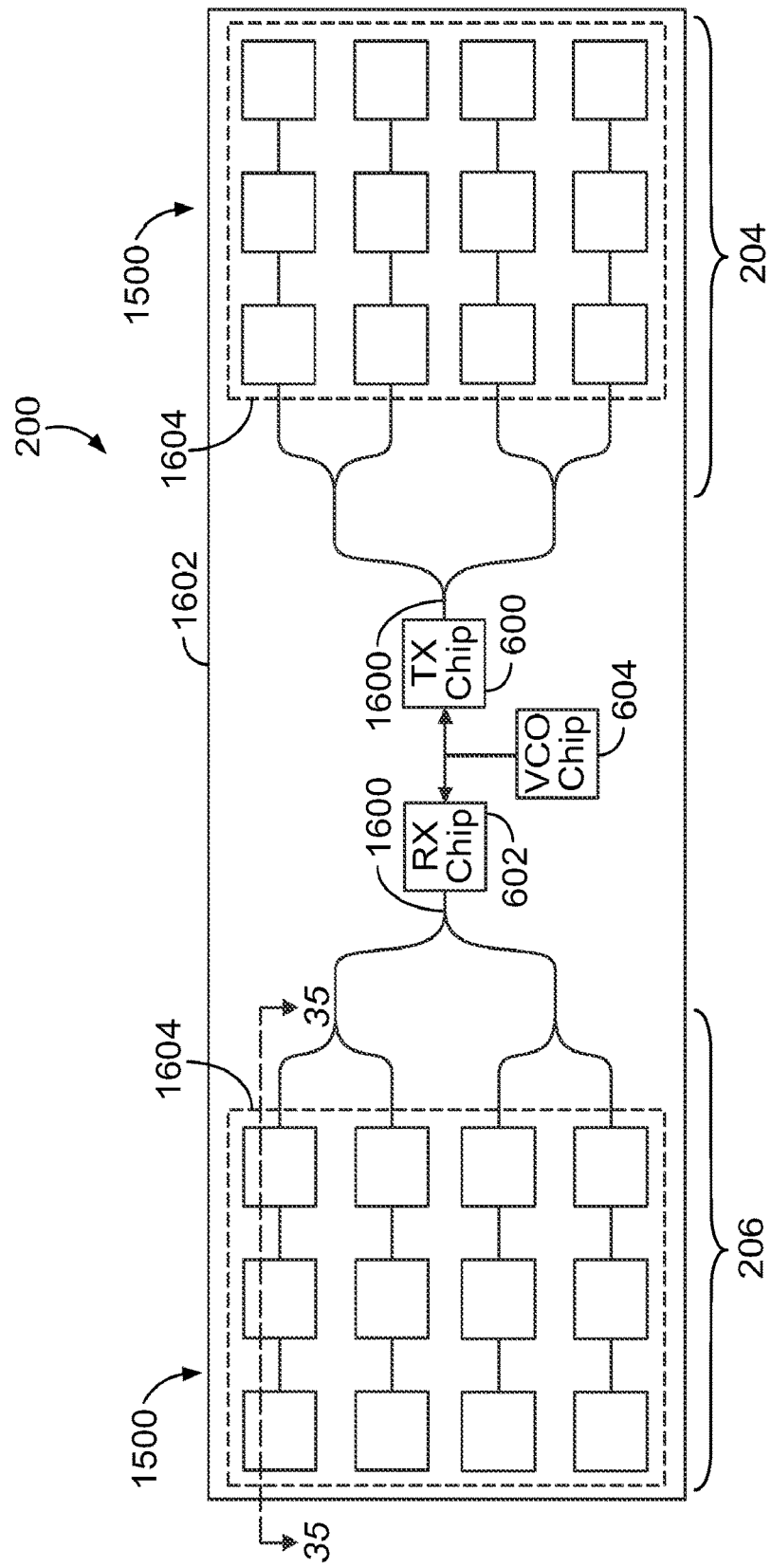
FIG. 34 is a schematic diagram of one embodiment of a front end of the sensing assembly shown in FIG. 18.

FIG. 34 is a schematic diagram of one embodiment of the front end 200 of the sensing assembly 102 (shown in FIG. 18). The antennas 1500 may be used as the transmitting antenna 204 and the receiving antenna 206, as shown in FIG. 34. Each antenna 1500 may be directly connected to the receiver 602 or transmitter 600 (e.g., with no other components disposed between the antenna 1500 and the receiver 602 or transmitter 600) by a relatively short length of transmission line 1600.

The front end 200 of the sensing assembly 102 may be housed in an enclosure 1602, such as a metal or otherwise conductive housing, with radio transmissive windows 1604 over the antennas 1500. Alternatively, the front end 200 may be housed in a non-metallic (e.g., dielectric) enclosure. The windows over the antennas 1500 may not be cut out of the enclosure 1602, but may instead represent portions of the enclosure 1602 that allows the transmitted signals 106 and echoes 108 pass through the windows 1604 from or to the antennas 1500.

The enclosure 1602 may wrap around the antennas 1500 so that the antennas are effectively recessed into the conducting body of the enclosure 1602, which can further improve isolation between the antennas 1500. Alternatively, in the case of a non-conducting enclosure 1602, the antennas 1500 may be completely enclosed by the enclosure 1602 and extra metal foil, and/or absorptive materials, or other measures may be added to improve isolation between the antennas 1500. In one embodiment, if the isolation is sufficiently high, the transmit and receiving antennas 1500 can be operated at the same time if the returning echoes 108 are sufficiently strong. This may be the case when the target is at very close range, and can allow for the sensing assembly 102 to operate without a transmit/receive switch.

Figure 35:
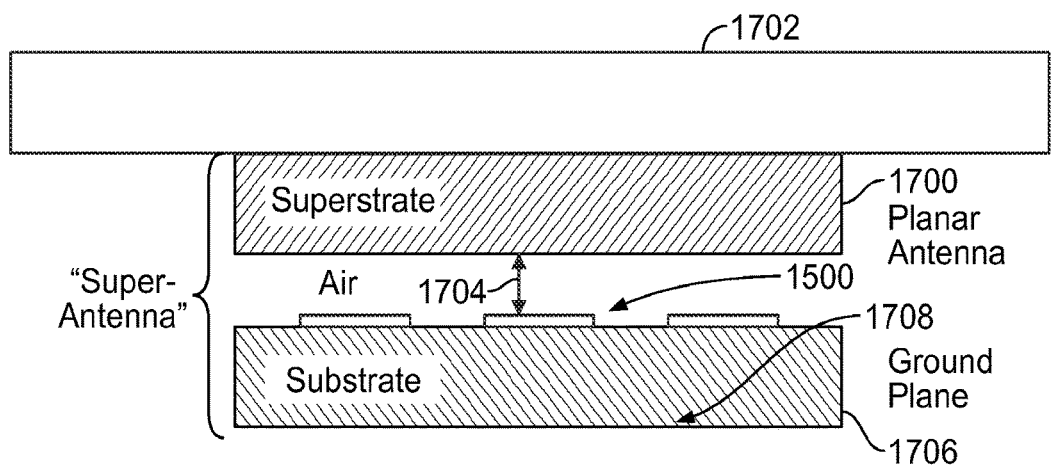
FIG. 35 is a cross-sectional view of one embodiment of the antenna shown in FIG. 33 along line 35-35 in FIG. 34.

FIG. 35 is a cross-sectional view of one embodiment of the antenna 1500 along line 35-35 in FIG. 34. The antenna 1500 ("Planar Antenna" in FIG. 35) includes a cover layer 1700 ("Superstrate" in FIG. 35) of an electrically insulating material (such as a dielectric or other nonconducting material). Examples of such materials for the cover layer 1700 include, but are not limited to quartz, sapphire, various polymers, and the like.

The antenna 1500 may be positioned on a surface of a substrate 1706 that supports the antenna 1500. A conductive ground plane 1708 may be disposed on an opposite surface of the substrate 1706, or in another location.

The cover layer 1700 may be separated from the antenna 1500 by an air gap 1704 ("Air" in FIG. 35). Alternatively, gap between the cover layer 1700 and the antenna 1500 may be at least partially filled by another material or fluid other than air. As another alternative, the air gap may be eliminated, and the cover layer 1700 may rest directly on the antenna 1500. The cover layer 1700 can protect the antenna 1500 from the environment and/or mechanical damage caused by external objects. In one embodiment, the cover layer 1700 provides a lensing effect to focus the energy of the transmitted signals 106 emitted by the antenna 1500 into a beam or to focus the energy of the reflected echoes 108 toward the antenna 1500.

This lensing effect can permit transmitted signals 106 and/or echoes 108 to pass through additional layers 1702 of materials (e.g., insulators such as Teflon, polycarbonate, or other polymers) that are positioned between the antenna 1500 and the target object 104 (shown in FIG. 18). For example, the sensing assembly 102 can be mounted to an object being monitored (e.g., the top of a tank of fluid being measured by the sensing assembly 102), while the lensing effect can permit the sensing assembly 102 to transmit the signals 106 and receive the echoes 108 through the top of the tank without cutting windows or openings through the top of the tank).

In one embodiment, the substrate 1708 may have a thickness dimension between the opposite surfaces that is thinner than a wavelength of the carrier signal of the transmitted signals 106 and/or echoes 108. For example, the thickness of the substrate 1708 may be on the order of ½0th of a wavelength. The thicknesses of the air gap 1704 and/or superstrate 1700 may be larger, such as ⅓ of the wavelength. Either one or both of the air gap 1704 and the superstrate 1700 may also be removed altogether.

One or more embodiments of the system 100 and/or sensing assembly 102 described herein may be used for a variety of applications that use the separation distance 110 and/or time of flight that is measured by the sensing assembly 102. Several specific examples of applications of the system 100 and/or sensing assembly 102 are described herein, but not all applications or uses of the system 100 or sensing assembly 102 are limited to those set forth herein. For example, many applications that use the detection of the separation distance 110 (e.g., as a depth measurement) can use or incorporate the system 100 and/or sensing assembly 102.

Figure 36:
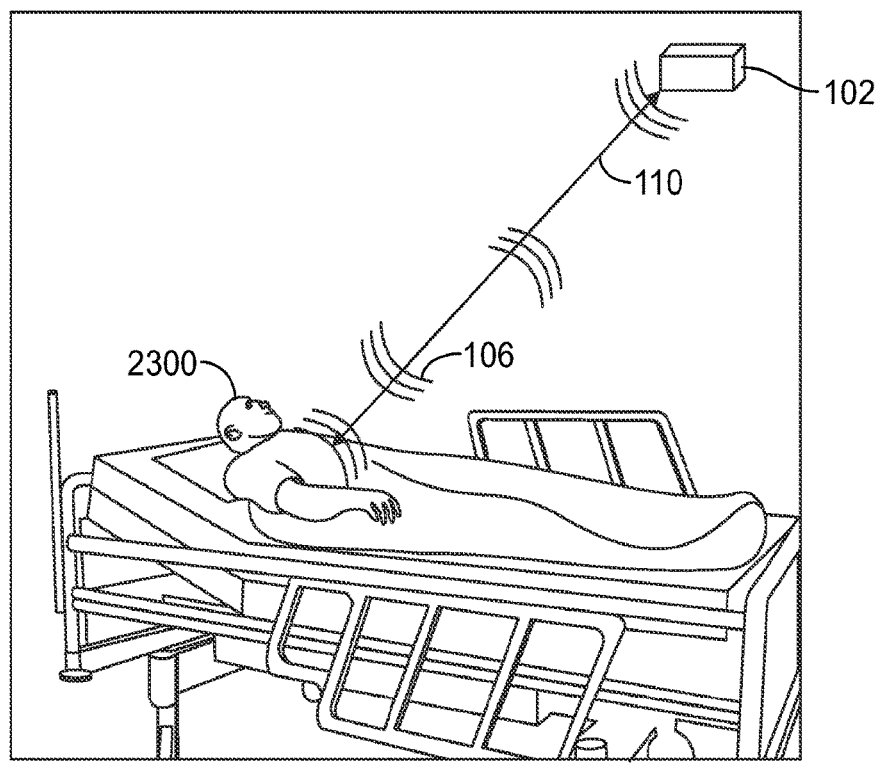
FIG. 36 is a schematic diagram of one example of using the sensing assembly shown in FIG. 18 in a medical application.

FIG. 36 is a schematic diagram of one example of using the sensing assembly 102 in a medical application. The sensing assembly 102 may use one or more of the stages described above (e.g., coarse stage, fine stage, and ultrafine stage) to monitor changes in position of a patient 2300 and/or relatively small movements of the patient. For example, the ultrafine stage determination of movement described above may be used for breath rate detection, heart rate detection, monitoring gross motor or muscle movement, and the like. Breath rate, heart rate and activity can be useful for diagnosing sleep disorders, and since the sensing is non-contact and can be more comfortable for the patient being observed. As one example, the separation distance 110 to the abdomen and/or chest of the patient 2300 can be determined to within one bit of the digital pulse sequence (e.g., the bit of interest), as described above. The sensing assembly 102 can then track relatively small motions of the chest and/or abdomen within the subset of interest to track a breathing rate and/or heart rate. Additionally or alternatively, the sensing assembly 102 can track the motions of the chest and/or abdomen and combine the motions with a known, measured, observed, or designated size of the abdomen to estimate the tidal volume of breaths of the patient 2300. Additionally or alternatively, the sensing assembly 102 can track the motions of the chest and abdomen together to detect paradoxical breathing of the patient 2300.

As another example, the sensing assembly 102 may communicate transmitted signals 106 that penetrate into the body of the patient 2300 and sense the motion or absolute position of various internal structures, such as the heart. Many of these positions or motions can be relatively small and subtle, and the sensing assembly 102 can use the ultrafine stage determination of motion or the separation distance 110 to sense the motion or absolute position of the internal structures.

Using the non-contact sensing assembly 102 also may be useful for situations where it is impossible or inconvenient to use wired sensors on the patient 2300 (e.g., sensors mounted directly to the test subject, connected by wires back to a medical monitor). For example, in high-activity situations where conventional wired sensors may get in the way, the sensing assembly 102 may monitor the separation distance 110 and/or motion of the patient 2300 from afar.

In another example, the sensing assembly 102 can be used for posture recognition and overall motion or activity sensing. This can be used for long-term observation of the patient 2300 for the diagnosis of chronic conditions, such as depression, fatigue, and overall health of at-risk individuals such as the elderly, among others. In the case of diseases with relatively slow onset, such as depression, the long term observation by the sensing assembly 102 may be used for early detection of the diseases. Also, since the unit can detect the medical parameters or quantities without anything being mounted on the patient 2300, the sensing assembly 102 may be used to make measurements of the patient 2300 without the knowledge or cooperation of the patient 2300. This could be useful in many situations, such as when dealing with children who would be made upset if sensors are attached to them. It may also give an indication of the mental state of a patient 2300, such as their breath becoming rapid and shallow when they become nervous. This would give rise to a remote lie-detector functionality.

In another embodiment, data generated by the sensing assembly 102 may be combined with data generated or obtained by one or more other sensors. For example, calculation of the separation distance 110 by the sensing assembly 102 may be used as a depth measurement that is combined with other sensor data. Such combination of data from different sensors is referred to herein as sensor fusion, and includes the fusing of two or more separate streams of sensor data to form a more complete picture of the phenomena or object or environment that is being sensed.

As one example, separation distances 110 calculated using the sensing assembly 102 may be combined with two-dimensional image data acquired by a camera. For example, without the separation distances 110, a computer or other machine may not be able to determine the actual physical size of the objects in a two-dimensional image.

Figure 37:
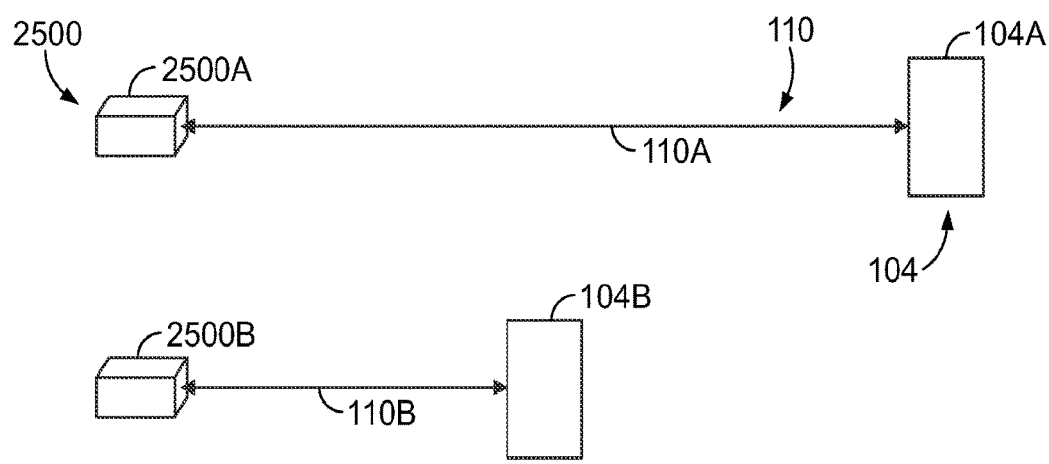
FIG. 37 is a schematic diagram of another embodiment of a sensing system.

FIG. 37 is a schematic diagram of a sensing system 2500 that may include the sensing assembly 102 (shown in FIG. 1) in accordance with one embodiment. Many types of sensors such as light level sensors, radiation sensors, moisture content sensors, and the like, obtain measurements of target objects 104 that may change as the separation distance 110 between the sensors and the target objects 104 varies. The sensing systems 2500 shown in FIG. 37 may include or represent one or more sensors that acquire information that changes as the separation distance 110 changes and may include or represent the sensing assembly 102. Distance information (e.g., separation distances 110) from the sensing systems 2500 and the target objects 104 can provide for calibration or correction of other sensor information that is dependent on the distance between the sensor and the targets being read or monitored by the sensor.

For example, the sensing systems 2500 can acquire or measure information (e.g., light levels, radiation, moisture, heat, and the like) from the target objects 104A, 104B and the separation distances 110A, 110B to the target objects 104A, 104B. The separation distances 110A, 110B can be used to correct or calibrate the measured information. For example, if the target objects 104A, 104B both provide the same light level, radiation, moisture, heat, and the like, the different separation distances 110A, 110B may result in the sensing systems 2500A, 2500B measuring different light levels, radiation, moisture, heat, and the like. With the sensing assembly 102 (shown in FIG. 1) measuring the separation distances 110A, 110B, the measured information for the target object 104A and/or 104B can be corrected (e.g., increased based on the size of the separation distance 110A for the target object 104A and/or decreased based on the size of the separation distance 110B for the target object 104B) so that the measured information is more accurate relative to not correcting the measured information for the different separation distances 110.

As another example, the sensing system 2500 may include a reflective pulse oximetry sensor and the sensing assembly 102. Two or more different wavelengths of light are directed at the surface of the target object 104 by the system 2500 and a photo detector of the system 2500 examines the scattered light. The ratio of the reflected power can be used to determine the oxygenation level of the blood in the target object 104. Instead of being directly mounted (e.g., engaged to) the body of the patient that is the target object 104, the sensing system 2500 may be spaced apart from the body of the patient.

The surface of the patient body can be illuminated with light sources and the sensing assembly 102 (shown in FIG. 1) can measure the separation distance 110 to the target object 104 (e.g., to the surface of the skin). The oxygenation level of the blood in the patient can then be calibrated or corrected for the decrease in the reflected power of the light that is caused by the sensing system 2500 being separated from the patient.

In another embodiment, the sensing assembly 102 and/or system 100 shown in FIG. 1 can be provided as a stand-alone unit that can communicate with other sensors, controllers, computers, and the like, to add the above-described functionality to a variety of sensor systems. A software-implemented system can collect and aggregate the information streams from the sensors and deliver the sensed information to the controlling system, where the separation distance 110 measured by the assembly 102 and/or system 100 is used in conjunction with the sensed information. Alternatively or additionally, the separation distances 110 measured by the assembly 102 can be collected along with a time stamp or other marker such as geographic location without communicating directly with the other sensors, controller, computer, and the like. The software-implemented system can then reconcile the separation distance 110 and other sensor data to align the measurements with each other.

The examples of sensor fusion described herein are not limited to just the combination of the sensing assembly 102 and one other sensor. Additional sensors may be used to aggregate the separation distances 110 and/or motion detected by the sensing assembly 102 with the data streams acquired by two or more additional sensors. For example, audio data (from a microphone), video data (from a camera), and the separation distances 110 and/or motion from the sensing assembly 102 can be aggregated to give a more complete understanding of a physical environment.

Figure 38A:
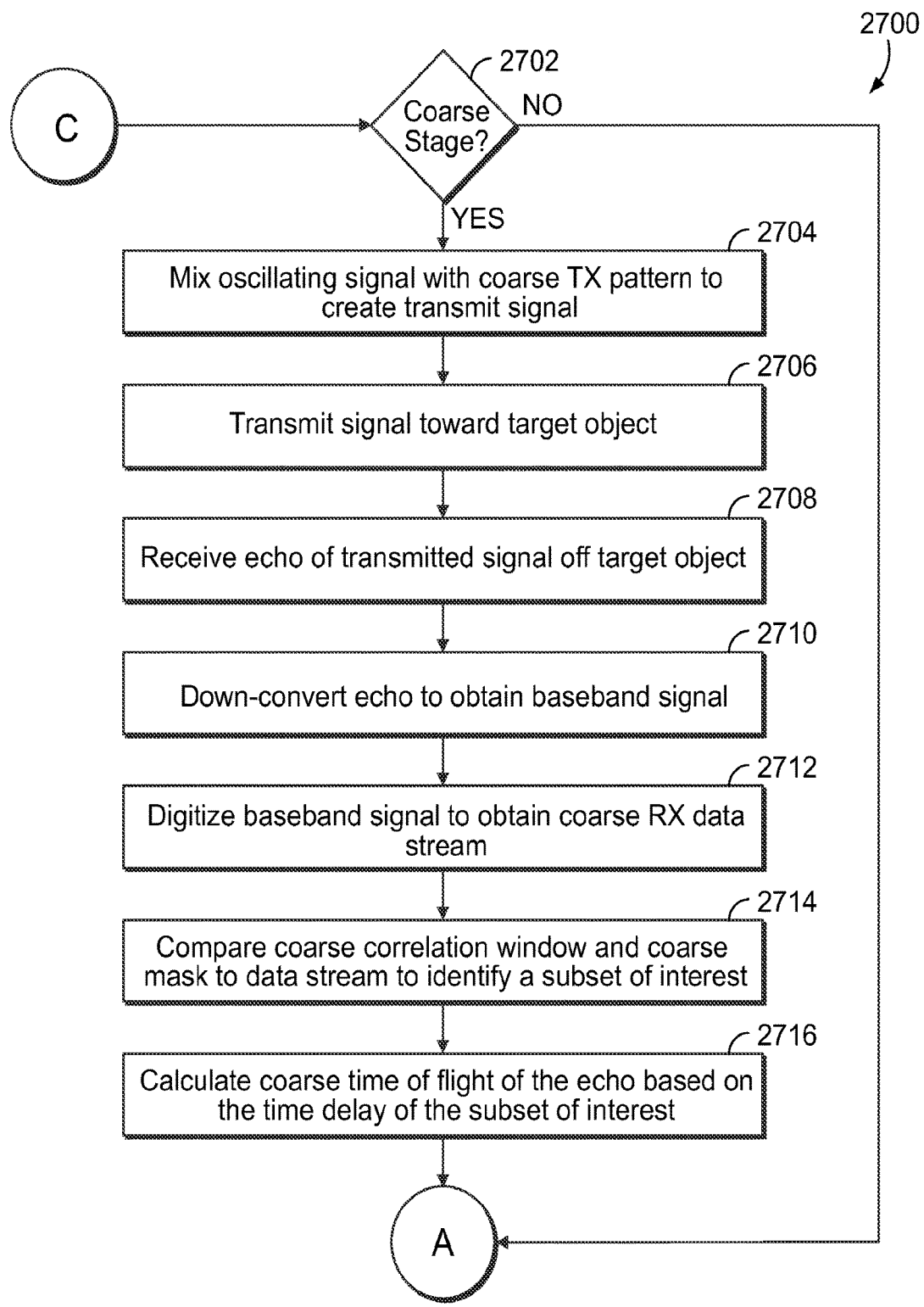
FIGS. 38A and 38B illustrate one embodiment of a method for sensing separation distances from a target object and/or motion of the target object.
Figure 38B:
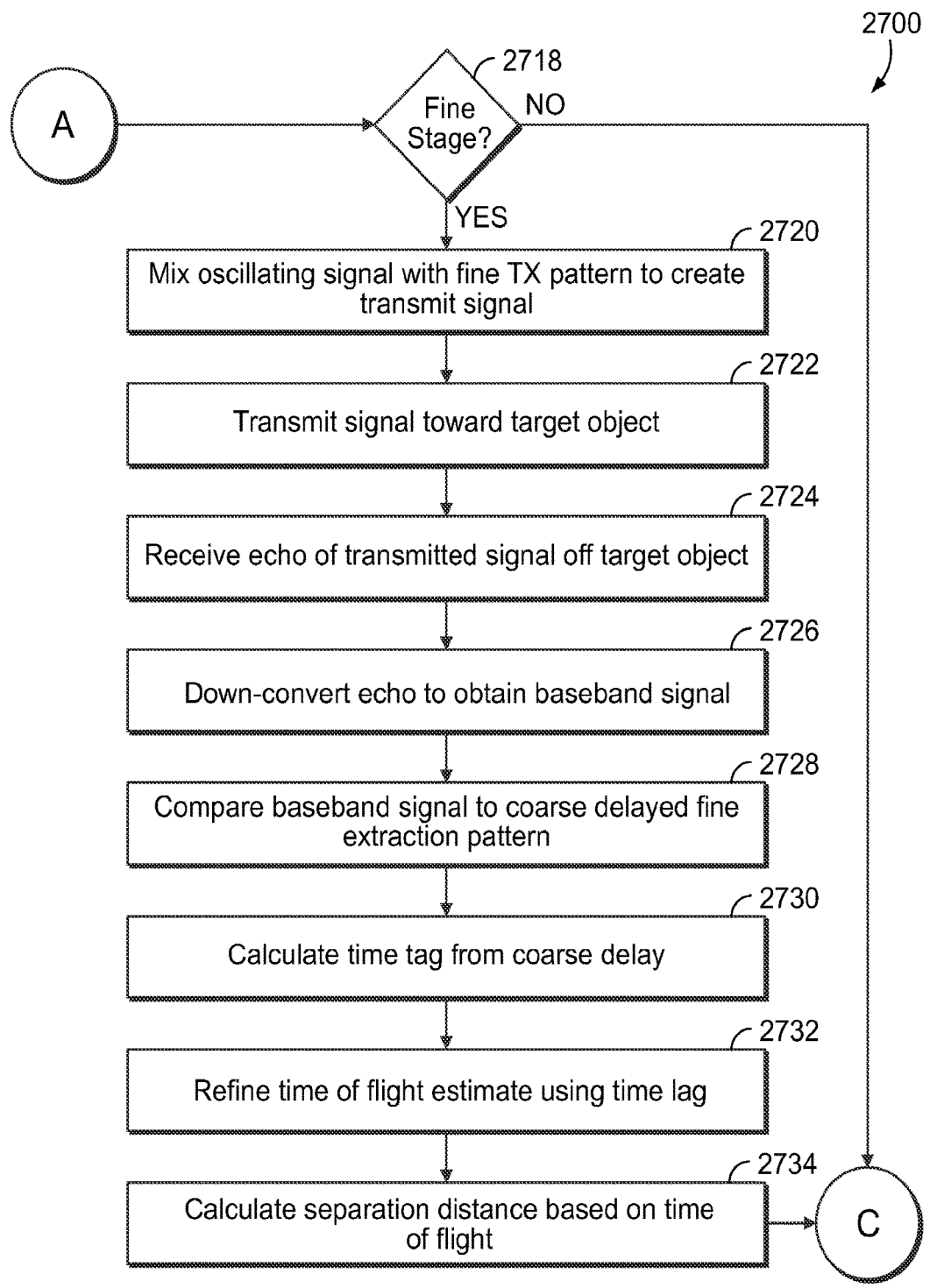

FIGS. 38A-B illustrate one embodiment of a method 2700 for sensing separation distances from a target object and/or motion of the target object. The method 2700 may be used in conjunction with one or more of the systems or sensing assemblies described herein.

At 2702, a determination is made as to whether to use to the coarse stage determination of the time of flight and/or separation distance. For example, an operator of the system 100 (shown in FIG. 1) may manually provide input to the system 100 and/or the system 100 may automatically determine whether to use the coarse stage determination described above. If the coarse stage determination is to be used, flow of the method 2700 proceeds to 2704. Alternatively, flow of the method 2700 may proceed to 2718. In one embodiment, the coarse stage uses a single channel (e.g., either the I channel or the Q channel) of the transmitted signal and received echo signal to determine the time of flight and/or separation distance, also as described above.

At 2704, an oscillating signal is mixed with a coarse transmit pattern to create a transmitted signal. For example, the oscillating signal 216 (shown in FIG. 2) is mixed with a digital pulse sequence of the transmit pattern signal 230 (shown in FIG. 2) to form the transmitted signal 106 (shown in FIG. 1), as described above.

At 2706, the transmitted signal is transmitted toward a target object. For example, the transmitting antenna 204 (shown in FIG. 2) may transmit the transmitted signal 106 (shown in FIG. 1) toward the target object 104 (shown in FIG. 1), as described above.

At 2708, echoes of the transmitted signal that are reflected off the target object are received. For example, the echoes 108 (shown in FIG. 1) that are reflected off the target object 104 (shown in FIG. 1) are received by the receiving antenna 206 (shown in FIG. 2), as described above.

At 2710, the received echoes are down converted to obtain a baseband signal. For example, the echoes 108 (shown in FIG. 1) are converted into the baseband echo signal 226 (shown in FIG. 2). For example, the received echo signal 224 may be mixed with the same oscillating signal 216 (shown in FIG. 2) that was mixed with the coarse transmit pattern signal 230 (shown in FIG. 2) to generate the transmitted signal 106 (shown in FIG. 1). The echo signal 224 can be mixed with the oscillating signal 216 to generate the baseband echo signal 226 (shown in FIG. 2) as the coarse receive data stream, as described above.

At 2712, the baseband signal is digitized to obtain the coarse receive data stream. For example, it may pass through the baseband processor 232 including the digitizer 730 to produce the digitized echo signal 740.

At 2714, a correlation window (e.g., a coarse correlation window) and a coarse mask are compared to the data stream to identify a subset of interest. Alternatively, the mask (e.g., a mask to eliminate or change one or more portions of the data stream) may not be used. In one embodiment, the coarse correlation window 320 (shown in FIG. 3) that includes all or a portion of the coarse transmit pattern included in the transmitted signal 106 (shown in FIG. 1) is compared to various subsets or portions of the digitized echo signal 740 (shown in FIG. 2), as described above. Correlation values can be calculated for the various subsets of the data stream 226, and the subset of interest may be identified by comparing the correlation values, such as by identifying the subset having a correlation value that is the greatest or is greater than one or more other subsets of interest.

At 2716, a time of flight of the transmitted signal and echo is calculated based on a time delay of the subset of interest. This time of flight can be referred to as a coarse time of flight. As described above, the subset of interest can be associated with a time lag ($t_d$) between transmission of the transmitted signal 106 (shown in FIG. 1) and the first bit of the subset of interest (or another bit in the subset of interest). The time of flight can be equal to the time lag, or the time of flight can be based on the time lag, with a correction or correlation factor (e.g., for the propagation of signals) being used to modify the time lag to the time of flight, as described above.

At 2718, a determination is made as to whether the fine stage determination of the separation distance is to be used. For example, a determination may be made automatically or manually to use the fine stage determination to further refine the measurement of the separation distance 110 (shown in FIG. 1) and/or to monitor or track motion of the target object 104 (shown in FIG. 1), as described above. If the fine stage is to be used, then flow of the method 2700 may proceed to 2720. On the other hand, if the fine stage is not to be used, then flow of the method 2700 may return to 2702.

At 2720, an oscillating signal is mixed with a digital pulse sequence to create a transmitted signal. As described above, the transmit pattern that is used in the fine stage may be different from the transmit pattern used in the coarse stage. Alternatively, the transmit pattern may be the same for the coarse stage and the fine stage.

At 2722, the transmitted signal is communicated toward the target object, similar to as described above in connection with 2706.

At 2724, echoes of the transmitted signal that are reflected off the target object are received, similar to as described above in connection with 2708.

At 2726, the received echoes are down converted to obtain a baseband signal. For example, the echoes 108 (shown in FIG. 1) are converted into the baseband echo signal 226 (shown in FIG. 2).

At 2728, the baseband signal 226 is compared to a fine receive pattern. The fine receive pattern may be delayed by the coarse time of flight, as described above. For example, instead of comparing the baseband signal with the receive pattern with both the baseband signal and the receive pattern having the same starting or initial time reference, the receive pattern may be delayed by the same time as the time delay measured by the coarse stage determination. This delayed receive pattern also may be referred to as a "coarse delayed fine extraction pattern" 728.

At 2730, a time lag between the fine data stream and the time delayed receive pattern is calculated. This time lag may represent the temporal overlap or mismatch between the waveforms in the fine data stream and the time delayed receive pattern, as described above in connection with FIGS. 26 through 29. The time lag may be measured as the energies of the waveforms that represent the overlap between the fine data stream and the time delayed receive pattern. As described above, time periods 808, 810, 904, 906 (shown in FIGS. 26 and 27) representative of the time lag may be calculated.

At 2732, the time of flight measured by the coarse stage (e.g., the "time of flight estimate") is refined by the time lag. For example, the time lag calculated at 2730 can be added to the time of flight calculated at 2716. Alternatively, the time lag may be added to a designated time of flight, such as a time of flight associated with or calculated from a designated or known separation distance 110 (shown in FIG. 1).

At 2734, the time of flight (that includes the time lag calculated at 2732) is used to calculate the separation distance from the target object, as described above. Flow of the method 2700 may then return to 2702 in a loop-wise manner. The above methods can be repeated for the I and Q channels separately or in parallel using parallel paths as in FIG. 30 or a switch or multiplexed path as described above to extract differences in the I and Q channels. These differences can be examined to resolve the phase of the echoes.

In one embodiment, performance of the fine stage determination (e.g., as described in connection with 2720 through 2732) is performed on one of the I or Q components of channels of the transmit signal and the echo signal, as described above. For example, the I channel of the echo signal 226 (shown in FIG. 2) may be examined in order to measure the amount of temporal overlap between the time-delayed receive pattern and the echo signal 226, as described above. In order to perform the ultrafine stage determination, a similar examination may be performed on another component or channel of the echo signal, such as the Q channel. For example, the I channel analysis of the echo signal 226 (e.g., the fine stage) may be performed concurrently or simultaneously with the Q channel analysis of the same echo signal 226 (e.g., the ultrafine stage). Alternatively, the fine stage and ultrafine stage may be performed sequentially, with one of the I or Q channels being examined to determine a temporal overlap of the echo signal and the time-delayed receive pattern before the other of the Q or I channels being examined to determine a temporal overlap. The temporal overlaps of the I and Q channels are used to calculate time lags (e.g., I and Q channel time lags), which can be added to the coarse stage determination or estimate of the time of flight. This time of flight can be used to determine the separation distance 110 (shown in FIG. 1), as described above. Alternatively or additionally, the time lags of the waveforms in the I channel and Q channel can be examined to resolve phases of the echoes in order to calculate separation distance or motion of the target.

As described above, the ultrafine stage determination may alternatively or additionally involve a similar process as the coarse stage determination. For example, the coarse stage determination may examine the I channel of the receive pattern and the data stream to determine correlation values of different subsets of the data stream and, from those correlation values, determine a subset of interest and a corresponding time-of-flight, as described herein. The ultrafine stage determination can use the Q channel of the receive pattern and the data stream to determine correlation values of different subsets of the data stream and, from those correlation values, determine a subset of interest and a time-of-flight, as described above. The times-of-flight from the I channel and Q channel can be combined (e.g., averaged) to calculate a time of flight and/or separation distance to the target. The correlation values calculated by the ultrafine stage determination can be used to calculate an additional time delay that can be added to the time delays from the coarse stage and/or the fine stage to determine a time of flight and/or separation distance to the target. Alternatively or additionally, the correlation values of the waveforms in the I channel and Q channel can be examined to resolve phases of the echoes in order to calculate separation distance or motion of the target.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to one of ordinary skill in the art upon reviewing the above description. The scope of the inventive subject matter should, therefore, be determined with reference to the appended clauses, along with the full scope of equivalents to which such clauses are entitled. In the appended clauses, the terms "including" and "in which" are used as the plain-English equivalents of the respective terms "comprising" and "wherein." Moreover, in the following clauses, the terms "first," "second," and "third," etc. are used merely as labels, and are not intended to impose numerical requirements on their objects. Further, the limitations of the following clauses are not written in means-plus-function format and are not intended to be interpreted based on 35 U.S.C. § 112, sixth paragraph, unless and until such clause limitations expressly use the phrase "means for" followed by a statement of function void of further structure.

This written description uses examples to disclose several embodiments of the inventive subject matter and also to enable one of ordinary skill in the art to practice the embodiments of inventive subject matter, including making and using any devices or systems and performing any incorporated methods. The patentable scope of the inventive subject matter is defined by the clauses, and may include other examples that occur to one of ordinary skill in the art. Such other examples are intended to be within the scope of the clauses if they have structural elements that do not differ from the literal language of the clauses, or if they include equivalent structural elements with insubstantial differences from the literal languages of the clauses.

The foregoing description of certain embodiments of the present inventive subject matter will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (for example, processors or memories) may be implemented in a single piece of hardware (for example, a general purpose signal processor, microcontroller, random access memory, hard disk, and the like). Similarly, the programs may be stand alone programs, may be incorporated as subroutines in an operating system, may be functions in an installed software package, and the like. The various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present inventive subject matter are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

The invention claimed is:

1. A sensing system comprising:
a first radar sensing assembly configured to measure plural first distances to a first target location located on at least one of a front, side, or back of a chest of a human being at different times by transmitting electromagnetic waves; and
an analysis system configured to receive the plural first distances from the first radar sensing assembly, the analysis system also is configured to calculate first differences in the plural first distances measured by the first radar sensing assembly, wherein the analysis system is configured to determine a breathing pattern signal from the first differences in the plural first distances, the analysis system also configured to monitor respiration of the human being using the breathing pattern signal, and
wherein the analysis system also is configured to extract a cardiac signal of the human being from the breathing pattern signal, the cardiac signal representing cardiac cycles of the human being.

2. The sensing system of claim 1, wherein the analysis system is configured to determine a posture of a human being using at least one of the plural first distances or the first differences in the plural first distances that are measured by the first radar sensing assembly.

3. The sensing system of claim 1, wherein the analysis system is configured to determine a presence of the target object at the common target location using at least one of the plural first distances or the first differences in the plural first distances that are calculated.

4. The sensing system of claim 1, further comprising a second radar sensing assembly configured to measure plural second distances to a second target location at different times using the electromagnetic waves, the second target location being different than the first target location, wherein the analysis system also is configured to calculate second differences in the plural second distances measured by the second radar sensing assembly.

5. The sensing system of claim 4, wherein the first target location is on a first body part of the human being and the second target location is on a different, second body part of the human being.

6. The sensing system of claim 1, wherein the analysis system is configured to detect the human being falling using one or more of the first plural distances or the first differences.

7. The sensing system of claim 1, wherein the human being is moving relative to the first radar sensing assembly, and further comprising a second radar sensing assembly configured to measure plural second distances to the first target location using first electromagnetic waves, wherein the analysis system is configured to track a movement path of the human being using the first distances measured by the first radar sensing assembly and the second distances measured by the second radar sensing assembly.

8. The sensing assembly of claim 1, further comprising one or more laser light sources configured to generate laser light toward the first target location and one or more optical receivers configured to detect reflection of the laser light off the first target location, wherein the analysis system is configured to determine an oxygenation level of blood of the target object based on the first differences and the reflection of the laser light.

9. A sensing method comprising:
transmitting first electromagnetic waves toward a first target location on a chest of a human being from a first radar sensing assembly;
receiving first echoes of the first electromagnetic waves that are reflected off the first target location using the first radar sensing assembly;
measuring plural first distances to the first target location using the first echoes of the first electromagnetic waves;
calculating first differences in the plural first distances measured by the first radar sensing assembly;
determining a breathing pattern signal from the first differences in the plural first distances;
monitoring respiration of the human being using the breathing pattern signal; and
extracting a cardiac signal of the human being from the breathing pattern signal, the cardiac signal representing cardiac cycles of the human being.

10. The sensing method of claim 9, further comprising determining a posture of the human being using at least one of the plural first distances or the first differences in the plural first distances that are measured by the first radar sensing assembly.

11. The sensing method of claim 9, further comprising determining a presence of the human being using at least one of the plural first distances or the first differences in the plural first distances that are calculated.

12. The sensing method of claim 9, further comprising:
transmitting second electromagnetic waves toward a second target location on the human being from a second radar sensing assembly, the second target location being different than the first target location;
receiving second echoes of the second electromagnetic waves that are reflected off the second target location using the second radar sensing assembly;
measuring plural second distances to the second target location using the second echoes of the second electromagnetic waves; and
identifying movements of the human being at the second target location by calculating second differences in the plural second distances measured by the second radar sensing assembly.

13. The sensing method of claim 12, wherein the first target location is on a first body part of the human being and the second target location is on a different, second body part of the human being.

14. The sensing method of claim 9, further comprising detecting the human being falling using at least one of the first distances or the first differences.

15. The sensing method of claim 9, wherein the target object is moving relative to the first radar sensing assembly, and further comprising:
transmitting second electromagnetic waves toward the first target location from a second radar sensing assembly;
receiving second echoes of the second electromagnetic waves that are reflected off the first target location using the second radar sensing assembly;
measuring plural second distances to the first target location using the second echoes of the electromagnetic waves; and
tracking a movement path of the human being using the first distances measured by the first radar sensing assembly and the second distances measured using the second radar sensing assembly.

16. The sensing method of claim 9, further comprising:
generating laser light toward the first target location from one or more laser light sources;
measuring reflection of the laser light off the first target location; and
calculating an oxygenation level of blood in the target object based on the first distances and the reflection of the laser light that is measured.

\* \* \* \* \*